US010758424B2

(12) United States Patent
Blott et al.

(10) Patent No.: US 10,758,424 B2
(45) Date of Patent: Sep. 1, 2020

(54) DRESSING AND APPARATUS FOR CLEANSING THE WOUNDS

(71) Applicant: Smith & Nephew PLC, Watford, Hertfordshire (GB)

(72) Inventors: Patrick Lewis Blott, York (GB); Edward Yerbury Hartwell, Hull (GB); Julian Lee-Webb, York (GB); Derek Nicolini, Hull (GB)

(73) Assignee: Smith & Nephew PLC, Watford (GB)

(*) Notice: Subject to any disclaimer, the term of this patent is extended or adjusted under 35 U.S.C. 154(b) by 357 days.

(21) Appl. No.: 15/894,706

(22) Filed: Feb. 12, 2018

(65) Prior Publication Data
US 2018/0169309 A1 Jun. 21, 2018

Related U.S. Application Data

(60) Division of application No. 14/668,774, filed on Mar. 25, 2015, now Pat. No. 10,039,868, which is a (Continued)

(30) Foreign Application Priority Data

Apr. 28, 2004 (GB) .................................. 0409446.2

(51) Int. Cl.
A61M 1/00 (2006.01)
A61F 13/00 (2006.01)

(52) U.S. Cl.
CPC ..... *A61F 13/00068* (2013.01); *A61M 1/0031* (2013.01); *A61M 1/0037* (2013.01); *A61M 1/0088* (2013.01)

(58) Field of Classification Search
CPC .............. A61M 1/0058; A61M 1/0025; A61M 1/0027; A61M 1/0062; A61M 1/0084; A61M 1/0088
See application file for complete search history.

(56) References Cited

U.S. PATENT DOCUMENTS 1,066,934 A 7/1913 Manney
2,280,915 A 4/1942 Johnson
(Continued)

FOREIGN PATENT DOCUMENTS

CA 2 369 024 10/2000
CA 2 369 022 8/2005
(Continued)

OTHER PUBLICATIONS

Brief Communication—Letter from the Proprietor of the Patent, re the Opposition of European Patent No. EP 3 056 241, dated Jan. 31, 2020, in 52 pages.
(Continued)

*Primary Examiner* — Susan S Su

(74) *Attorney, Agent, or Firm* — Knobbe, Martens, Olson & Bear, LLP

(57) ABSTRACT

A dressing (2) and an apparatus (1) comprising the dressing, for cleansing the wounds (5) in which an irrigant fluid from a reservoir (12) connected to a conformable would dressing and would exudate from the dressing are moved by a device (18) (which may be a single pump or two pumps) for moving fluid through a flow Path (6, 7, 9, 10) which passes through the dressing with a means for providing simultaneous aspiration and irrigation of the wound, to provide a desired balance of fluid at a controlled nominal flow rate that removes materials deleterious to wound healing, while distributing materials that are beneficial in promoting would healing over the wound bed.

15 Claims, 30 Drawing Sheets

Related U.S. Application Data continuation of application No. 13/213,491, filed on Aug. 19, 2011, now Pat. No. 9,044,569, which is a continuation of application No. 10/599,722, filed as application No. PCT/GB2005/001603 on Apr. 27, 2005, now Pat. No. 8,105,295.

(56) References Cited

U.S. PATENT DOCUMENTS

| | | |
|---|---|---|
| 2,910,763 A | 8/1955 | Lauterbach |
| 3,171,410 A | 3/1965 | Towle et al. |
| 3,288,140 A | 11/1966 | McCarthy |
| 3,367,332 A | 2/1968 | Groves |
| 3,568,675 A | 3/1971 | Harvey |
| 3,624,821 A | 11/1971 | Henderson |
| 3,633,567 A | 1/1972 | Sarnoff |
| 3,786,801 A | 1/1974 | Sartorius |
| 3,808,178 A | 4/1974 | Gaylord |
| 3,874,387 A | 4/1975 | Barbieri |
| 3,922,957 A | 12/1975 | Ogle et al. |
| 3,993,080 A | 11/1976 | Loseff |
| 4,112,947 A | 9/1978 | Nehring |
| 4,117,551 A | 9/1978 | Books et al. |
| 4,136,696 A | 1/1979 | Nehring |
| 4,178,938 A | 12/1979 | Au |
| 4,180,074 A | 12/1979 | Murry et al. |
| 4,184,510 A | 1/1980 | Murry et al. |
| 4,224,945 A | 9/1980 | Cohen |
| 4,252,119 A | 2/1981 | Coates |
| 4,316,466 A | 2/1982 | Babb |
| 4,341,207 A | 7/1982 | Steer et al. |
| 4,360,021 A | 11/1982 | Stima |
| 4,366,169 A | 12/1982 | White |
| 4,382,441 A | 5/1983 | Svedman |
| 4,465,485 A | 8/1984 | Kashmer et al. |
| 4,466,431 A | 8/1984 | Tharrat et al. |
| 4,499,896 A | 2/1985 | Heinecke |
| 4,529,402 A | 7/1985 | Weilbacher et al. |
| 4,530,360 A | 7/1985 | Duarte |
| 4,538,920 A | 9/1985 | Drake et al. |
| 4,561,435 A | 12/1985 | McKnight et al. |
| 4,568,327 A | 2/1986 | Seufert |
| 4,573,965 A | 3/1986 | Russo |
| 4,587,101 A | 5/1986 | Marsoner et al. |
| 4,650,462 A | 3/1987 | DeSatnick et al. |
| 4,657,006 A | 4/1987 | Rawlings et al. |
| 4,664,662 A | 5/1987 | Webster |
| 4,699,134 A | 10/1987 | Samuelsen |
| 4,710,165 A | 12/1987 | McNeil et al. |
| 4,740,202 A | 4/1988 | Stacey |
| 4,753,536 A | 6/1988 | Spehar et al. |
| 4,759,354 A | 7/1988 | Quarfoot |
| 4,767,026 A | 8/1988 | Keller |
| 4,771,919 A | 9/1988 | Ernst |
| 4,778,446 A | 10/1988 | Jensen |
| 4,787,888 A | 11/1988 | Fox |
| 4,792,328 A | 12/1988 | Beck et al. |
| 4,798,603 A | 1/1989 | Meyer et al. |
| 4,813,931 A | 3/1989 | Hauze |
| 4,817,594 A | 4/1989 | Juhasz |
| 4,836,192 A | 6/1989 | Abbate |
| 4,841,962 A | 6/1989 | Berg et al. |
| 4,867,150 A | 9/1989 | Gilbert |
| 4,872,450 A | 10/1989 | Austad |
| 4,875,473 A | 10/1989 | Alvarez |
| 4,882,213 A | 11/1989 | Gaddis et al. |
| 4,921,488 A | 5/1990 | Maitz et al. |
| 4,930,997 A | 6/1990 | Bennett |
| 4,936,834 A | 6/1990 | Beck et al. |
| 4,950,483 A | 8/1990 | Ksander et al. |
| 4,969,880 A | 11/1990 | Zamierowski |
| 4,979,944 A | 12/1990 | Luzsicza |
| 4,997,425 A | 3/1991 | Shioya et al. |
| 5,009,635 A | 4/1991 | Scarberry |
| 5,010,883 A | 4/1991 | Rawlings et al. |
| 5,030,202 A | 7/1991 | Harris |
| 5,055,195 A | 10/1991 | Trasch et al. |
| 5,055,198 A | 10/1991 | Shettigar |
| 5,064,653 A | 11/1991 | Sessions et al. |
| 5,073,172 A | 12/1991 | Fell |
| 5,080,493 A | 1/1992 | McKown et al. |
| 5,080,661 A | 1/1992 | Lavender et al. |
| 5,100,396 A | 3/1992 | Zamierowski |
| 5,112,323 A | 5/1992 | Winkler et al. |
| 5,149,331 A | 9/1992 | Ferdman et al. |
| 5,152,757 A | 10/1992 | Eriksson |
| 5,176,663 A | 1/1993 | Svedman et al. |
| 5,218,973 A | 6/1993 | Weaver et al. |
| 5,249,709 A | 10/1993 | Duckworth et al. |
| 5,261,893 A | 11/1993 | Zamierowski |
| 5,264,218 A | 11/1993 | Rogozinski |
| 5,322,695 A | 6/1994 | Shah et al. |
| 5,328,614 A | 7/1994 | Matsumura |
| 5,333,760 A | 8/1994 | Simmen et al. |
| 5,336,209 A | 8/1994 | Porzilli |
| 5,358,494 A | 10/1994 | Svedman |
| 5,360,398 A | 11/1994 | Grieshaber et al. |
| 5,380,280 A | 1/1995 | Peterson |
| 5,419,768 A | 5/1995 | Kayser |
| 5,419,772 A | 5/1995 | Teitz et al. |
| 5,460,490 A | 10/1995 | Carr et al. |
| 5,466,229 A | 11/1995 | Elson |
| 5,486,158 A | 1/1996 | Samuelson |
| 5,487,889 A | 1/1996 | Eckert et al. |
| 5,490,984 A | 2/1996 | Freed |
| 5,496,605 A | 3/1996 | Augst et al. |
| 5,498,338 A | 3/1996 | Kruger et al. |
| 5,527,293 A | 6/1996 | Zamierowski |
| 5,527,923 A | 6/1996 | Klingler et al. |
| 5,549,584 A | 8/1996 | Gross |
| 5,578,317 A | 11/1996 | Mulder |
| 5,582,596 A | 12/1996 | Fukunaga et al. |
| 5,593,395 A | 1/1997 | Martz |
| 5,593,750 A | 1/1997 | Rothrum et al. |
| 5,599,289 A | 2/1997 | Castellana |
| 5,609,271 A | 3/1997 | Keller et al. |
| 5,616,387 A | 4/1997 | Augst et al. |
| 5,633,007 A | 5/1997 | Webb et al. |
| 5,636,643 A | 6/1997 | Argenta et al. |
| 5,645,081 A | 7/1997 | Argenta et al. |
| 5,662,924 A | 9/1997 | Rhodes |
| 5,676,650 A | 10/1997 | Grieshaber et al. |
| 5,678,564 A | 10/1997 | Lawrence et al. |
| 5,681,579 A | 10/1997 | Freeman |
| 5,713,881 A | 2/1998 | Rezai et al. |
| 5,714,225 A | 2/1998 | Hansen et al. |
| 5,716,411 A | 2/1998 | Orgill et al. |
| 5,733,253 A | 3/1998 | Headley et al. |
| 5,733,305 A | 3/1998 | Fleischmann |
| 5,759,570 A | 6/1998 | Arnold |
| 5,778,890 A | 7/1998 | Lofgren et al. |
| 5,792,090 A | 8/1998 | Ladin |
| 5,795,584 A | 8/1998 | Totakura et al. |
| 5,810,755 A | 9/1998 | LeVeen et al. |
| 5,810,765 A | 9/1998 | Oda |
| 5,830,176 A | 11/1998 | Mackool |
| 5,885,237 A | 3/1999 | Kadash et al. |
| 5,893,862 A | 4/1999 | Pratt et al. |
| 5,899,893 A | 5/1999 | Dyer et al. |
| 5,904,659 A | 5/1999 | Duarte |
| 5,910,125 A | 6/1999 | Cummings et al. |
| 5,911,222 A | 6/1999 | Lawrence et al. |
| 5,941,859 A | 8/1999 | Lerman |
| 5,954,680 A | 9/1999 | Augustine |
| 5,958,420 A | 9/1999 | Jenson |
| 5,964,723 A | 10/1999 | Augustine |
| 5,976,117 A | 11/1999 | Dunshee et al. |
| 5,981,822 A | 11/1999 | Addison |
| 5,985,990 A | 11/1999 | Kantner et al. |
| 5,986,163 A | 11/1999 | Augustine |
| 6,071,267 A | 6/2000 | Zamierowski |
| 6,087,549 A | 7/2000 | Flick |
| 6,110,197 A | 8/2000 | Augustine et al. |
| 6,117,111 A | 9/2000 | Fleischmann |

(56) References Cited

U.S. PATENT DOCUMENTS

| | | |
|---|---|---|
| 6,142,982 A | 11/2000 | Hunt et al. |
| 6,156,334 A | 12/2000 | Meyer-Ingold et al. |
| 6,159,160 A | 12/2000 | Hsei et al. |
| 6,168,800 B1 | 1/2001 | Dobos et al. |
| 6,201,164 B1 | 3/2001 | Wulff et al. |
| 6,203,563 B1 | 3/2001 | Fernandez |
| 6,252,129 B1 | 6/2001 | Coffee |
| 6,254,567 B1 | 7/2001 | Treu et al. |
| 6,261,283 B1 | 7/2001 | Morgan et al. |
| 6,293,281 B1 | 9/2001 | Shultz et al. |
| 6,345,623 B1 | 2/2002 | Heaton et al. |
| 6,350,339 B1 | 2/2002 | Sessions |
| 6,391,294 B1 | 5/2002 | Dettmar et al. |
| 6,398,761 B1 | 6/2002 | Bills et al. |
| 6,398,767 B1 | 6/2002 | Fleischmann |
| 6,458,109 B1 | 10/2002 | Henley et al. |
| 6,465,708 B1 | 10/2002 | Augustine |
| 6,486,285 B2 | 11/2002 | Fujita |
| 6,496,727 B1 | 12/2002 | Bernhard et al. |
| 6,520,982 B1 | 2/2003 | Boynton et al. |
| 6,527,745 B1 | 3/2003 | Kanda et al. |
| 6,553,998 B2 | 4/2003 | Heaton et al. |
| 6,626,827 B1 | 9/2003 | Felix et al. |
| 6,626,891 B2 | 9/2003 | Ohmstede |
| 6,629,774 B1 | 10/2003 | Guruendeman |
| 6,648,862 B2 | 11/2003 | Watson |
| 6,673,982 B1 | 1/2004 | Chen et al. |
| 6,676,610 B2 | 1/2004 | Morton et al. |
| 6,680,113 B1 | 1/2004 | Lucast et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,787,682 B2 | 9/2004 | Gilman |
| 6,794,554 B2 | 9/2004 | Sessions et al. |
| 6,797,855 B2 | 9/2004 | Worthley |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,974,428 B2 | 12/2005 | Knutson et al. |
| 6,977,323 B1 | 12/2005 | Swenson |
| 6,979,324 B2 | 12/2005 | Bybordi et al. |
| 7,004,915 B2 | 2/2006 | Boynton et al. |
| 7,005,556 B1 | 2/2006 | Becker et al. |
| 7,022,113 B2 | 4/2006 | Lockwood et al. |
| 7,030,288 B2 | 4/2006 | Liedtke et al. |
| 7,041,868 B2 | 5/2006 | Greene et al. |
| 7,048,951 B1 | 5/2006 | Seitz et al. |
| 7,070,584 B2 | 7/2006 | Johnson et al. |
| 7,077,832 B2 | 7/2006 | Fleischmann |
| 7,087,807 B2 | 8/2006 | Stapf |
| 7,108,683 B2 | 9/2006 | Zamierowski |
| 7,122,046 B2 | 10/2006 | Augustine et al. |
| 7,137,968 B1 | 11/2006 | Burrell et al. |
| 7,144,390 B1 | 12/2006 | Hannigan et al. |
| 7,182,758 B2 | 2/2007 | McCraw |
| 7,195,624 B2 | 3/2007 | Lockwood |
| 7,211,060 B1 | 5/2007 | Talish et al. |
| 7,214,202 B1 | 5/2007 | Vogel et al. |
| 7,216,651 B2 | 5/2007 | Argenta et al. |
| 7,220,889 B2 | 5/2007 | Sigurjonsson et al. |
| 7,291,762 B2 | 11/2007 | Flick |
| 7,335,809 B2 | 2/2008 | Riesinger |
| 7,338,482 B2 | 3/2008 | Lockwood et al. |
| 7,351,250 B2 | 4/2008 | Zamierowski |
| 7,361,184 B2 | 4/2008 | Joshi |
| 7,363,850 B2 | 4/2008 | Becker |
| 7,381,211 B2 | 6/2008 | Zamierowski |
| 7,381,859 B2 | 6/2008 | Hunt et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,494,482 B2 | 2/2009 | Orgill et al. |
| 7,507,870 B2 | 3/2009 | Nielsen et al. |
| 7,518,031 B2 | 4/2009 | Liedtke et al. |
| 7,524,315 B2 | 4/2009 | Blott et al. |
| 7,534,240 B1 | 5/2009 | Johnson |
| 7,534,927 B2 | 5/2009 | Lockwood |
| 7,540,848 B2 | 6/2009 | Hannigan et al. |
| 7,553,306 B1 | 6/2009 | Hunt et al. |
| 7,611,500 B1 | 11/2009 | Lina et al. |
| 7,625,362 B2 | 12/2009 | Boehringer et al. |
| 7,628,764 B2 | 12/2009 | Duarte et al. |
| 7,629,384 B2 | 12/2009 | Fossel |
| 7,645,253 B2 | 1/2010 | Gura et al. |
| 7,645,269 B2 | 1/2010 | Zamierowski |
| 7,670,323 B2 | 3/2010 | Hunt et al. |
| 7,678,090 B2 | 3/2010 | Risk, Jr. |
| 7,678,102 B1 | 3/2010 | Heaton |
| 7,699,830 B2 | 4/2010 | Martin |
| 7,722,582 B2 | 5/2010 | Lina et al. |
| 7,753,894 B2 | 7/2010 | Blott et al. |
| 7,754,937 B2 | 7/2010 | Boehringer et al. |
| 7,759,537 B2 | 7/2010 | Bishop et al. |
| 7,759,538 B2 | 7/2010 | Fleischmann |
| 7,763,769 B2 | 7/2010 | Johnson et al. |
| 7,767,936 B2 | 8/2010 | Ferguson |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,811,269 B2 | 10/2010 | Boynton et al. |
| 7,828,782 B2 | 11/2010 | Suzuki |
| 7,846,141 B2 | 12/2010 | Weston |
| 7,862,718 B2 | 1/2011 | Doyen et al. |
| 7,867,206 B2 | 1/2011 | Lockwood et al. |
| 7,883,494 B2 | 2/2011 | Martin |
| 7,896,864 B2 | 3/2011 | Lockwood et al. |
| 7,910,791 B2 | 3/2011 | Coffey |
| 7,951,100 B2 | 5/2011 | Hunt et al. |
| 7,964,766 B2 | 6/2011 | Blott et al. |
| 7,976,519 B2 | 7/2011 | Bubb et al. |
| 7,981,098 B2 | 7/2011 | Boehringer et al. |
| 7,988,680 B2 | 8/2011 | Lockwood et al. |
| 8,062,272 B2 | 11/2011 | Weston |
| 8,062,331 B2 | 11/2011 | Zamierowski |
| 8,070,773 B2 | 12/2011 | Zamierowski |
| 8,080,702 B2 | 12/2011 | Blott et al. |
| 8,100,887 B2 | 1/2012 | Weston et al. |
| 8,105,295 B2 | 1/2012 | Blott et al. |
| 8,123,781 B2 | 2/2012 | Zamierowski |
| 8,128,615 B2 | 3/2012 | Blott et al. |
| 8,162,909 B2 | 4/2012 | Blott et al. |
| 8,168,848 B2 | 5/2012 | Lockwood et al. |
| 8,246,592 B2 | 8/2012 | Lockwood et al. |
| 8,257,327 B2 | 9/2012 | Blott et al. |
| 8,348,910 B2 | 1/2013 | Blott et al. |
| 8,357,188 B2 | 1/2013 | Boynton et al. |
| 8,398,614 B2 | 3/2013 | Blott et al. |
| 8,529,548 B2 | 9/2013 | Blott et al. |
| 8,529,578 B2 | 9/2013 | Daniels et al. |
| D692,565 S | 10/2013 | Lattimore et al. |
| 8,569,566 B2 | 10/2013 | Blott et al. |
| 8,647,327 B2 | 2/2014 | Larsson et al. |
| 8,747,887 B2 | 6/2014 | Coffey |
| 8,758,313 B2 | 6/2014 | Blott et al. |
| 8,834,451 B2 | 9/2014 | Blott et al. |
| 8,845,619 B2 | 9/2014 | Blott et al. |
| 8,870,837 B2 | 10/2014 | Locke et al. |
| 8,882,746 B2 | 11/2014 | Blott et al. |
| 8,926,592 B2 | 1/2015 | Blott et al. |
| 9,044,569 B2 | 6/2015 | Blott et al. |
| 9,050,208 B2 | 6/2015 | Locke et al. |
| 9,205,001 B2 | 12/2015 | Blott et al. |
| 9,289,542 B2 | 3/2016 | Blott et al. |
| 9,387,126 B2 | 7/2016 | Blott et al. |

(56) References Cited

U.S. PATENT DOCUMENTS

| | | |
|---|---|---|
| 9,452,244 B2 | 9/2016 | Blott et al. |
| 9,452,248 B2 | 9/2016 | Blott et al. |
| 9,526,817 B2 | 12/2016 | Blott et al. |
| 9,545,463 B2 | 1/2017 | Blott et al. |
| 9,616,208 B2 | 4/2017 | Blott et al. |
| 9,844,473 B2 | 12/2017 | Blott et al. |
| 9,844,474 B2 | 12/2017 | Blott et al. |
| 10,035,006 B2 | 7/2018 | Blott et al. |
| 10,278,869 B2 | 5/2019 | Blott et al. |
| 10,342,729 B2 | 7/2019 | Blott et al. |
| 2001/0000795 A1 | 5/2001 | Bolian, II et al. |
| 2001/0004082 A1 | 6/2001 | Keller et al. |
| 2001/0018072 A1 | 8/2001 | Unger |
| 2001/0020145 A1 | 9/2001 | Satterfield et al. |
| 2001/0027285 A1 | 10/2001 | Heinecke et al. |
| 2001/0029956 A1 | 10/2001 | Argenta |
| 2001/0034499 A1 | 10/2001 | Sessions et al. |
| 2001/0037810 A1 | 11/2001 | Fine et al. |
| 2001/0043943 A1 | 11/2001 | Coffey |
| 2002/0016570 A1 | 2/2002 | Cartledge |
| 2002/0038826 A1 | 4/2002 | Hurray et al. |
| 2002/0068913 A1 | 6/2002 | Fleischmann |
| 2002/0082567 A1 | 6/2002 | Lockwood et al. |
| 2002/0114847 A1 | 8/2002 | Peshoff |
| 2002/0138036 A1 | 9/2002 | Babaev |
| 2002/0145007 A1 | 10/2002 | Sawhney et al. |
| 2002/0161346 A1 | 10/2002 | Lockwood et al. |
| 2002/0198490 A1 | 12/2002 | Wirt et al. |
| 2002/0198503 A1 | 12/2002 | Risk, Jr. et al. |
| 2002/0198504 A1 | 12/2002 | Risk et al. |
| 2003/0014022 A1 | 1/2003 | Lockwood et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0093041 A1 | 5/2003 | Risk, Jr. et al. |
| 2003/0108587 A1 | 6/2003 | Orgill et al. |
| 2003/0109855 A1 | 6/2003 | Solem et al. |
| 2003/0134332 A1 | 7/2003 | Boykin, Jr. |
| 2003/0144619 A1 | 7/2003 | Augustine |
| 2003/0148959 A1 | 8/2003 | Quirk et al. |
| 2003/0171675 A1 | 9/2003 | Rosenberg |
| 2003/0175798 A1 | 9/2003 | Raees et al. |
| 2003/0183653 A1 | 10/2003 | Bills |
| 2003/0211137 A1 | 11/2003 | Sierra |
| 2003/0212357 A1 | 11/2003 | Pace |
| 2003/0212431 A1 | 11/2003 | Brady et al. |
| 2003/0225347 A1 | 12/2003 | Argenta et al. |
| 2004/0001878 A1 | 1/2004 | DeBusk et al. |
| 2004/0019252 A1 | 1/2004 | Hirata |
| 2004/0024351 A1 | 2/2004 | Greter et al. |
| 2004/0033466 A1 | 2/2004 | Shellard et al. |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0077977 A1 | 4/2004 | Ella et al. |
| 2004/0127836 A1 | 7/2004 | Sigurjonsson et al. |
| 2004/0127845 A1 | 7/2004 | Renz et al. |
| 2004/0162512 A1 | 8/2004 | Liedtke et al. |
| 2004/0167617 A1 | 8/2004 | Voellmicke et al. |
| 2004/0171998 A1 | 9/2004 | Marasco, Jr. |
| 2004/0241214 A1 | 12/2004 | Kirkwood et al. |
| 2005/0004534 A1 | 1/2005 | Lockwood et al. |
| 2005/0065484 A1 | 3/2005 | Watson, Jr. |
| 2005/0090787 A1 | 4/2005 | Risk et al. |
| 2005/0107756 A1 | 5/2005 | McCraw |
| 2005/0113733 A1 | 5/2005 | Liedtke et al. |
| 2005/0130299 A1 | 6/2005 | Suzuki |
| 2005/0131327 A1 | 6/2005 | Lockwood et al. |
| 2005/0143697 A1 | 6/2005 | Riesinger |
| 2005/0164365 A1 | 7/2005 | Yonemura |
| 2005/0177190 A1 | 8/2005 | Zamierowski |
| 2005/0181163 A1 | 8/2005 | Kose |
| 2005/0230422 A1 | 10/2005 | Muller et al. |
| 2005/0261643 A1 | 11/2005 | Bybordi et al. |
| 2006/0025727 A1 | 2/2006 | Boehringer et al. |
| 2006/0029675 A1 | 2/2006 | Ginther |
| 2006/0041247 A1 | 2/2006 | Petrosenko et al. |
| 2006/0073036 A1 | 4/2006 | Debrito et al. |
| 2006/0142687 A1 | 6/2006 | Liedtke et al. |
| 2006/0172000 A1 | 8/2006 | Cullen et al. |
| 2006/0178608 A1 | 8/2006 | Stapf |
| 2006/0241689 A1 | 10/2006 | Leiboff et al. |
| 2007/0014837 A1 | 1/2007 | Johnson et al. |
| 2007/0021697 A1 | 1/2007 | Ginther et al. |
| 2007/0038172 A1 | 2/2007 | Zamierowski |
| 2007/0065303 A1 | 3/2007 | Tomell et al. |
| 2007/0066945 A1 | 3/2007 | Martin |
| 2007/0073200 A1 | 3/2007 | Hannigan et al. |
| 2007/0129660 A1 | 6/2007 | McLeod et al. |
| 2007/0141128 A1 | 6/2007 | Blott et al. |
| 2007/0142761 A1 | 6/2007 | Aali |
| 2007/0219497 A1 | 9/2007 | Johnson et al. |
| 2007/0292276 A1 | 12/2007 | Stutz et al. |
| 2007/0292488 A1 | 12/2007 | Bassiri et al. |
| 2008/0069855 A1 | 3/2008 | Bonutti |
| 2008/0095979 A1 | 4/2008 | Hatanaka et al. |
| 2008/0213344 A1 | 9/2008 | McCarthy et al. |
| 2008/0226720 A1 | 9/2008 | Kemp et al. |
| 2008/0243044 A1 | 10/2008 | Hunt et al. |
| 2008/0281281 A1 | 11/2008 | Meyer et al. |
| 2009/0012483 A1 | 1/2009 | Blott et al. |
| 2009/0054855 A1 | 2/2009 | Blott et al. |
| 2009/0069759 A1 | 3/2009 | Blott et al. |
| 2009/0099519 A1 | 4/2009 | Kaplan |
| 2009/0105671 A1 | 4/2009 | Daggar et al. |
| 2009/0130186 A1 | 5/2009 | McCarthy et al. |
| 2009/0177136 A1 | 7/2009 | Liedtke et al. |
| 2009/0204084 A1 | 8/2009 | Blott et al. |
| 2009/0221977 A1 | 9/2009 | Blott et al. |
| 2009/0227969 A1 | 9/2009 | Jaeb et al. |
| 2009/0240185 A1 | 9/2009 | Jaeb et al. |
| 2009/0275872 A1 | 11/2009 | Addison et al. |
| 2009/0306580 A1 | 12/2009 | Blott et al. |
| 2009/0306609 A1 | 12/2009 | Blatt et al. |
| 2009/0312723 A1 | 12/2009 | Blott et al. |
| 2010/0022972 A1 | 1/2010 | Lina et al. |
| 2010/0069885 A1 | 3/2010 | Stevenson et al. |
| 2010/0100022 A1 | 4/2010 | Greener et al. |
| 2010/0106117 A1 | 4/2010 | Lockwood et al. |
| 2010/0135915 A1 | 6/2010 | Greener et al. |
| 2010/0137775 A1 | 6/2010 | Hu et al. |
| 2010/0249733 A9 | 9/2010 | Blott et al. |
| 2010/0274167 A1 | 10/2010 | Martin |
| 2010/0297208 A1 | 11/2010 | Fry et al. |
| 2011/0004171 A1 | 1/2011 | Blott et al. |
| 2011/0009835 A1 | 1/2011 | Blott |
| 2011/0054423 A1 | 3/2011 | Blott et al. |
| 2011/0087176 A2 | 4/2011 | Blott et al. |
| 2011/0178451 A1 | 7/2011 | Robinson et al. |
| 2011/0213319 A1 | 9/2011 | Blott et al. |
| 2011/0213320 A1 | 9/2011 | Blott et al. |
| 2011/0251567 A1 | 10/2011 | Blott et al. |
| 2011/0257572 A1 | 10/2011 | Locke et al. |
| 2011/0313373 A1 | 12/2011 | Riesinger |
| 2011/0313374 A1 | 12/2011 | Lockwood et al. |
| 2012/0041399 A1 | 2/2012 | Blott et al. |
| 2012/0053538 A1 | 3/2012 | Blott et al. |
| 2012/0130325 A1 | 5/2012 | Blott et al. |
| 2013/0144240 A1 | 6/2013 | Ellis |
| 2013/0165821 A1 | 6/2013 | Freedman et al. |
| 2014/0107595 A1 | 4/2014 | Blott |
| 2014/0371691 A1 | 12/2014 | Blott et al. |
| 2015/0150730 A1 | 6/2015 | Hannigan et al. |
| 2015/0157508 A1 | 6/2015 | Blott et al. |
| 2015/0165182 A1 | 6/2015 | Pratt et al. |
| 2015/0265754 A1 | 9/2015 | Blott et al. |
| 2016/0106892 A1 | 4/2016 | Hartwell |
| 2016/0354535 A1 | 12/2016 | Blott et al. |
| 2017/0007753 A1 | 1/2017 | Blott et al. |
| 2017/0252496 A1 | 9/2017 | Blott et al. |
| 2017/0266356 A1 | 9/2017 | Blott et al. |
| 2017/0274195 A1 | 9/2017 | Blott et al. |
| 2018/0140755 A1 | 5/2018 | Blott et al. |
| 2018/0193200 A1 | 7/2018 | Blott et al. |

(56) References Cited

U.S. PATENT DOCUMENTS

| | | | |
|---|---|---|---|
| 2018/0250450 | A1 | 9/2018 | Blott et al. |
| 2019/0015648 | A1 | 1/2019 | Blott et al. |
| 2019/0046360 | A1 | 2/2019 | Blott et al. |
| 2019/0091385 | A1 | 3/2019 | Blott et al. |
| 2020/0009006 | A1 | 1/2020 | Blott et al. |
| 2020/0022844 | A1 | 1/2020 | Blott et al. |
| 2020/0069851 | A1 | 3/2020 | Blott et al. |

FOREIGN PATENT DOCUMENTS

| | | |
|---|---|---|
| CN | 202069996 | 12/2011 |
| DE | 847475 | 8/1952 |
| DE | 3 539 533 | 5/1987 |
| DE | 3 935 818 | 5/1991 |
| DE | 4 012 232 | 10/1991 |
| DE | 4 102 684 | 8/1992 |
| DE | 197 22 075 | 10/1998 |
| DE | 198 44 355 | 4/2000 |
| DE | 10 2005 014 420 | 9/2006 |
| EP | 0 020 662 | 7/1984 |
| EP | 0 122 085 | 6/1987 |
| EP | 0 298 726 | 1/1989 |
| EP | 0 355 536 | 2/1990 |
| EP | 0 418 607 | 3/1991 |
| EP | 0 425 164 | 5/1991 |
| EP | 0 174 803 B1 | 8/1991 |
| EP | 0 485 657 | 5/1992 |
| EP | 0 521 434 | 1/1993 |
| EP | 0 325 771 | 9/1993 |
| EP | 0 617 938 | 10/1994 |
| EP | 0 638 301 | 2/1995 |
| EP | 0 648 122 | 4/1995 |
| EP | 0 690 736 | 1/1996 |
| EP | 0 724 888 | 8/1996 |
| EP | 0 465 601 | 1/1997 |
| EP | 0 754 064 | 1/1997 |
| EP | 0 762 860 | 3/1997 |
| EP | 0 772 464 | 5/1997 |
| EP | 0 537 559 | 1/1998 |
| EP | 0 620 720 | 3/1998 |
| EP | 0 853 950 | 7/1998 |
| EP | 0 856 318 | 8/1998 |
| EP | 0 858 810 | 8/1998 |
| EP | 0 651 983 | 9/1998 |
| EP | 0 777 504 | 10/1998 |
| EP | 0 876 165 | 11/1998 |
| EP | 0 888 141 | 1/1999 |
| EP | 0 912 251 | 5/1999 |
| EP | 1 007 015 | 6/2000 |
| EP | 1 021 180 | 7/2000 |
| EP | 1 029 585 | 8/2000 |
| EP | 0 688 189 | 9/2000 |
| EP | 1 085 925 | 3/2001 |
| EP | 1 105 110 | 6/2001 |
| EP | 1 105 171 | 6/2001 |
| EP | 1 105 180 | 6/2001 |
| EP | 1 107 813 | 6/2001 |
| EP | 1 030 657 | 10/2001 |
| EP | 1 138 336 | 10/2001 |
| EP | 1 156 839 | 11/2001 |
| EP | 0 564 502 | 1/2002 |
| EP | 0 875 222 | 7/2002 |
| EP | 1 218 437 | 7/2002 |
| EP | 1 306 123 | 5/2003 |
| EP | 1 088 569 | 8/2003 |
| EP | 0 880 953 | 10/2003 |
| EP | 1 219 311 | 7/2004 |
| EP | 1 440 737 | 7/2004 |
| EP | 1 018 967 | 8/2004 |
| EP | 1 488 816 | 12/2004 |
| EP | 1 513 478 | 3/2005 |
| EP | 1 608 032 | 12/2005 |
| EP | 1 614 789 | 1/2006 |
| EP | 1 440 667 | 3/2006 |
| EP | 1 284 777 | 4/2006 |
| EP | 1 772 160 | 4/2007 |
| EP | 2 366 721 | 9/2011 |
| EP | 2 650 028 | 10/2013 |
| EP | 1 742 683 | 2/2016 |
| FR | 1 163 907 | 10/1958 |
| GB | 114754 | 4/1918 |
| GB | 641061 | 8/1950 |
| GB | 1063066 | 3/1967 |
| GB | 1224009 | 3/1971 |
| GB | 1549756 | 8/1979 |
| GB | 2085305 | 1/1985 |
| GB | 2195255 | 4/1988 |
| GB | 2288734 | 11/1995 |
| GB | 2307180 | 5/1997 |
| GB | 2329127 | 3/1999 |
| GB | 2305610 | 7/1999 |
| GB | 2378392 | 2/2003 |
| GB | 2357286 | 11/2003 |
| GB | 2389794 | 12/2003 |
| GB | 2365350 | 8/2004 |
| GB | 2423019 | 8/2006 |
| JP | 59-502014 | 12/1984 |
| JP | S62-279885 | 12/1987 |
| JP | 2001-314479 A | 11/2001 |
| JP | 2001-525688 | 12/2001 |
| JP | 2003-154003 | 5/2003 |
| JP | 2004-121819 | 4/2004 |
| JP | 2012-200425 | 10/2012 |
| SU | 1251912 A1 | 4/1983 |
| WO | WO 1984/01904 | 5/1984 |
| WO | WO 1987/00759 | 2/1987 |
| WO | WO 1990/11795 | 10/1990 |
| WO | WO 1991/00718 | 1/1991 |
| WO | WO 1992/09651 | 6/1992 |
| WO | WO 1992/13713 | 8/1992 |
| WO | WO 1992/19313 | 11/1992 |
| WO | WO 1992/20299 | 11/1992 |
| WO | WO 1993/00056 | 1/1993 |
| WO | WO 1993/06802 | 4/1993 |
| WO | WO 1993/09176 | 5/1993 |
| WO | WO 1993/09727 | 5/1993 |
| WO | WO 1993/24627 | 12/1993 |
| WO | WO 1994/03214 | 2/1994 |
| WO | WO 1994/020133 | 9/1994 |
| WO | WO 1995/03838 | 2/1995 |
| WO | WO 1996/00760 | 1/1996 |
| WO | WO 1996/24316 | 8/1996 |
| WO | WO 1996/40174 | 12/1996 |
| WO | WO 1997/03717 | 2/1997 |
| WO | WO 1997/13520 | 4/1997 |
| WO | WO 1997/33922 | 9/1997 |
| WO | WO 1997/42986 | 11/1997 |
| WO | WO 1997/43991 | 11/1997 |
| WO | WO 1998/06444 | 2/1998 |
| WO | WO 1998/13000 | 4/1998 |
| WO | WO 1998/38955 | 9/1998 |
| WO | WO 1999/01173 | 1/1999 |
| WO | WO 1999/15121 | 4/1999 |
| WO | WO 1999/17698 | 4/1999 |
| WO | WO 1999/23010 | 5/1999 |
| WO | WO 1999/30629 | 6/1999 |
| WO | WO 1999/047097 | 9/1999 |
| WO | WO 1999/48621 | 9/1999 |
| WO | WO 1999/56829 | 11/1999 |
| WO | WO 1999/64081 | 12/1999 |
| WO | WO 1999/65536 | 12/1999 |
| WO | WO 2000/007653 | 2/2000 |
| WO | WO 2000/09199 | 2/2000 |
| WO | WO 2000/38752 | 7/2000 |
| WO | WO 2000/50143 | 8/2000 |
| WO | WO 2000/61206 | 10/2000 |
| WO | WO 2000/62827 | 10/2000 |
| WO | WO 2000/064396 | 11/2000 |
| WO | WO 2001/005443 | 1/2001 |
| WO | WO 2001/016210 | 3/2001 |
| WO | WO 2001/35882 | 5/2001 |
| WO | WO 2001/37773 | 5/2001 |
| WO | WO 2001/041779 | 6/2001 |
| WO | WO 2001/49233 | 7/2001 |

(56) References Cited

FOREIGN PATENT DOCUMENTS

| | | |
|---|---|---|
| WO | WO 2001/062312 | 8/2001 |
| WO | WO 2001/066017 | 9/2001 |
| WO | WO 2001/085248 | 11/2001 |
| WO | WO 2002/000268 | 1/2002 |
| WO | WO 2002/02079 | 1/2002 |
| WO | WO 2002/05737 | 1/2002 |
| WO | WO 2002/09765 | 2/2002 |
| WO | WO 2002/20026 | 3/2002 |
| WO | WO 2002/26180 | 4/2002 |
| WO | WO 2002/034304 | 5/2002 |
| WO | WO 2002/39940 | 5/2002 |
| WO | WO 2002/41878 | 5/2002 |
| WO | WO 2002/45761 | 6/2002 |
| WO | WO 2002/064182 | 8/2002 |
| WO | WO 2002/083046 | 10/2002 |
| WO | WO 2002/091965 | 11/2002 |
| WO | WO 2002/092783 | 11/2002 |
| WO | WO 2002/094256 | 11/2002 |
| WO | WO 2002/102864 | 12/2002 |
| WO | WO 2003/020358 | 3/2003 |
| WO | WO 2003/041686 | 5/2003 |
| WO | WO 2003/063923 | 8/2003 |
| WO | WO 2003/071991 | 9/2003 |
| WO | WO 2003/072748 | 9/2003 |
| WO | WO 2003/074100 | 9/2003 |
| WO | WO 2003/086232 | 10/2003 |
| WO | WO 2003/101385 | 11/2003 |
| WO | WO 2003/101508 | 12/2003 |
| WO | WO 2004/012678 | 2/2004 |
| WO | WO 2004/018020 | 3/2004 |
| WO | WO 2004/024300 | 3/2004 |
| WO | WO 2004/032977 | 4/2004 |
| WO | WO 2004/037334 | 5/2004 |
| WO | WO 2004/045498 | 6/2004 |
| WO | WO 2004/091370 | 10/2004 |
| WO | WO 2005/009225 | 2/2005 |
| WO | WO 2005/009488 | 2/2005 |
| WO | WO 2005/016179 | 2/2005 |
| WO | WO 2005/017000 | 2/2005 |
| WO | WO 2005/018695 | 3/2005 |
| WO | WO 2005/034875 | 4/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/082435 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2005/105180 | 11/2005 |
| WO | WO 2006/014917 | 2/2006 |
| WO | WO 2006/052338 | 5/2006 |
| WO | WO 2006/054323 | 5/2006 |
| WO | WO 2006/099137 | 9/2006 |
| WO | WO 2006/114638 | 11/2006 |
| WO | WO 2006/130594 | 12/2006 |
| WO | WO 2007/075379 | 7/2007 |
| WO | WO 2008/010094 | 1/2008 |
| WO | WO 2008/039839 | 4/2008 |
| WO | WO 2008/040681 | 4/2008 |
| WO | WO 2008/064503 | 6/2008 |
| WO | WO 2008/104609 | 9/2008 |
| WO | WO 2009/011856 | 1/2009 |
| WO | WO 2009/021523 | 2/2009 |
| WO | WO 2009/070905 | 6/2009 |
| WO | WO 2010/016791 | 2/2010 |
| WO | WO 2010/033271 | 3/2010 |
| WO | WO 2010/033574 | 3/2010 |
| WO | WO 2010/033613 | 3/2010 |
| WO | WO 2010/051068 | 5/2010 |
| WO | WO 2010/051073 | 5/2010 |
| WO | WO 2010/072309 | 7/2010 |
| WO | WO 2011/023384 | 3/2011 |

OTHER PUBLICATIONS

Reply of the Patent Proprietor to the Notice(s) of Opposition, re the Opposition of European Patent No. 3 056 241, dated Jan. 27, 2020, in 53 pages.
Consolidated List of Cited Opposition Documents, re European Patent No. EP 3 056 241 dated Sep. 5, 2019, in 1 page.
U.S. Final Office Action, re U.S. Appl. No. 11/577,642, dated Sep. 23, 2009.
U.S. Final Office Action, re U.S. Appl. No. 11/919,354, dated Nov. 24, 2010.
International Preliminary Report on Patentability, re PCT Application No. PCT/GB2005/004177, dated May 1, 2007.
Notice of Opposition—Statement of Facts and Evidence, re European Patent No. EP 3 056 241, dated Sep. 4, 2019, in 32 pages.
Priority Document for GB Application No. 0224986.0, filed Oct. 28, 2002, by Smith & Nephew PLC, in 84 pages.
Priority Document for GB Application No. 0325126.1, filed Oct. 28, 2003, by Smith & Nephew PLC, in 84 pages.
"Hydrocolloids," J. of Wound Care, vol. 1, No. 2, Jul.-Aug. 1992, pp. 27-30.
"Magnitude," The American Heritage Dictionary of the English Language, Fifth Edition, 2011.
Achterberg, V., Ph.D., Hydroactive dressings and serum proteins: an in vitro study, Journal of Wound Care, February, vol. 5, No. 2, 1996, pp. 79-82.
Alexander, J. Wesley, et al., Clinical Evaluation of Epigard, A New Synthetic Substitute for Homograft and Heterograft Skin, The Journal of Trauma, vol. 13, No. 4, 1973, pp. 374-383.
Application for Modification to HCPCS Level II Code Set in the 2005-2006 Coding Cycle. Www.cms.hhs.gov/medicare/hcpcs/.
Aubrey, D.A. et al., "Treatment of the Perineal Wound after Proctectomy by Intermittent Irrigation", Arch. Surg., vol. 119, Oct. 1984, pp. 1141-1144.
Office Action issued from Australian Patent Office on Jun. 4, 2010 for Patent Application No. 2005298433, which is the Australian National Phase application for International Application No. PCT/GB/2005/004177 in 2 pages.
Office Action issued from Australian Patent Office on Oct. 18, 2010 for Patent Application No. 2005298433, which is the Australian National Phase application for International Application No. PCT/GB/2005/004177 in 2 pages.
Bagautdinov, N.A., "Variant of External Vacuum Aspiration in the Treatment of Purulent Diseases of Soft Tissues", in Current Problems in Modern Clinical Surgery: Interdepartmental Collection, edited by V. Ye. Volkov et al. (Chuvash State University, Cheboksary, USSR 1986) pp. 94-96.
Barker et al., "Vacuum Pack Technique of Temporary Abdominal Closure"; J. of Traumatic Injury, Infection, and Critical Care, vol. 48, No. 2 (2000).
Barker, D.E., et al., Vacuum Pack Technique of Temporary Abdominal Closure: A 7-Year Experience with 112 Patients, Journ. of Trauma: Injury and Critical Care, Feb. 2000, 4892), 201-207.
Bevan, D. et al., "Diverse and potent activities of HGF/SF in skin wound repair", Journal of Pathology, vol. 203, 2004, pp. 831-838.
Blumberg, et al., The Effect of Specific Compression on Soft-Tissue Response to Formalinized PVA (Ivalon) Sponge: A Critical Evaluation, Annals Surg., Mar. 1960, 151(3), 409-418.
Boland E.D. et al. Utilizing acid pre-treatment and electrospinning to improve biocompatibility poly(glycolic acid) for tissue engineering. J. Biomed. Mater. Res. Part B: Appl Biomater 71 B 144-152, 2004.
Boland et al., "Tailoring Tissue Engineering Scaffolds Using Electrostatic Processing Techniques: A Study of Poly(Glycolic Acid) Electrospinning" Journal of Macromolecular Science A. Pure and Applied Chemistry, A38(12), 1231-1243 (2001).
Boretos, John W., "Cellular Polymers for Medical Use: The Vital Role of Porosity and Permeability," Cellular Polymers, 1984, vol. 3, pp. 345-358.
Braglina, I.O., et al. "Russian Chemical Bulletin", Dec. 31, 1983.
Brock, W.B., et al., "Temporary closure of open abdominal wounds: the vacuum pack", Am. Surg. Jan. 1995; 61(1)30-5—abstract.

(56) References Cited

OTHER PUBLICATIONS

Chariker, M.E. et al., "Effective Management of Incisional and Cutaneous Fistulae with Closed Suction Wound Drainage", Contemporary Surgery, vol. 34, Jun. 1989, pp. 59-63.

Chernavskii, V. A., B. M. Mirazimov, exerpt from Free Skin Plasty of Wounds and Ulcers using the Vacuum Method, Meditsina Publishers of the Uzbek SSR, Tashkent 1970, pp. 5-37.

Chin, Steven D., et al, "Closed Wound Suction Drainage," The Journal of Foot Surgery, pp. 76-81, vol. 24 No. 1, 1985.

Columbia Electronic Encyclopedia, The: the effect of body temperature on wound healing, printed Jan. 16, 2009, in 3 pages. URL: http://encyclopedia2.thefreedictionary.com/body+temperature.

Dilmaghani et al., "A Method for Closed Irrigation and Suction Therapy in Deep Wound Infections," Journal of Bone and Joint Surgery, 1969, vol. 51-A, No. 2, pp. 323-342.

Fleischmann, W., et al. "Vacuum Sealing for Treatment of Soft Tissue Injury in Open Fractures," Emergency Surgery (1993) 96:488-492.

Garner et al., "Vacuum-assisted wound closure provides early fascial reapproximation in trauma patients with open abdomens," Am. J. of Surgery 1282 (2001) 630-638.

Greene, M. A., et al. Laparotomy Wound Closure with Absorable Polyglycolic Acid Mesh, Surgery, Gynecology and Obsterics 1993; 176: 213-218, Mar. 1993.

Greer, et al., Techniques for Applying Subatmospheric Pressure Dressing to Wounds in Difficult Regions of Anatomy, JWOCN, vol. 26, No. 5, 1999 pp. 250-253.

Grover et al., "Recent Advances: Plastic Surgery," BMJ, 1998, vol. 317, August, www.bmj.com.

Harris, "A new technique of skin grafting using Stei-Greffe and a self-adhering foam pad," Brit. J. of Plastic Surg., vol. 34, No. 2, (Apr. 1981), pp. 181-185.

Hartz, R.S. et al., Healing of the Perineal Wound, Arch. Surg., Apr. 1980, 115, 471-474.

Info V.A.C. User Manual—KCI—Dec. 2006, in 76 pages.

INSTECH Model P720 Peristaltic Pump Operation Manual, Dec. 1997, pp. 1-11.

International Preliminary Report, re PCT Application No. PCT/GB2005/001603, dated Nov. 1, 2006, in 7 pages.

International Search Report, re PCT Application No. PCT/GB2005/001603, dated Jul. 27, 2005, in 4 pages.

Jeter, K. et al., "Managing Draining Wounds and Fistulae: New and Established Methods", Chronic Wound Care, 1990, pp. 240-246.

Karev, I.D., et al., "Foam Drainage System for Treating Purulent Wounds," in Second All-Union Conference "Wounds and Wound Infections" (Presentation Abstracts) (Moscow, USSR 1986) pp. 87-88.

KCI Licensing, "V.A.C. Abdominal Dressing System Advanced Management of the Open Abdomen," 2004.

Kuznetsov, V.A. Bagautdinov, N. A., "Vacuum and Vacuum-Sorption Treatment of Open Septic Wounds," in Second All-Union Conference "Wounds and Wound Infections" (Presentation Abstracts) (Moscow, USSR 1986) pp. 91-92.

Larichev, A.B., "Vacuum Therapy of Wounds and Wound Infection" (First Ed.), BlueSky Publishing, 2005, in 237 pages.

Lokhvitskii, S. V., Treatment of Carbuncles, USSR Ministry of Health, All Union Society of Surgeons and Pirogov Surgical Society, No. 1, January, vol. 132 1984.

Ma, Peter X. Scaffolds for tissue fabrication. Materials Today, Review, May 2004.

Medela, Manualectric Breastpump, *Catalog*, 4 pgs.

Meyer, D. et al., "Weight-Loaded Syringes as a Simple and Cheap Alternative to Pumps for Vacuum-Enhanced Wound Healing", Plastic and Reconstructive Surg., Jun. 2005, 2174-2176 (Correspondence).

Middleton, J., A. Tipton (Mar. 1998). "Synthetic biodegradable polymers as medical devices" (HTML). Medical Plastics and Biomaterials Magazine.

Miller, et al., "Treating a Postoperative, Ischemic Foot Wound Using Bovine Dermal-Derived Extra-cellular Matrix PRIMATRIX™ with The BlueSky Medical Versative 1™ Negative Pressure Wound Therapy System," The Wound Healing Center, Terre Haute, Indiana, Stirling Clinic, Indianapolis, IN.

Mitchell, R. et al., "Role of Stem Cells in Tissue Homeostasis", Pocket Companion to Robbins and Cotran Pathologic Basis of Disease, 7th Edition, 2006.

Morykwas, M. J., et al., "Vacuum-Assisted Closure: A New Method for Wound Control and Treatment: Animal Studies and Basic Foundation," *Annals of Plastic Surgery* 38 (1997) 553-562.

Morykwas, M. J., et al.: "Nonsurgical Modalities to Enhance Healing and Care of Soft Tissue Wounds", Journal of the Southern Orthopaedic Association, vol. 6, No. 4 Winter 1997 in 12 pages.

Navsaria, et al.: "Temporary closure of open abdominal wounds by the modified sandwich-vacuum pack technique", British Journal of Surgery 2003; 90: 718-722.

Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on The Open Abdomen in General Surgery—How Do You Close the Abdomen When You Can't—Boston Marriott Copley Place Hotel, Boston, MA Apr. 26, 2004.

NURSING75, Wound Suction: Better Drainage with Fewer Problems, Nursing, vol. 5, No. 10, Oct. 1975, pp. 52-55.

Orgill, D.P., et al., Guidelines for Treatment of Complex Chest Wounds with Negative Pressure Wound Therapy, *Wounds, A Compendium of Clinical Research and Practice*, Suppl. B, Dec. 2004, 1-23.

Reedy, Justin, "The Science Behind Wound Healing," UW Health Sciences, 2004-2005.

Roberts, R.H., et al., Randomised Trial of Medinorm LVS and Surgivac Drainage System after Operations for Breast Cancer May 1999, *Amer. Journ. Surg., Feb. 1997*, 2 pgs.

Schein et al., "The 'Sandwich Technique' in the Management of the Open Abdomen," British Journal of Surgery, 1986, vol. 73, May, pp. 369-370.

Smith, et al.; Vacuum Pack Technique of Temporary Abdominal Closure: A Four-Year Experience; The American Surgeon; Dec. 1997; p. 1102-1108; vol. 63, No. 12.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Solovev, V.A. "Treatment and Prevention of Suture Failures after Gastric Resection" (Dissertation Abstract) (S.M. Kirov Gorky State Medical Institute, Gorky USSR 1988).

Stewart, J., "World Wide Wounds—Next Generation of Products for Wound Management", 2002, in 13 pages.

Svedman, P., "Irrigation Treatment in Split-Thickness Skin Grafting of Intractable Leg Ulcers," Scand J. Plast. Reconstr. Surg., 19:211-213, 1985.

Svedman, P., "Irrigation Treatment of Leg Ulcers", The Lancet, Sep. 1983, pp. 532-534.

Svedman, P., "A Dressing Allowing Continuous Treatment of a Biosurface", IRCS Med. Science: Biomed. Tech.; Clinic. Med.; Surg. and Transplantation, 1979, 7, p. 221.

Svedman, P. et al., "A Dressing System Providing Fluid Supply and Suction Drainage Used for Continuous or Intermittent Irrigation", Annals of Plastic Surgery, vol. 17, No. 2, Aug. 1986, pp. 125-133.

Swift, et al, "Quorum Sensing in Aeromonas hydrophila and Aeromonas salmonicida: Identification of LuxRI Homologs AhyRI and AsaRI and Their Cognate N-Acylhomoserine Lactone Signal Molecules," J. Bacteriol., 179(17):5271-5281 (1997).

Teder, H. et al., "Continuous Wound Irrigation in the Pig," Journal of Investigative Surgery, vol. 3, 1990, pp. 399-407.

Thomas, Stephen Wound Management and Dressings 35-42 (1990). Translation of Office Action issued from Chinese Patent Office dated Mar. 29, 2009 for Patent Application No. 200580045554.2, which is the Chinese National Phase application for International Application No. PCT/GB2005/004177.

Tribble, D. E., "An Improved Sump Drain-Irrigation Device of Simple Construction", Archives of Surgery New York, vol. 105, Sep. 1972, in 4 pages.

(56) References Cited

OTHER PUBLICATIONS

Urschel, J.D., et al., The Effect of Mechanical Stress on Soft and Hard Tissue Repair; A Review, *Br. Journ. Plast. Surg., 1988*, 41, 182-186.
Vijanto, J. and J. Raekallio, Local Hyperalimentation of Open Wounds, Br. J. surg., 1976, 63, 427-430.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanpek, 1986), Year XI, Zajecar, 1986, No. 3-4, pp. 161-164 (with English translation).
Proprietor's Letter regarding the Opposition Procedure, re European Patent No. 1 742 683, dated Sep. 5, 2018, in 22 pages.

Section Through X-X

Section Through X -X

Section Through X -X

Section Through X-X

Section Through X -X

Section Through X -X

DRESSING AND APPARATUS FOR CLEANSING THE WOUNDS

CROSS-REFERENCE TO RELATED APPLICATIONS

This application is a divisional of U.S. patent application Ser. No. 14/668,774, filed Mar. 25, 2015, which is a continuation of U.S. patent application Ser. No. 13/213,491, filed Aug. 19, 2011, which is a continuation of U.S. patent application Ser. No. 10/599,722, filed Sep. 19, 2008, which is the U.S. national phase application of PCT/GB2005/001603, filed Apr. 27, 2005, which claims priority to Great Britain Patent Application No. 0409446.2, filed Apr. 28, 2004. The disclosure of all of these prior applications are hereby incorporated by references in their entireties.

BACKGROUND OF THE INVENTION

Field of the Invention

The present invention relates to apparatus and a medical wound dressing for aspirating, irrigating and/or cleansing wounds, and a method of treating wounds using such apparatus for aspirating, irrigating and/or cleansing wounds.

It relates in particular to such an apparatus, wound dressing and method that can be easily applied to a wide variety of, but in particular chronic, wounds, to cleanse them of materials that are deleterious to wound healing, whilst distributing materials that are beneficial in some therapeutic aspect, in particular to wound healing.

Description of the Related Art

Aspirating and/or irrigating apparatus are known, and tend to be used to remove wound exudate during wound therapy. In known forms of such wound therapy, aspiration and irrigation of the wound take place sequentially.

Each part of the therapy cycle is beneficial in promoting wound healing:

Aspiration applies a negative pressure to the wound, which is beneficial in itself in promoting wound healing by removing materials deleterious to wound healing with the wound exudate, reducing bacterial load, combating peri-wound oedema, increasing local blood flow to the wound and encouraging the formation of wound bed granulation tissue.

Irrigation cleanses wounds of materials that are deleterious to wound healing by diluting and moving wound exudate (which is typically relatively little fluid and may be of relatively high viscosity and particulate-filled.

Additionally, relatively little of beneficial materials involved in promoting wound healing (such as cytokines, enzymes, growth factors, cell matrix components, biological signalling molecules and other physiologically active components of the exudate) are present in a wound, and are not well distributed in the wound, i.e. they are not necessarily present in parts of the wound bed where they can be potentially of most benefit. These may be distributed by irrigation of the wound and thus aid in promoting wound healing.

The irrigant may additionally contain materials that are potentially or actually beneficial in respect of wound healing, such as nutrients for wound cells to aid proliferation, and gases, such as oxygen. These may be distributed by irrigation of the wound and thus aid in promoting wound healing.

If aspiration and irrigation therapy is applied sequentially to a wound, the two therapies, each of which is beneficial in promoting wound healing, can only be applied intermittently.

Thus, the wound will lose the abovementioned known beneficial effects of aspiration therapy on wound healing, at least in part, while that aspiration is suspended during irrigation.

Additionally, for a given aspirate flow, whilst materials that are potentially or actually deleterious in respect of wound healing are removed from wound exudate, the removal in a given time period of application of the total irrigate and/or aspirate therapy will normally be less effective and/or slower than with continuous application of aspiration.

Even less to be desired, is that while aspiration is not applied to the wound, wound exudate and materials deleterious to wound healing (such as bacteria and debris, and iron II and iron III and for chronic wounds proteases, such as serine proteases) will pool on the wound bed and hinder wound healing, especially in a highly exuding wound. The influx of local oedema will also add to the chronicity of the wound. This is especially the case in chronic wounds.

Depending on the relative volumes of irrigant and wound exudate, the mixed exudate-irrigant fluid and may be of relatively high viscosity and/or particulate-filled. Once it is present and has pooled, it may be more difficult to shift by the application of aspiration in a conventional sequential aspirate—irrigate—dwell cycle than with continuous simultaneous aspiration of the wound, owing to the viscosity and blockage in the system.

The wound will also lose the abovementioned beneficial effects of irrigation therapy on wound healing, at least in part, while that irrigation is suspended during aspiration.

These benefits in promoting wound healing include the movement of materials that are beneficial in promoting wound healing, such as those mentioned above.

Additionally, for a given irrigant flow, the cleansing of the wound and the distribution by irrigation of the wound of such beneficial materials in a given time period of application of the total irrigate and/or aspirate therapy when such therapy is in a conventional sequential aspirate—irrigate—dwell cycle will normally be less effective and/or slower than with continuous application of aspiration.

Such known forms of aspiration and/or irrigation therapy systems also often create a wound environment that may result in the loss of optimum performance of the body's own tissue healing processes, and slow healing and/or in weak new tissue growth that does not have a strong three-dimensional structure adhering well to and growing from the wound bed.

This is a significant disadvantage, in particular in chronic wounds.

The relevant devices tend not to be portable.

It thus would be desirable to provide a system of aspiration and irrigation therapy for a wound, which can remove wound exudate and materials deleterious to wound healing from contact with the wound bed, whilst simultaneously cleansing it and distributing materials that are beneficial in promoting wound healing across it.

SUMMARY OF THE DISCLOSURE

It is an object of the present invention to obviate at least some of the abovementioned disadvantages of known aspiration and/or irrigation therapy systems.

It is a yet further object of the present invention a) to obviate at least some of the abovementioned disadvantages of known aspiration and/or irrigation systems, and b) is portable.

Vascular supply to, and aspiration in, tissue underlying and surrounding the wound is often compromised.

It is a further object of the present invention to provide a system of therapy that also promotes vascular supply to tissue underlying and surrounding a wound, promoting wound healing.

Thus, according to a first aspect of the present invention there is provided an apparatus for aspirating, irrigating and/or cleansing wounds, comprising a) a fluid flow path, comprising a conformable wound dressing, having a backing layer which is capable of forming a relatively fluid-tight seal or closure over a wound and at least one inlet pipe for connection to a fluid supply tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound;

b) a fluid reservoir connected by a fluid supply tube to an inlet pipe via optional means for supply flow regulation;

c) at least one device for moving fluid through the wound dressing; characterised in that it comprises d) means for providing simultaneous aspiration and irrigation of the wound, such that fluid may be supplied to fill the flowpath from the fluid reservoir via the fluid supply tube (optionally via means for supply flow regulation) while fluid is aspirated by a device through the fluid offtake tube (optionally or as necessary via means for aspirate flow regulation).

Where any pipe is described in connection with the apparatus as being connected or for connection to a (mating end of a) tube, e.g. a fluid supply tube or fluid offtake tube, the pipe and the tube may form a single integral unit in the flow path.

The present invention in this aspect provides several advantages.

One is that application of an irrigant to a wound under simultaneous aspiration creates a wound environment that is exposed to the continuous beneficial effects of both aspects of the therapy for wound healing, as opposed to the sequential intermittent application of irrigant flow and aspiration in known aspirating and/or irrigating apparatus. The latter result in less than optimum performance of the body's own tissue healing processes, and slower healing and/or weaker tissue growth that does not have a strong three-dimensional structure adhering well to and growing from the wound bed. This is a significant disadvantage, in particular in chronic wounds.

Thus, the use of the apparatus of this first aspect of the present invention for aspirating, irrigating and/or cleansing wounds retains and enhances the beneficial effects of aspiration in respect of wound healing by continuous and preferably constant aspiration. These include removing materials deleterious to wound healing with the wound exudate, reducing bacterial load, combating peri-wound oedema and encouraging the formation of wound bed granulation tissue.

Preferred embodiments of the apparatus of this first aspect of the present invention for aspirating, irrigating and/or cleansing chronic wounds apply a milder negative pressure than in conventional negative pressure therapy (which is too aggressive for the fragile tissues of many such wounds). This leads to increased patient comfort, and lessens the risk of inflammation of the wound.

The removal of wound exudate in a given time period of application of the total irrigate and/or aspirate therapy will normally be more effective and/or faster than with a conventional sequential intermittent aspiration and/or irrigation therapy.

Even more desirably, since simultaneous aspiration and irrigation is applied to the wound, wound exudate and materials deleterious to wound healing (such as bacteria and debris, and iron II and iron III and for chronic wounds proteases) will not pool on the wound bed and hinder wound healing, especially in a highly exuding wound. This is especially important in chronic wounds.

The resulting mixed exudate-irrigant fluid will usually be of relatively lower viscosity.

Because simultaneous aspiration and irrigation of the wound provides continuous removal at a constant relatively high speed, the fluid does not have to be accelerated cyclically from rest, and will be easier to shift than with known forms of aspiration and/or irrigation therapy systems with a conventional sequential aspirate—irrigate dwell cycle.

This will thus exert a greater net effect on the removal of adherent bacteria and debris.

This is especially the case in those embodiments of the apparatus of this first aspect of the present invention for aspirating, irrigating and/or cleansing wounds where there is an inlet manifold (as described in further detail hereinafter) that covers and contacts most of the wound bed with openings that deliver the fluid directly to the wound bed over an extended area.

The present form of aspiration and/or irrigation therapy systems also often create a wound environment for better distribution of materials that are beneficial in some therapeutic aspect, in particular to wound healing, that are present in a wound, but may not be well distributed in the wound, e.g. in a highly exuding wound (These include cytokines, enzymes, growth factors, cell matrix components, biological signalling molecules and other physiologically active components of the exudate), and or materials contained in the irrigant such as nutrients for wound cells to aid proliferation, and gases, such as oxygen.

These may aid wound cell proliferation and new tissue growth that has a strong three-dimensional structure adhering well to and growing from the wound bed. This is a significant advantage, in particular in chronic wounds.

This is especially the case in those embodiments of the apparatus of this first aspect of the present invention for aspirating, irrigating and/or cleansing wounds where there is an inlet manifold as described below.

This covers and contacts most of the wound bed with openings that deliver the fluid directly to the wound bed over an extended area.

It will be seen that the balance of fluid between fluid aspirated from the wound and irrigant supplied to the wound from the irrigant reservoir may provide a predetermined steady state concentration equilibrium of materials beneficial in promoting wound healing over the wound bed. Simultaneous aspiration of wound fluid and irrigation at a controlled flow rate aids in the attainment and maintenance of this equilibrium The apparatus for irrigating and/or aspirating wounds of the present invention may be used cyclically and/or with reversal of flow.

Preferably the present apparatus for aspirating, irrigating and/or cleansing wounds is a conventionally automated, programmable system which can cleanse the wound with minimal supervision.

The means for providing simultaneous aspiration and irrigation of the wound often comprises
a (first) device for moving fluid through the wound applied to fluid downstream of and away from the wound dressing, in combination with at least one of
a second device for moving fluid through the wound applied to the irrigant in the fluid supply tube upstream of and towards the wound dressing;
means for aspirate flow regulation, connected to a fluid offtake tube, and means for supply flow regulation, connected to a fluid supply tube;

The (first) device will apply negative pressure (i.e. below-atmospheric pressure or vacuum) to the wound bed. It may be applied to the aspirate in the fluid offtake tube downstream of and away from the wound dressing.

Alternatively or additionally, where appropriate, the aspirate in the fluid offtake tube downstream of the wound dressing may be aspirated into a collection vessel, and the first device may act on fluid such as air from the collection vessel.

The (first) device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve.

Alternatively, where appropriate the (first) device for moving fluid through the wound may be a variable-throughput device, such as a variable-speed pump, downstream of the wound dressing, thus effectively forming a combination of a (first) device for moving fluid through the wound with means for aspirate flow regulation and/or means for supply flow regulation in a single integral unit.

The (first) device for moving fluid through the wound will often be a pump of any of the following types, or a piped supply of vacuum, applied to fluid downstream of and away from the wound dressing. In the case of any pump it may be a fixed-speed pump, with (as above) a discrete means for aspirate flow regulation, connected to a fluid offtake tube, and/or means for supply flow regulation, connected to a fluid supply tube, in each case, e.g. a regulator, such as a rotary valve. Alternatively, where appropriate the pump may be a variable-throughput or variable-speed pump.

The following types of pump may be used as the (first) device:
reciprocating pumps, such as piston pumps—where pistons pump fluids through check valves, in particular for positive and/or negative pressure on the wound bed; and
diaphragm pumps—where pulsations of one or two flexible diaphragms displace liquid with check valves.
and
rotary pumps, such as:
progressing cavity
pumps—with a cooperating screw rotor and stator, in particular for higher-viscosity and particulate-filled exudate; and
vacuum pumps—with pressure regulators.

The (first) device may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

Where any second device is applied to the fluid in the fluid supply tube upstream of and towards the wound dressing, it will usually apply positive pressure (i.e. above-atmospheric pressure) to the wound bed.

As with the (first) device, it may be a fixed-throughput device, such as a fixed-speed pump, which will usually require a discrete means for supply flow regulation, connected to a fluid supply tube, e.g. a regulator, such as a rotary valve.

Alternatively, where appropriate the second device for moving irrigant fluid to the wound may be a variable-throughput device, such as a variable-speed pump, upstream of the wound dressing, thus effectively forming a combination of a second device for moving fluid through the wound with means for supply flow regulation in a single integral unit.

The second device for moving fluid through the wound will often be a pump of any of the following types applied to the irrigant in the fluid supply tube upstream of and towards the wound dressing. It may be a fixed-speed pump, with (as above) a discrete means for supply flow regulation, connected to a fluid supply tube, e.g. a regulator, such as a rotary valve. Alternatively, where appropriate the pump may be a variable-throughput or variable-speed pump.

The following types of pump may be used as the second device:
reciprocating pumps, such as
shuttle pumps—with an oscillating shuttle mechanism to move fluids at rates from 2 to 50 ml per minute
and
rotary pumps, such as:
centrifugal pumps
flexible impeller
pumps—where elastomeric impeller traps fluid between impeller blades and a moulded housing that sweeps fluid through the pump housing.
peristaltic pumps—with peripheral rollers on rotor arms acting on a flexible fluid aspiration tube to urge fluid current flow in the tube in the direction of the rotor.
rotary vane pumps—with rotating vaned disk attached to a drive shaft moving fluid without pulsation as it spins. The outlet can be restricted without damaging the pump.

The second device may be a peristaltic pump, e.g. preferably a small portable peristaltic pump. This is a preferred type of pump, in order in particular to reduce or eliminate contact of internal surfaces and moving parts of the pump with irrigant, and for ease of cleaning.

Where the pump is a peristaltic pump, this may be e.g., an Instech Model P720 miniature peristaltic pump, with a flow rate: of 0.2-180 ml/hr and a weight of <0.5 k. This is potentially useful for home and field hospital use.

Each such pump of any these types may also suitably be one that is capable of pulsed, continuous, variable and/or automated and/or programmable fluid movement. Less usually and less preferably, each such pump of any these types will be reversible.

As above, the means for supply flow regulation may be a regulator, such as a rotary valve. This is connected between two parts of a fluid supply tube, such that the desired supply flow regulation is achieved.

If there are two or more inlet pipes, these may be connected to a single fluid supply tube with a single regulator, or to first, second, etc. fluid supply tubes, respectively having a first regulator, a second regulator, etc., e.g. a valve or other control device for admitting fluids into the wound.

As above, the means for aspirate flow regulation may be similarly provided in a form in which concomitant aspirate flow regulation is possible. It may be a regulator, such as a valve or other control device, e.g. a rotary valve.

Multiple offtake tubes may be similarly provided with single or multiple regulators, all for aspiration of fluids from the apparatus, e.g. to a aspirate collection vessel, such as a collection bag.

If there is no second device for moving fluid through the wound applied to the irrigant in the fluid supply tube upstream of and towards the wound dressing, it is only possible to apply a negative pressure to the wound, by means of the device for moving fluid through the wound applied to the aspirate in the fluid offtake tube downstream of and away from the wound dressing.

Operation may e.g. be carried out at a negative pressure of up to 50% atm., typically at a low negative pressure of up to 20% atm., more usually up to 10% atm. at the wound, as is described hereinafter.

Examples of suitable and preferred (first) devices include those types of pump that are so described hereinbefore in relation to the first device. This may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Alternatively, if it is desired to apply a net positive pressure to the wound, the means for providing simultaneous aspiration and irrigation of the wound must comprise not only a first device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Operation may then e.g. be carried out at a positive pressure of up to 50% atm., typically at a low positive pressure of up to 20% atm., more usually up to 10% atm. at the wound, as is described hereinafter.

Examples of suitable and preferred first devices include those types of pump that are so described hereinbefore in relation to the first device. This may be a diaphragm pump, e.g. preferably a small portable diaphragm pump.

This is a preferred type of pump, in order in particular to reduce or eliminate contact of internal surfaces and moving parts of the pump with (chronic) wound exudate, and for ease of cleaning.

Examples of suitable and preferred second devices include those types of pump that are so described hereinbefore in relation to the second device. This may be a peristaltic pump, e.g. a miniature peristaltic pump.

This is a preferred type of pump, in order to eliminate contact of internal surfaces and moving parts of the pump with irrigant in the fluid supply tube upstream of and towards the wound dressing, and for ease of cleaning.

It is of course equally possible to apply a negative pressure to the wound, by means of such a combination of a first device for moving fluid through the wound applied to the aspirate in the fluid offtake tube downstream of and away from the wound dressing, and a second device for moving fluid through the wound applied to the irrigant in the fluid supply tube upstream of and towards the wound dressing; optionally with means for supply flow regulation, connected to a fluid supply tube; means for aspirate flow regulation, connected to a fluid offtake tube.

Indeed, as noted below in this regard, preferred embodiments of the apparatus of this first aspect of the present invention for aspirating, irrigating and/or cleansing chronic wounds that apply a negative pressure include such types of combination of a first device, e.g. a diaphragm pump, e.g. preferably a small portable diaphragm pump, and a second device, e.g. a peristaltic pump, preferably a miniature peristaltic pump, as described hereinbefore in relation to the device for moving fluid through the wound.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integral unit.

The higher end of the ranges of % positive and negative pressure noted above are potentially more suitable for hospital use, where they may only be used safely under professional supervision.

The lower end is potentially more suitable for home use, where relatively high % positive and negative pressures cannot be used safely without professional supervision, or for field hospital use.

In each case, the pressure on the wound may be held constant throughout the desired length of therapy, or may be varied cyclically in a desired positive or negative pressure regime.

As noted above, when it is desired to apply a negative pressure to the wound, it is preferred that the means for providing simultaneous aspiration and irrigation of the wound comprise not only a (first) device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Accordingly, one embodiment of the apparatus for irrigating, cleansing and/or aspirating wounds of the present invention is characterised in the means for providing simultaneous aspiration and irrigation of the wound comprises a (first) device for moving fluid through the wound applied to fluid downstream of and away from the wound dressing, and a second device for moving fluid through the wound applied to the irrigant in the fluid supply tube upstream of and towards the wound dressing, and in combination with at least one of means for supply flow regulation, connected to a fluid supply tube, and means for aspirate flow regulation, connected to a fluid offtake tube.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integral unit.

This combination of a) a device for moving fluid through the wound applied to the aspirate in the fluid offtake tube downstream of and away from the wound dressing, and b) a device for moving fluid through the wound applied to the fluid in the fluid supply tube upstream of and towards the wound dressing, may be used to apply an overall positive or negative, or even zero pressure to the wound.

At least one body in the flow path to, over and from the wound bed should have sufficient resilience against the pressure to allow any significant compression or decompression of the fluid occur.

Thus, examples of suitable bodies include those which are or are defined by a film, sheet or membrane, such as inlet or offtake and/or tubes and structures such as bags, chambers and pouches, filled with irrigant fluid, and e.g. the backing layer of the wound dressing, made of elastically resilient thermoplastic materials.

It will be seen that the balance of fluid between aspirated fluid from the wound and irrigant supplied to the wound from the fluid reservoir will thus be largely determined by a means for providing simultaneous aspiration and irrigation of the wound which is a system comprising:

a) means for aspirate flow regulation and/or a device for moving fluid through the wound applied to fluid downstream of and away from the wound dressing, and b) means for supply flow regulation and/or a device for moving fluid through the wound applied to the fluid in the fluid supply tube upstream of and towards the wound dressing.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integral unit.

The same means may be used to apply an overall positive or negative, or even neutral pressure to the wound.

The appropriate flow rate through the supply tube will depend on a number of factors, such as the viscosity and consistency of each of the irrigant, exudate and mixed exudate-irrigant fluid, and any changes as the wound heals;

the level of negative pressure on the wound bed, whether the irrigant in the fluid supply tube upstream of and into the wound dressing is under positive pressure, and the level of such pressure;

the level of any pressure drop between the irrigant in the fluid supply tube upstream of the wound dressing and the wound bed, such as across a porous element, e.g. a membrane wound contact layer on the lower surface of an inlet manifold that delivers the fluid directly to the wound bed;

means for supply flow regulation; and/or a second device for moving fluid through the wound applied to the fluid in the fluid supply tube upstream of and towards the wound dressing;

the depth and/or capacity of the wound and the power consumption needed for a given desired fluid volume flow rate of irrigant and/or wound exudate through the wound.

The dressing may comprise an inlet manifold (as described in further detail hereinafter) that covers and contacts most of the wound bed with openings that deliver the fluid directly to the wound bed over an extended area, in the form of one or more inflatable hollow bodies defined by a film sheet or membrane.

The (usually small) positive pressure above atmospheric from the irrigation device when both devices are running together should be sufficient to inflate the manifold.

The desired fluid volume flow rate of irrigant and/or wound exudate is preferably that for optimum performance of the wound healing process.

The flow rate will usually be in the range of 1 to 1500 ml/hr, such as 5 to 1000 ml/hr, e.g. 15 to 300 ml/hr, such as 35 to 200 ml/hr through the supply tube. The flow rate through the wound may be held constant throughout the desired length of therapy, or may be varied cyclically in a desired flow rate regime.

In practice, the offtake rate of flow of total irrigant and/or wound exudate will be of the order of 1 to 2000, e.g. 35 to 300 ml/24 hr/cm$^2$, where the cm$^2$ refers to the wound area, depending on whether the wound is in a highly exuding state.

In practice, the rate of exudate flow is only of the order of up to 75 microlitres/cm$^2$/hr (where cm$^2$ refers to the wound area), and the fluid can be highly mobile or not, depending on the level of proteases present). Exudate levels drop and consistency changes as the wound heals, e.g. to a level for the same wound that equates to 12.5-25 microlitres/cm$^2$/hr.

It will be seen that the aspirated fluid from the wound will typically contain a preponderance of irrigant from the fluid reservoir over wound exudate.

The necessary adjustments to maintain the desired balance of fluid by means of a) the means for aspirate flow regulation and/or downstream device, and b) the means for supply flow regulation and/or upstream device for moving fluid will be apparent to the skilled person, bearing in mind that as noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integral unit.

The type and/or capacity of a suitable first device for moving fluid through the wound applied to the aspirate in the fluid offtake tube downstream of and away from the wound dressing and/or a suitable second device for moving fluid through the wound applied to the irrigant in the fluid supply tube upstream of and towards the wound dressing and/or will be largely determined by a) the appropriate or desired fluid volume flow rate of irrigant and/or wound exudate from the wound, and b) whether it is appropriate or desired to apply a positive or negative pressure to the wound bed, and the level of such pressure to the wound bed for optimum performance of the wound healing process, and by factors such as portability, power consumption and isolation from contamination.

As noted above, when it is desired to apply a negative pressure to the wound with the apparatus of this first aspect of the present invention for aspirating, irrigating and/or cleansing wounds to provide simultaneous aspiration and irrigation of the wound, the means for providing simultaneous aspiration and irrigation of the wound may comprise a single device for moving fluid through the wound applied to the aspirate in the fluid offtake tube downstream of and away from the wound dressing or in combination with at least one of means for supply flow regulation, connected to a fluid supply tube, and means for aspirate flow regulation, connected to a fluid offtake tube.

As noted above, the device may be a fixed-throughput device, such as a fixed-speed pump, which will usually require a discrete means for aspirate flow regulation, connected to a fluid offtake tube, e.g. a regulator, such as a rotary valve, or a variable-throughput device, such as a variable-speed pump, downstream of the wound dressing, thus effectively forming a combination of a device for moving fluid through the wound with means for aspirate flow regulation in a single integral unit.

The operation of a typical apparatus of this type for simultaneous aspiration and irrigation of a wound at a low negative pressure of up to 20% atm., more usually up to 10% atm. at the wound, with one pump will now be described.

Before starting the apparatus of this first aspect of the present invention for aspirating, irrigating and/or cleansing wounds, the backing layer of the wound dressing is applied over the wound and conformed to the shape of the bodily part in which the wound is to form a relatively fluid-tight seal or closure.

The means for supply flow regulation, connected to a fluid supply tube, such as a regulator, such as a rotary valve, is usually closed, and the means for aspirate flow regulation (if any), connected to a fluid offtake tube, is opened.

The aspiration pump is started and run to give a negative pressure of up to 50% atm., more usually up to 20% atm., e.g. up to 10% atm. to be applied applies a vacuum to the interior of the dressing and the wound.

The means for fluid supply regulation is opened and is then adjusted, and/or where the aspiration pump is a variable-speed pump, downstream of the wound dressing, that is adjusted, to maintain the desired balance of fluid at a controlled nominal flow rate and to maintain the desired negative pressure in the interior of the wound dressing.

The apparatus is then run for the desired length of therapy and with the desired negative pressure regime.

After this period, the aspiration pump is stopped.

The operation of a typical apparatus for simultaneous aspiration and irrigation of a wound at a low negative pressure of up to 20% atm., more usually up to 10% atm. at the wound, with two pumps will now be described.

The necessary changes where the mode of operation is at a net positive pressure of e.g. up to 15% atm., more usually up to 10% atm. at the wound will be apparent to the skilled person.

Such a typical apparatus for simultaneous aspiration and irrigation of a wound at a low negative pressure of up to 20% atm., more usually up to 10% atm. at the wound comprises means for providing simultaneous aspiration and irrigation of the wound which is a combination of a) a first device for moving fluid through the wound applied to the aspirate in the fluid offtake tube downstream of and away from the wound dressing, with optional means for aspirate flow regulation, connected to a fluid offtake tube: and b) a second device for moving fluid through the wound applied to the irrigant in the fluid supply tube upstream of and towards the wound dressing, with optional means for supply flow regulation, connected to a fluid supply tube.

As noted above, either device may be a fixed-throughput device, such as a fixed-speed pump, which will usually require a discrete means for aspirate flow regulation, connected to a fluid offtake tube, e.g. a regulator, such as a rotary valve, or for irrigant flow regulation, connected to a fluid supply tube, either e.g. a regulator, such as a rotary valve, or a variable-throughput device, such as a variable-speed pump, thus effectively forming a combination of a device for moving fluid through the wound with means for flow regulation in a single integral unit.

Before starting the apparatus of this first aspect of the present invention for aspirating, irrigating and/or cleansing wounds, the backing layer of the wound dressing is applied over the wound and conformed to the shape of the bodily part in which the wound is to form a relatively fluid-tight seal or closure.

Any means for supply flow regulation, connected to a fluid supply tube, such as a regulator, such as a rotary valve, is usually closed, and any means for aspirate flow regulation, connected to a fluid offtake tube, is opened.

The aspiration pump is started and run to apply a negative pressure of up to 50% atm., more usually up to 20% atm., e.g. up to 10% atm., to the interior of the dressing and the wound.

The irrigation pump is then started, so that both pumps are running together, and any means for supply flow regulation is opened.

The irrigation pump flow rate and any means for fluid supply regulation are then adjusted and/or where the aspiration pump and/or the irrigation pump is a variable-speed pump, either or both is/are is adjusted, to maintain the desired balance of fluid at a controlled nominal flow rate and to maintain the desired negative pressure in the interior of the wound dressing.

The apparatus is then run for the desired length of therapy and with the desired pressure regime.

After this period, the irrigation pump is stopped, shortly followed by the aspiration pump.

In all embodiments of the apparatus of this first aspect of the present invention for aspirating, irrigating and/or cleansing wounds, a particular advantage is the tendency of the wound dressing to conform to the shape of the bodily part to which it is applied.

The wound dressing comprises a backing layer with a wound-facing face which is capable of forming a relatively fluid-tight seal or closure over a wound and at least one inlet pipe for connection to a fluid supply tube or tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 20% atm., e.g. up to 10% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof; polysiloxanes; polyesters, such as polycarbonates; polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound.

This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheathes, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheathes, wraps, stockings and hose that are a compressive fit over a limb wound to apply suitable pressure to it when the therapy is applied in this way.

Such means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit.

It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of a fluid tube and/or fluid supply tube (optionally or as necessary via means for forming a tube, pipe or hose, or nozzle, hole, opening, orifice, luer, slot or port for connection as a male member respectively to a mating end of a fluid tube and/or fluid supply tube (optionally or as necessary via means for supply flow regulation) or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer. In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

The wound dressing may not comprise any integer under the backing layer in the wound in use.

However, this may not provide a system to distribute irrigant over a sufficient functional surface area to irrigate the wound at a practical rate to be suitable for use, in particular in chronic wound aspiration and irrigation, with relatively high concentrations of materials that are deleterious to wound healing.

It may be advantageous to provide a system where wound irrigant may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the aspirating fluid directly to the wound bed via the apertures. Similarly, there is an outlet manifold from which tubules radiate and run to the wound bed to end in openings and collect the fluid directly from the wound bed.

The pipes, etc. may radiate regularly or irregularly through the wound in use, respectively from the inlet or outlet manifold, although regularly may be preferred. A more suitable layout for deeper wounds is one in which the pipes, etc. radiate hemispherically and concentrically, to the wound bed.

For shallower wounds, examples of suitable forms of such layout of the pipes, etc. include ones in which the pipes, etc. radiate in a flattened hemiellipsoid and concentrically, to the wound bed.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the aspirating fluid directly to the wound bed or outlet pipe or collects the fluid directly from the wound respectively.

It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound.

Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one which comprises one or more of the tubes, etc in a helix or spiral helix.

Other suitable layouts for shallower wounds include one which have blind-bore, perforated inlet pipe or outlet pipe manifolds that aspirate fluid in the wound when the dressing is in use.

One or both of these may be such a form, the other may be, e.g. one or more straight blind-bore, perforated radial tubes, pipes or nozzles.

A preferred form of inlet pipe (or less usually) outlet pipe manifold that delivers the aspirating fluid directly to the wound bed or collects the fluid directly from the wound respectively is one that comprise one or more conformable hollow bodies defined by a film, sheet or membrane, such as a bag, chamber, pouch or other structure, filled with the irrigant (or less usually) aspirate from the wound, passing through perforations, apertures, holes, openings, orifices, slits or slots in the film, sheet or membrane defining the hollow body or hollow bodies.

These may be of small cross-dimension, so that they may then effectively form microperforations, microapertures or pores in a permeable integer, for example the polymer film, sheet or membrane.

This type of manifold for irrigation (more usually) provides the highest uniformity in the flow distribution of irrigant over the wound at a practical rate to be suitable for use, in particular in chronic wound aspiration and irrigation, and hence to provide a system where materials that are beneficial in promoting wound healing, such as growth factors, cell matrix components, and other physiologically active components of the exudate from a wound, are distributed more evenly under the dressing over the wound bed.

This type of manifold for irrigation (more usually) is noted below with regard to wound fillers under the backing layer, since it is a resiliently flexible, e.g. elastomeric, and soft, structure with good conformability to wound shape. It is urged by its own resilience against the backing layer to apply gentle pressure on the wound bed, and is therefore also capable of acting as a wound filler. The film, sheet or membrane, often has a (generally uniform) thickness similar to that of films or sheets used in conventional wound dressing backing layers.

Another suitable layout is one in which an inlet pipe and/or outlet pipe manifold that delivers the aspirating fluid directly to the wound bed or collects the fluid directly from the wound respectively via inlet and/or outlet tubes, pipes or tubules, and the inlet manifold and/or outlet manifold is formed by slots in layers permanently attached to each other in a stack, and the inlet and/or outlet tubes, pipes or tubules are formed by apertures through layers permanently attached to each other in a stack. (In FIG. 10a there is shown an exploded isometric view of such a stack, which is non-limiting.)

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it, and often with a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the wound bed, and may effectively form a chamber, hollow or cavity defined by a backing layer and the wound bed under the backing layer.

It may be desirable that the interior of the wound dressing conform to the wound bed, even for a wound in a highly exuding state. Accordingly, one form of the dressing is provided with a wound filler under the backing layer.

This is favourably a resiliently flexible, e.g. elastomeric, and preferably soft, structure with good conformability to wound shape.

It is urged by its own resilience against the backing layer to apply gentle pressure on the wound bed.

The wound filler may be integral with the other components of the dressing, in particular the backing layer.

Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

The wound filler may be or comprise a solid integer, favourably a resiliently flexible, e.g. elastomeric, and preferably soft, structure with good conformability to wound shape.

Examples of suitable forms of such wound fillers are foams formed of a suitable material, e.g. a resilient thermoplastic.

Preferred materials for the present wound dressing include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers.

That is, up to 100 micron, preferably up to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials.

Examples also include aerosol foams, where the gaseous phase of the aerosol system is air or an inert gas, such as nitrogen or argon, more usually air, at a small positive pressure above atmospheric; and solid particulates, such as plastics crumbs.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure.

It has apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the aspirating fluid in the apparatus.

The hollow body or each of the hollow bodies then effectively forms an inlet pipe or outlet pipe manifold that delivers the aspirating fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the aspirating fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

The wound filler under the backing layer may effectively form an inlet pipe or outlet pipe manifold, If not, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler is an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that aspirate fluid in the wound when the dressing is in use, that are described hereinbefore, may be used under a wound filler under the backing layer.

In brief, suitable layouts include ones where one or both manifolds are annular or toroidal (regular, e.g. elliptical or circular or irregular), optionally with blind-bore, perforated radial tubes, pipes or nozzles, branching from the annulus or torus; and/or in a meandering, tortuous, winding, zigzag, serpentine or boustrophedic (i.e. in the manner of a ploughed furrow) pattern, or defined by slots in and apertures through layers attached to each other in a stack.

The inlet and/or outlet tubes, the fluid tube and the fluid supply tube, etc. may be of conventional type, e.g. of elliptical or circular cross-section, and may suitably have a uniform cylindrical bore, channel, conduit or passage throughout their length, and suitably the largest cross-dimension of the bore may be up to 10 mm for large torso wounds, and up to 2 mm for limb wounds.

The tube walls should suitably thick enough to withstand any positive or negative pressure on them. However, the prime purpose of such tubes is to convey fluid irrigant and exudate through the length of the apparatus flow path, rather than to act as pressure vessels.

The tube walls may suitably be at least 25 micron thick.

The bore or any perforations, apertures, holes, openings, orifices, slits or slots along the pipes, etc. or in the hollow body or each of the hollow bodies may be of small cross-dimension.

They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

The whole length of the apparatus for aspirating, irrigating and/or cleansing wounds should be microbe-impermeable once the wound dressing is over the wound in use.

It is desirable that the wound dressing and the interior of the apparatus for aspirating, irrigating and/or cleansing wounds of the present invention is sterile.

The fluid may be sterilised in the fluid reservoir and/or the rest of the system in which the fluid moves by ultraviolet, gamma or electron beam irradiation.

This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid moves, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in increased by continuing addition.

Examples of such materials include antibacterial agents (some of which are listed above), and antifungal agents.

Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate, may be added to adjust the pH, as may local analgesics/anaesthetics, such as lidocaine lignocaine/lignocaine hydrochloride, xylocalne (adrenaline, lidocaine) and/or anti-inflammatories, to reduce wound pain or inflammation or pain associated with the dressing.

In order to combat the deposition of materials in the flow path from the irrigant, a repellent coating may be used at any point or on any integer in the path in direct contact with the fluid, e.g. on the means for providing simultaneous aspiration and irrigation of the wound or any desired tube or pipe.

Examples of coating materials for surfaces over which the aspirating fluid passes include anticoagulants, such as heparin, and high surface tension materials, such as PTFE, and polyamides, which are useful for growth factors, enzymes and other proteins and derivatives.

The apparatus of the invention for aspirating, irrigating and/or cleansing wounds is provided with means for admitting fluids directly or indirectly to the wound under the wound dressing in the form of a fluid supply tube to a fluid reservoir.

The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for aspirating, irrigating and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system aspiration and irrigation unit, of the dialysate that moves into the aspirating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, high-density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

Materials deleterious to wound healing that are removed include oxidants, such as free radicals, e.g. peroxide and superoxide; iron II and iron III;

all involved in oxidative stress on the wound bed;

proteases, such as serine proteases, e.g. elastase and thrombin; cysteine proteases; matrix metalloproteases, e.g. collagenase; and carboxyl (acid) proteases;

endotoxins, such as lipopolysaccharides;

autoinducer signalling molecules, such as homoserine lactone derivatives, e.g. oxo-alkyl derivatives;

inhibitors of angiogenesis such as thrombospondin-1 (TSP-1), plasminogen activator inhibitor, or angiostatin (plasminogen fragment); pro-inflammatory cytokines such as tumour necrosis factor alpha (TNFα) and interleukin 1 beta (IL-1β), oxidants, such as free radicals, e.g., e.g. peroxide and superoxide; and metal ions, e.g. iron II and iron III, all involved in oxidative stress on the wound bed.

It is believed that aspirating wound fluid aids in removal from of the materials deleterious to wound healing from wound exudate and/or irrigant, whilst distributing materials that are beneficial in promoting wound healing in contact with the wound.

A steady state concentration equilibrium of materials beneficial in promoting wound healing may be set up between in the irrigant and/or wound exudate.

Aspirating wound fluid aids in the quicker attainment of this equilibrium

Materials beneficial to wound healing that are distributed include cytokines, enzymes, growth factors, cell matrix components, biological signalling molecules and other physiologically active components of the exudate and/or materials in the irrigant that are potentially or actually beneficial in respect of wound healing, such as nutrients for wound cells to aid proliferation, gases, such as oxygen.

The conduits through which respectively the irrigant and/or wound exudate passes to and from the wound dressing and i) may have means for modular disconnection and withdrawal of the dressing, ii) providing an immediate fluid-tight seal or closure over the ends of the conduits and the cooperating tubes in the rest of the apparatus of the invention so exposed, to prevent continuing passage of irrigant and/or exudate.

The outlet from the means for aspirate flow regulation and/or tubes may be collected and monitored and used to diagnose the status of the wound and/or its exudate.

Any aspirate collection vessel may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the aspirate collection vessel will be largely determined by its function.

To be suitable for use, the material need only be fluid-impermeable once in use, and flexible.

Examples of suitable materials for the fluid reservoir include synthetic polymeric materials, such as polyolefins, such as poly(vinylidene chloride).

Suitable materials for the present purpose also include polyethylene, e.g. high-density polyethylene, polypropylene, copolymers thereof, for example with vinyl acetate and mixtures thereof.

In a second aspect of the present invention there is provided a conformable wound dressing, characterised in that it comprises a backing layer with a wound-facing face which is capable of forming a relatively fluid-tight seal or closure over a wound and has at least one inlet pipe for connection to a fluid supply tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound.

The dressing is advantageously provided for use in a bacteria-proof pouch.

Examples of suitable forms of such wound dressings are as described by way of example hereinbefore.

In a third aspect of the present invention there is provided a method of treating wounds to promote wound healing using the apparatus for aspirating, irrigating and/or cleansing wounds of the present invention.

BRIEF DESCRIPTION OF THE DRAWINGS

The present invention will now be described by way of example only with reference to the accompanying drawings in which:

In these, FIG. 3A is a cross-sectional plan view of the wound dressing, and FIG. 3B is a cross-sectional side view of the wound dressing.

FIGS. 10A-C are various views of inlet and outlet manifold layouts for the wound dressings of the second aspect of the present invention for respectively delivering fluid to, and collecting fluid from, the wound.

a filter downstream of the aspirate collection vessel, and a bleed regulator, such as a rotary valve, connected to the fluid offtake tube or to the wound space, for the regulation of the positive or negative pressure applied to the wound.

Figure 11A:
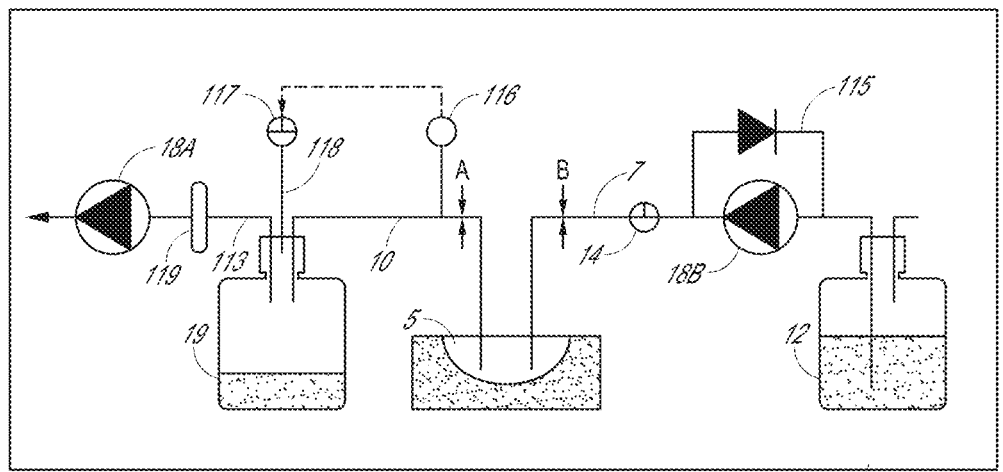
FIGS. 11A to D are variants of a two-pump system with essentially identical, and identically numbered, components as in FIG. 2, except that there is a pump bypass loop, except in FIG. 11C.
Figure 11B:
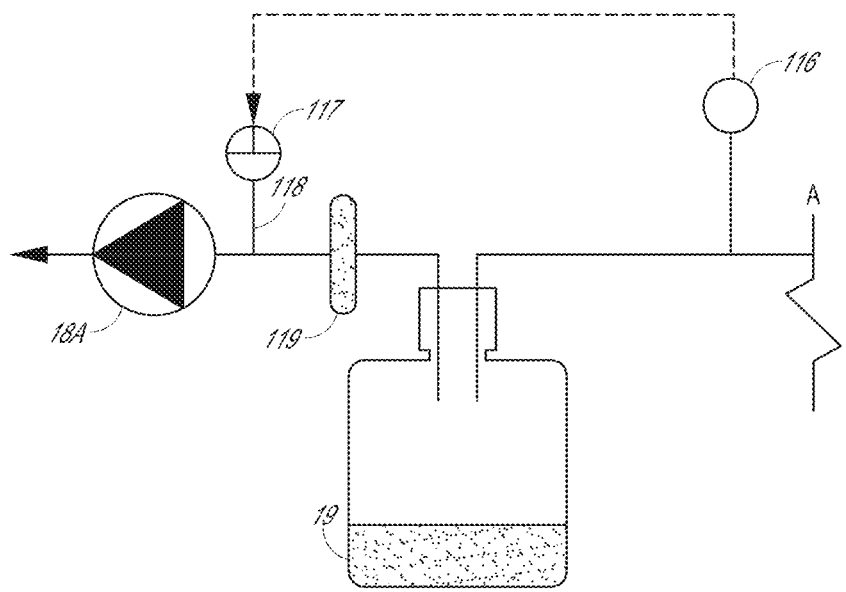
Figure 11C:
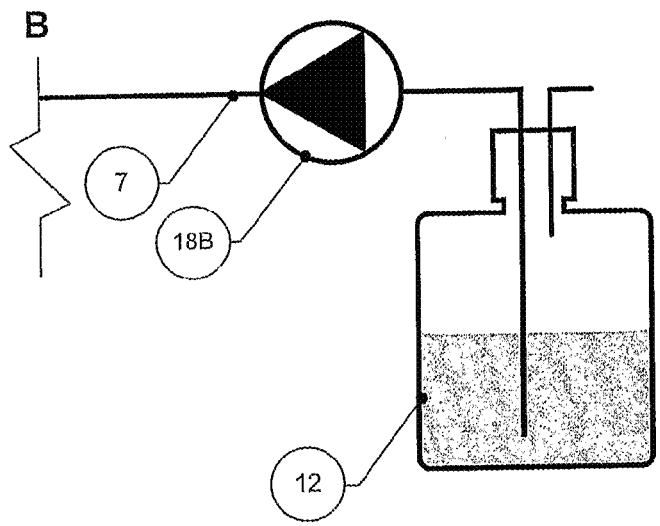
Figure 11D:
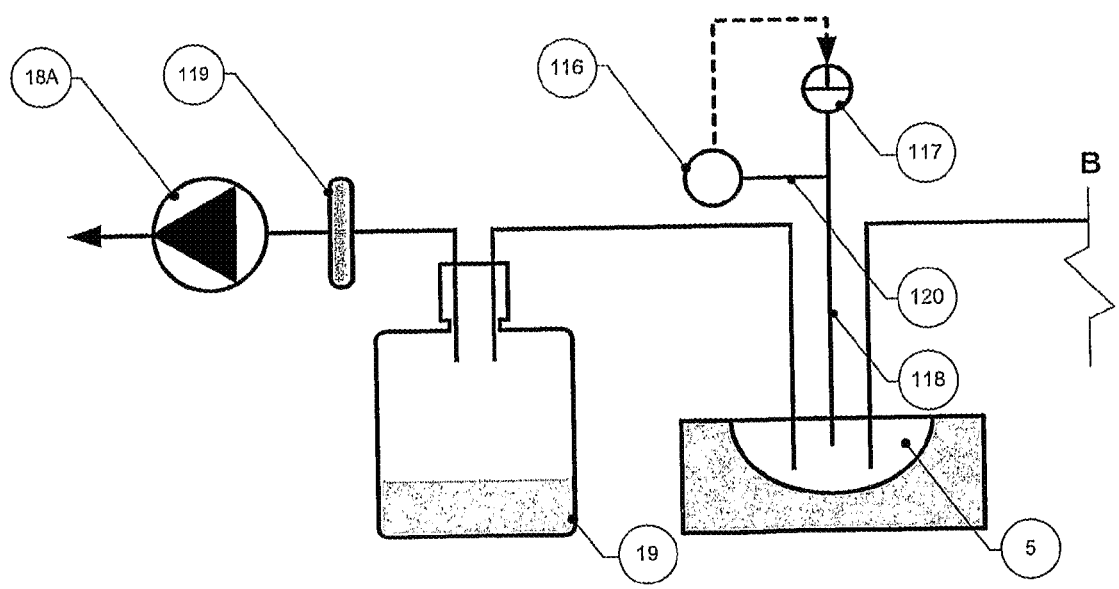
Figure 12A:
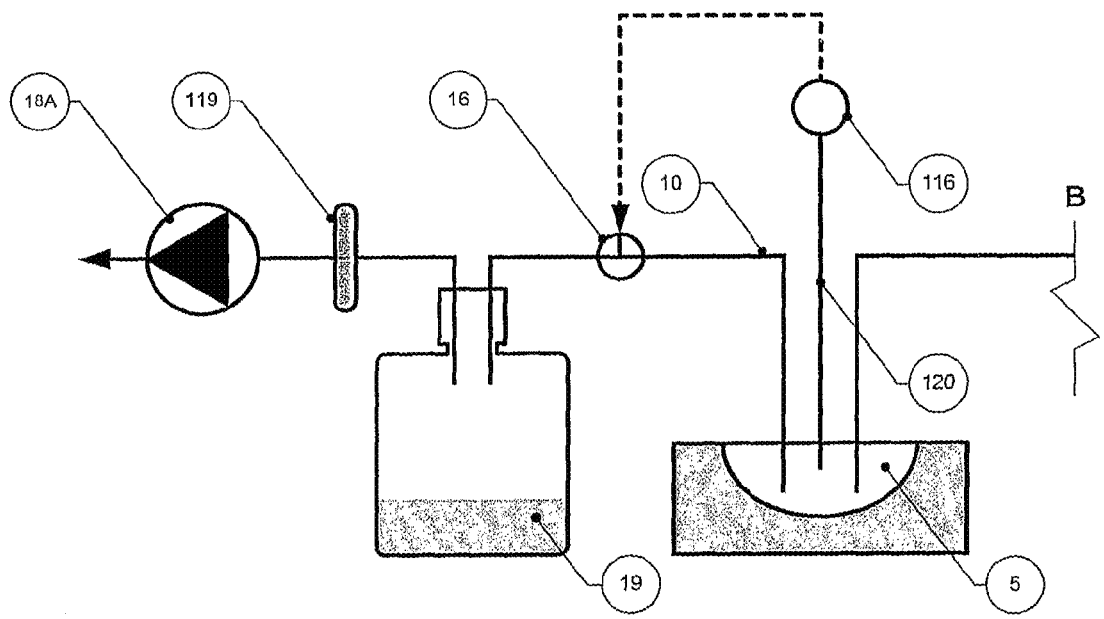
Figure 12B:
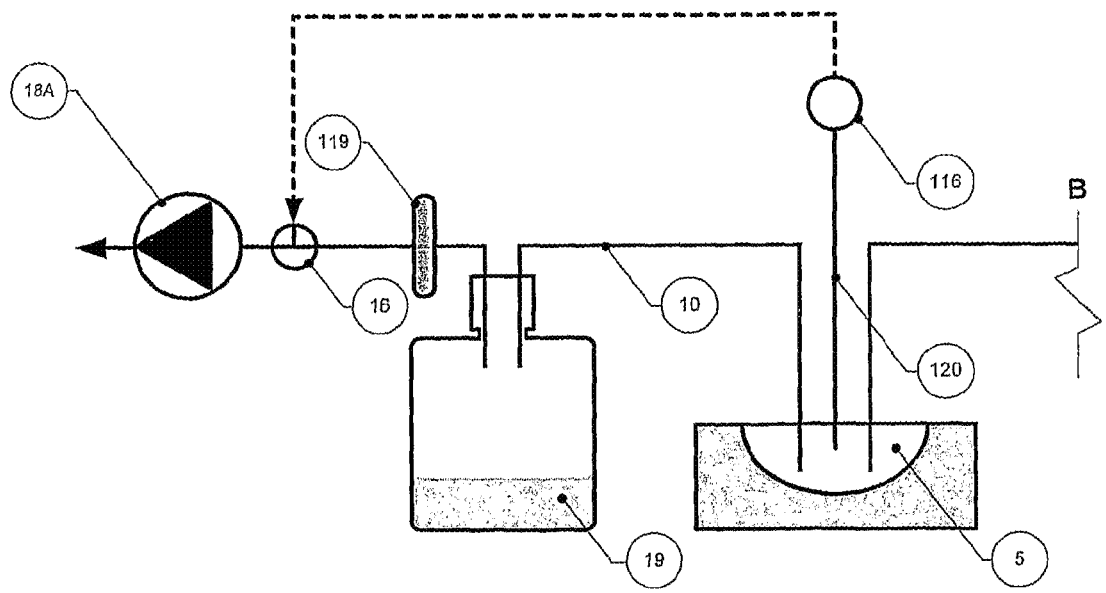
Figure 12C:
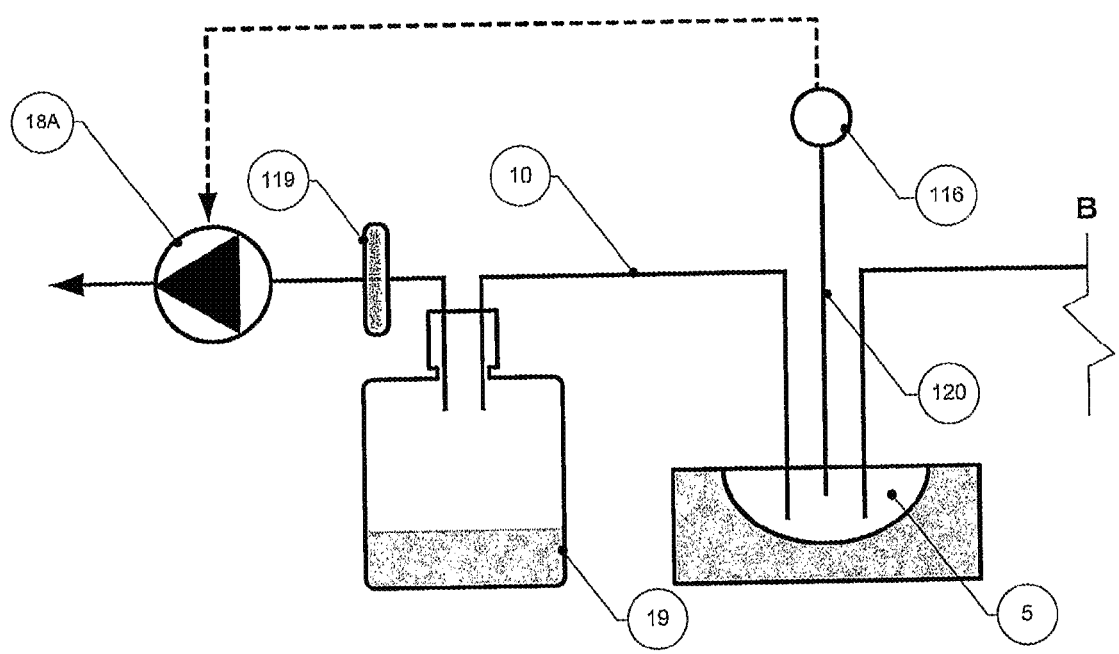

FIGS. 12A to C are variants of a two-pump system with essentially identical, and identically numbered, components as in FIG. 11, except that they have various means for varying the regulation of the positive or negative pressure applied to the wound.

Figure 13A:
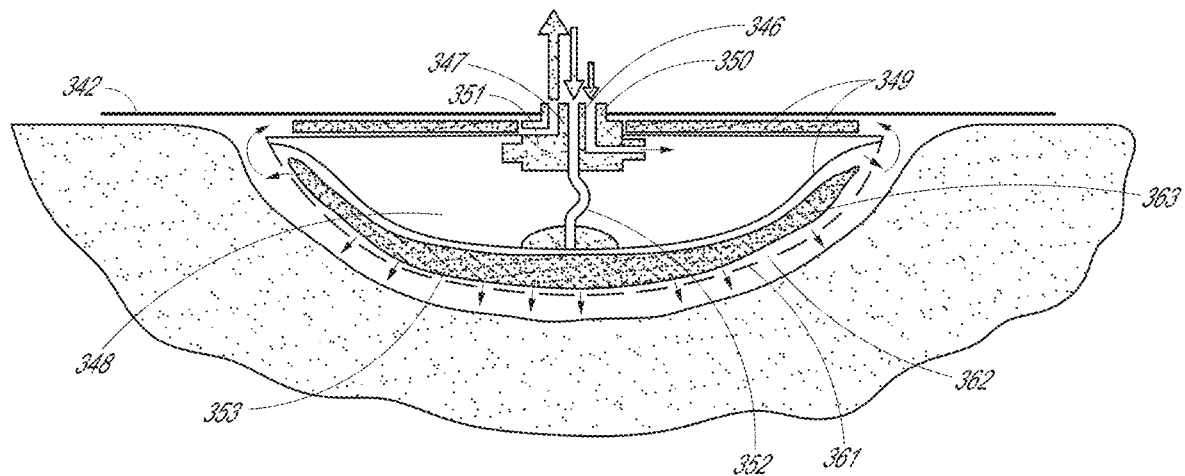
Figure 13B:
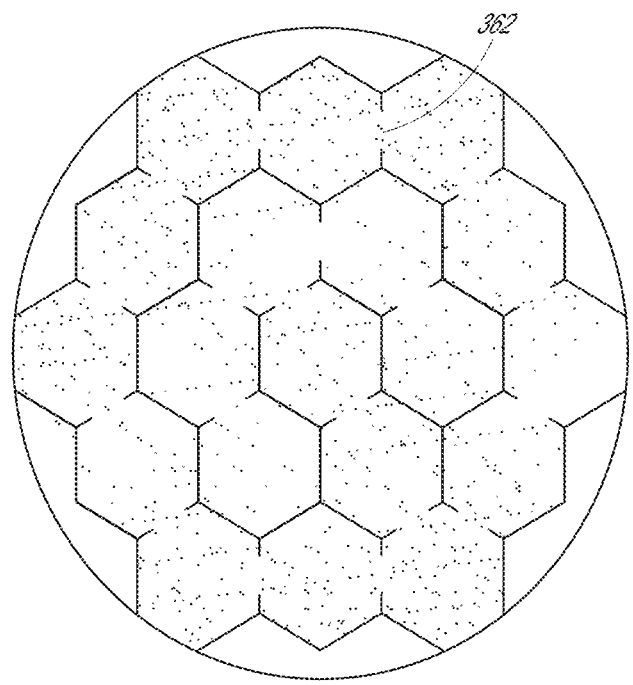

FIGS. 13A-B are cross-sectional views of conformable wound dressings, of the second aspect of the present invention for aspirating and/or irrigating wounds.

Figure 14:
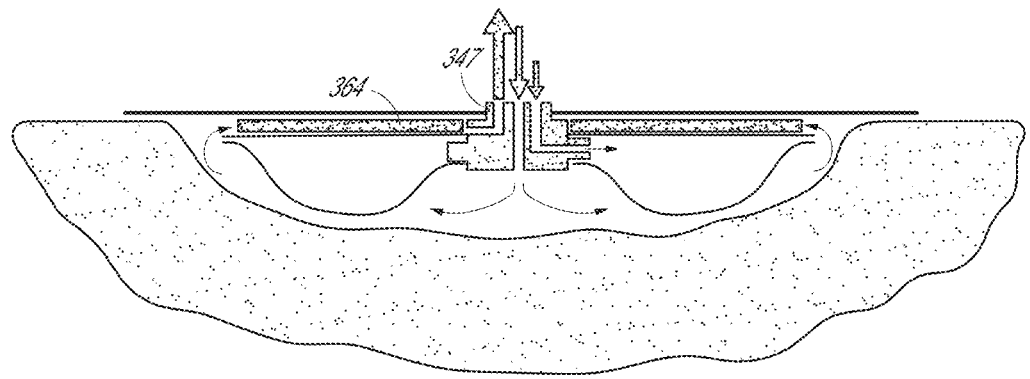

FIG. 14 is a cross-sectional view of a conformable wound dressing, of the second aspect of the present invention for aspirating and/or irrigating wounds.

Figure 15:
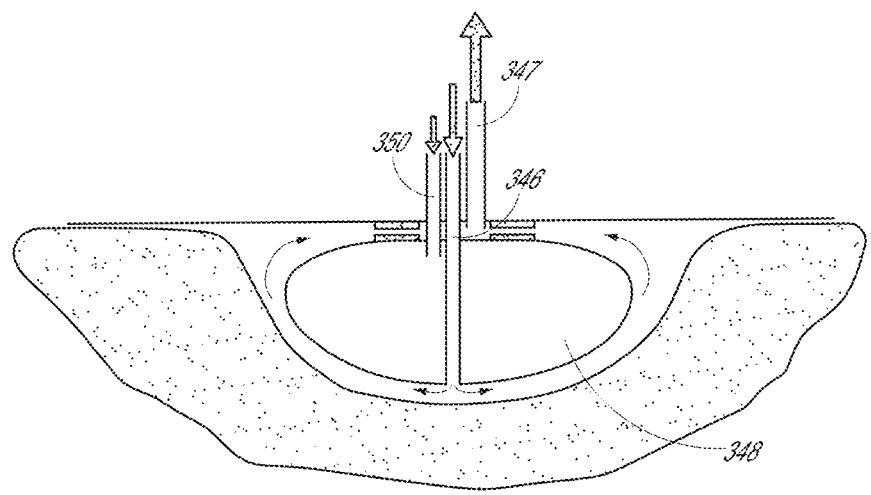

FIG. 15 is a cross-sectional view of a conformable wound dressing, of the second aspect of the present invention for aspirating and/or irrigating wounds.

Figure 16A:
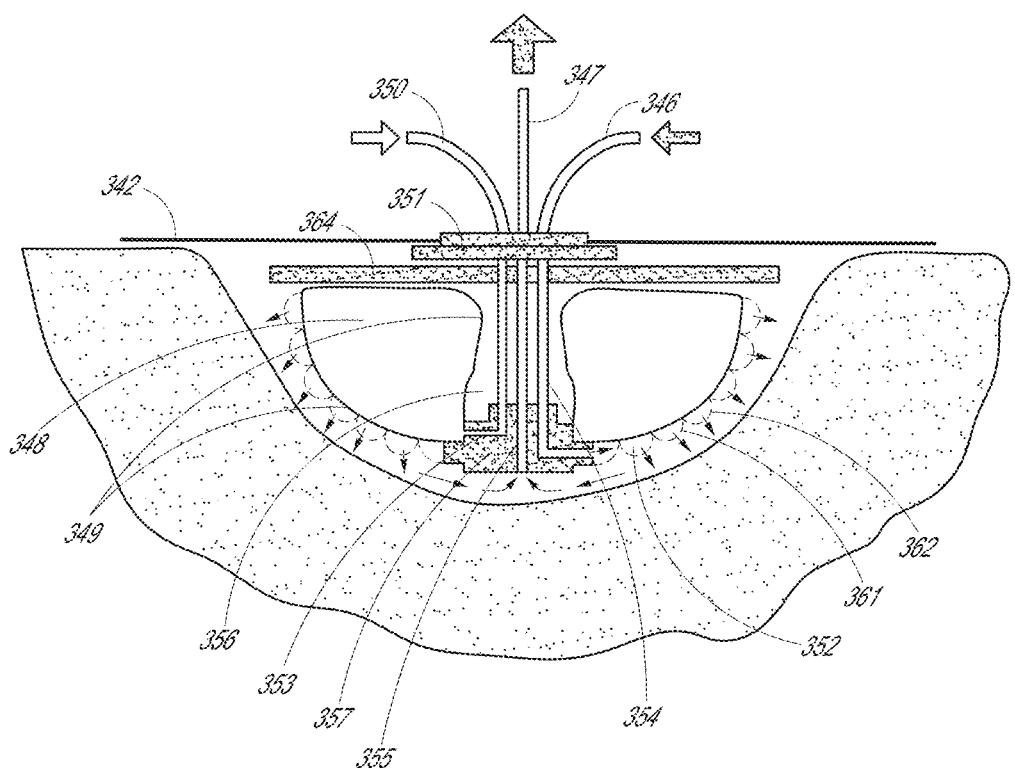
Figure 16B:
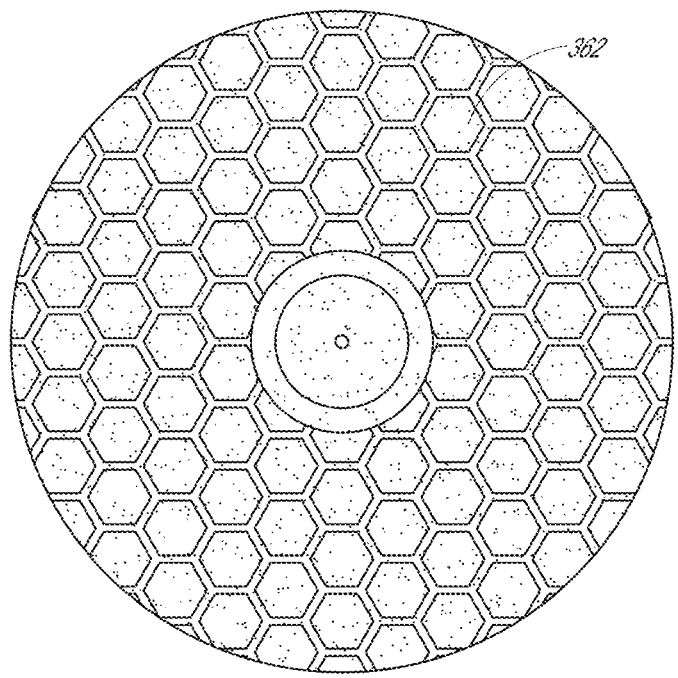

FIGS. 16A-B are cross-sectional views of conformable wound dressings, of the second aspect of the present invention for aspirating and/or irrigating wounds.

Figure 17:
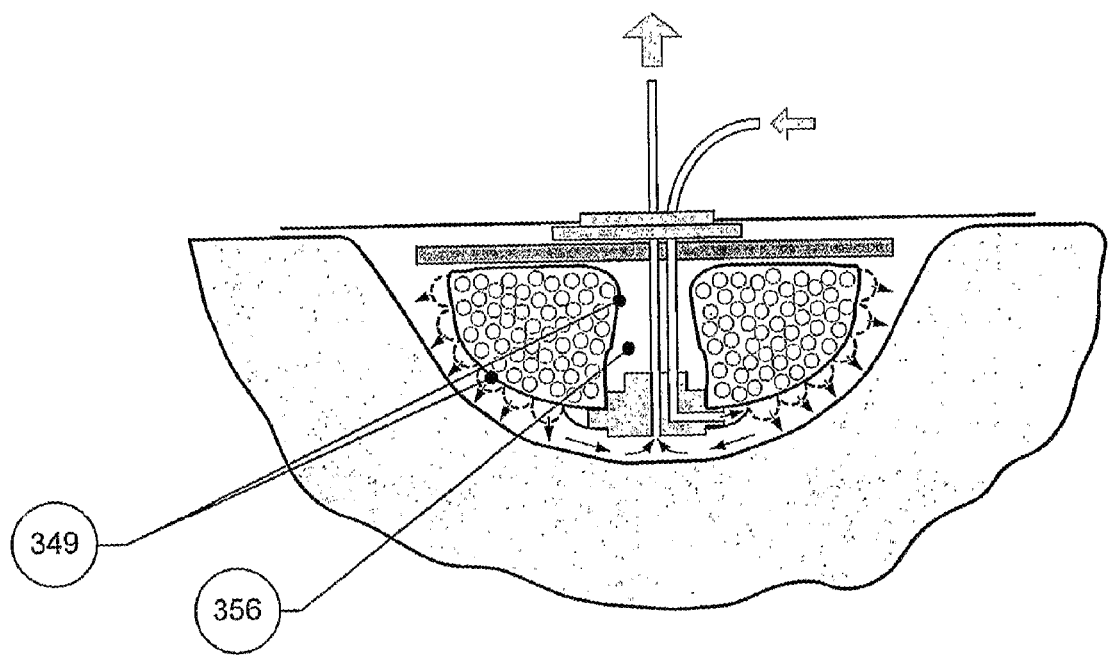

FIG. 17 is a cross-sectional view of a conformable wound dressings, of the second aspect of the present invention for aspirating and/or irrigating wounds.

Figure 18A:
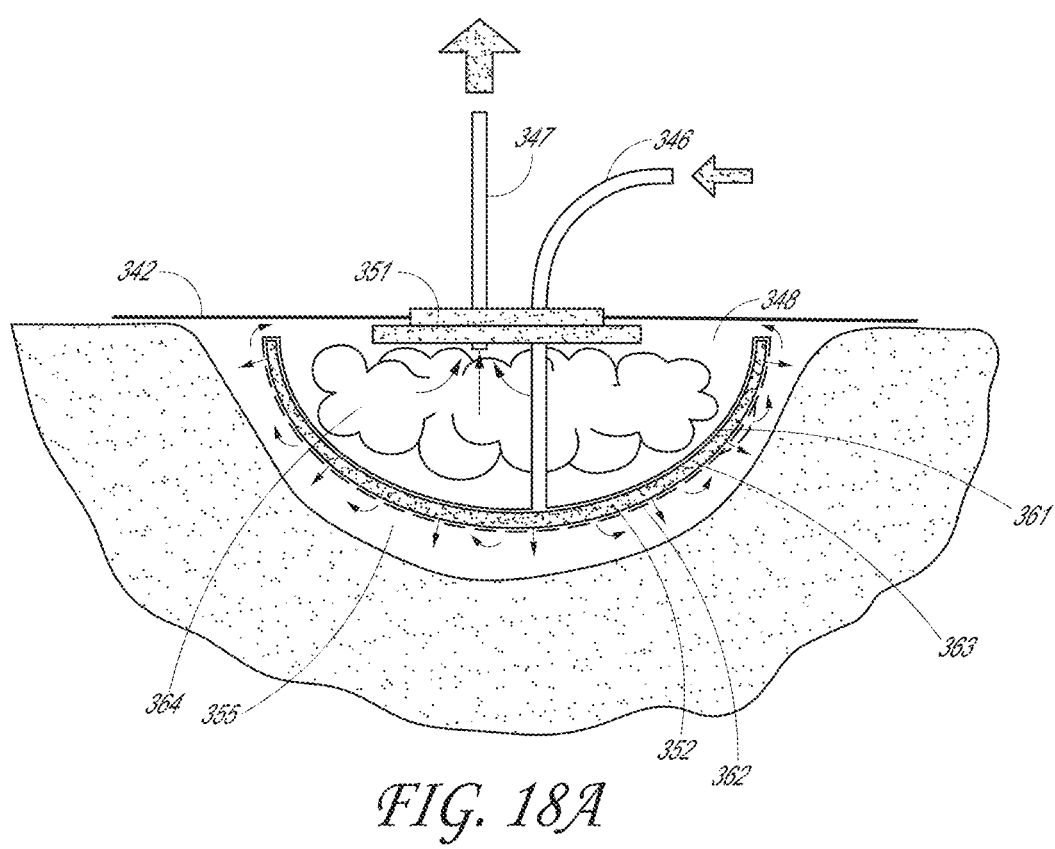
Figure 18B:
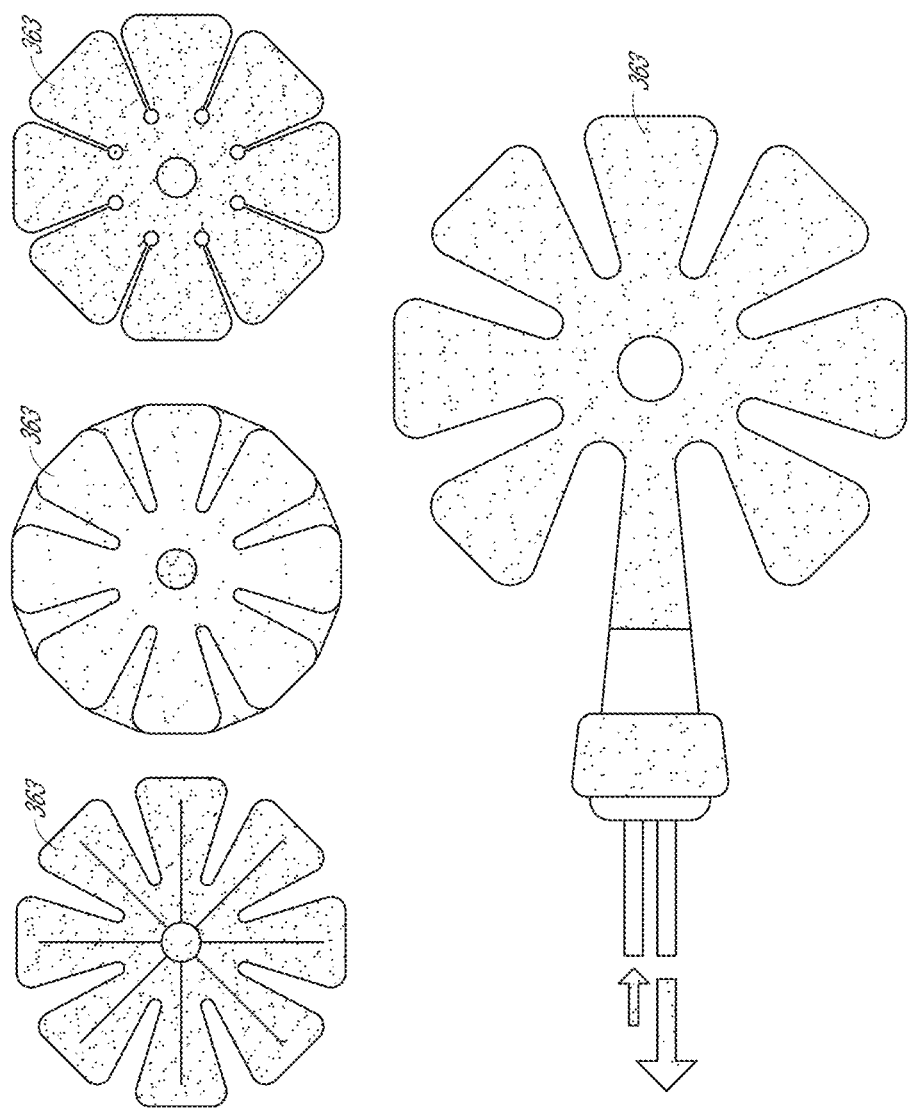

FIG. 18A-B are cross-sectional views of conformable wound dressings, of the second aspect of the present invention for aspirating and/or irrigating wounds.

Figure 19:
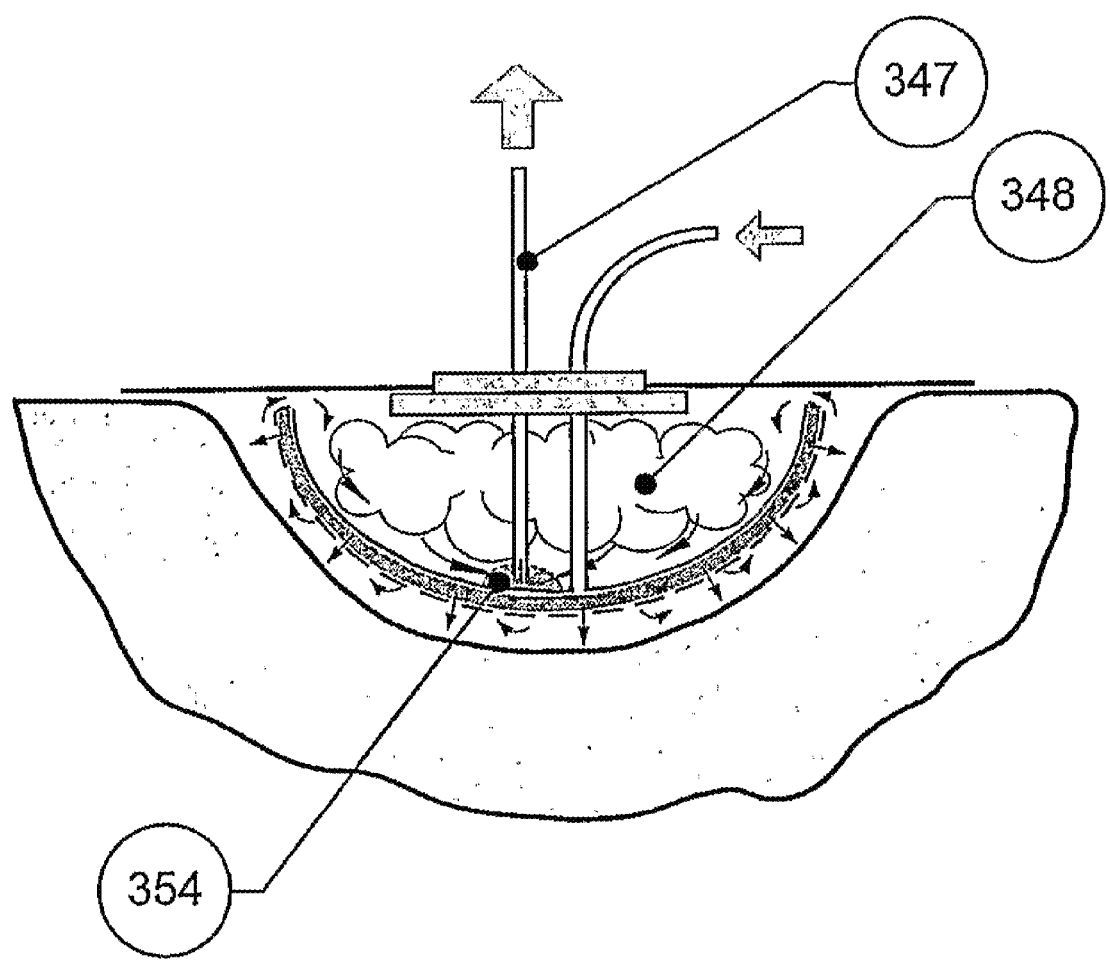

FIG. 19 is a cross-sectional view of a conformable wound dressing, of the second aspect of the present invention for aspirating and/or irrigating wounds.

Figure 20:
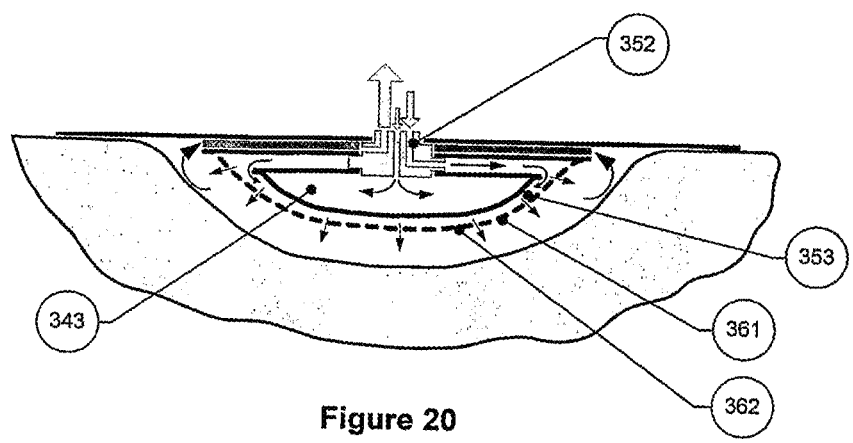

FIG. 20 is a cross-sectional view of a conformable wound dressing, of the second aspect of the present invention for aspirating and/or irrigating wounds.

Figure 21:
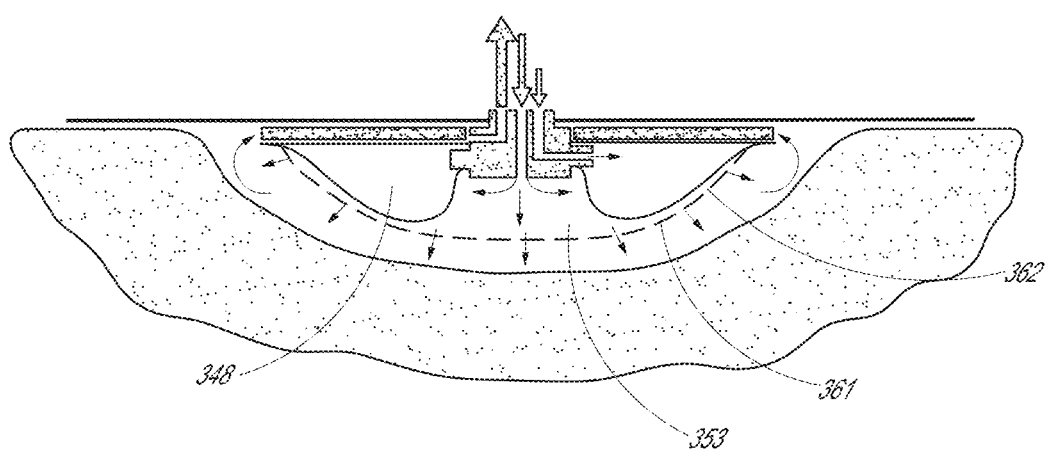

FIG. 21 is a cross-sectional view of a conformable wound dressing, of the second aspect of the present invention for aspirating and/or irrigating wounds.

Figure 22:
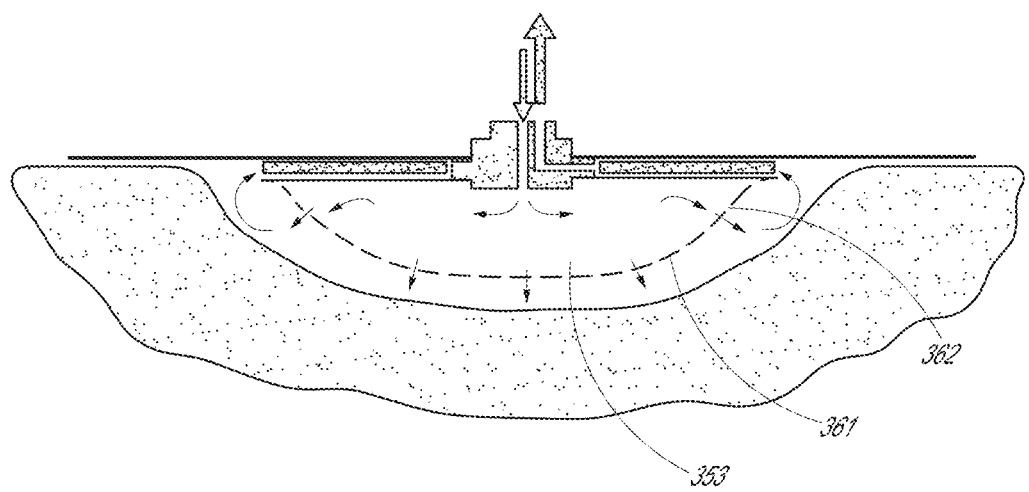

FIG. 22 is a cross-sectional view of a conformable wound dressing, of the second aspect of the present invention for aspirating and/or irrigating wounds.

Figure 23:
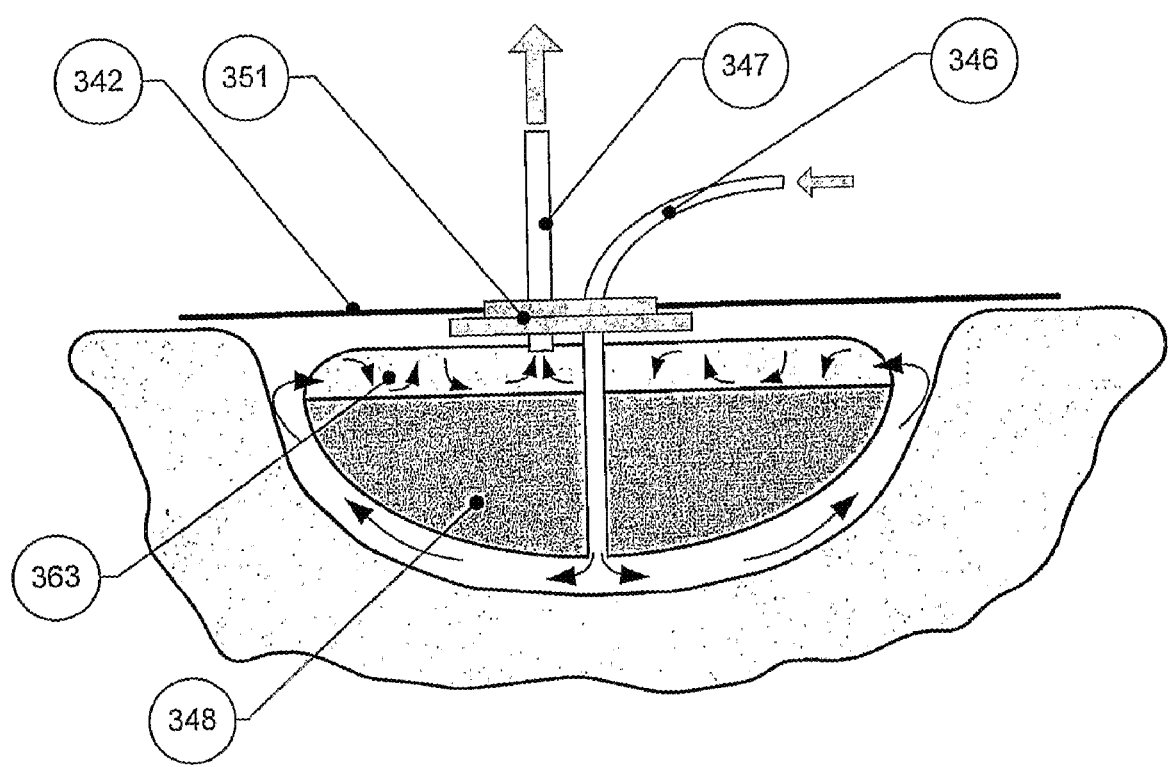

FIG. 23 is a cross-sectional view of a conformable wound dressing, of the second aspect of the present invention for aspirating and/or irrigating wounds.

Figure 24:
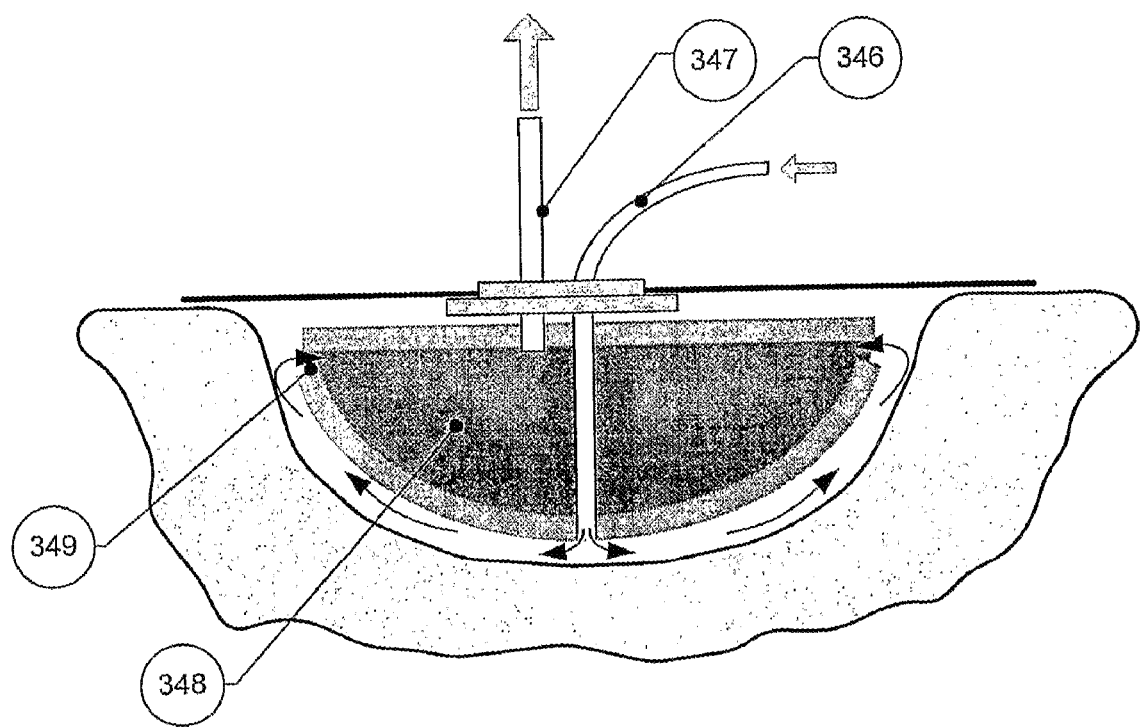

FIG. 24 is a cross-sectional view of a conformable wound dressing, of the second aspect of the present invention for aspirating and/or irrigating wounds.

Figure 25:
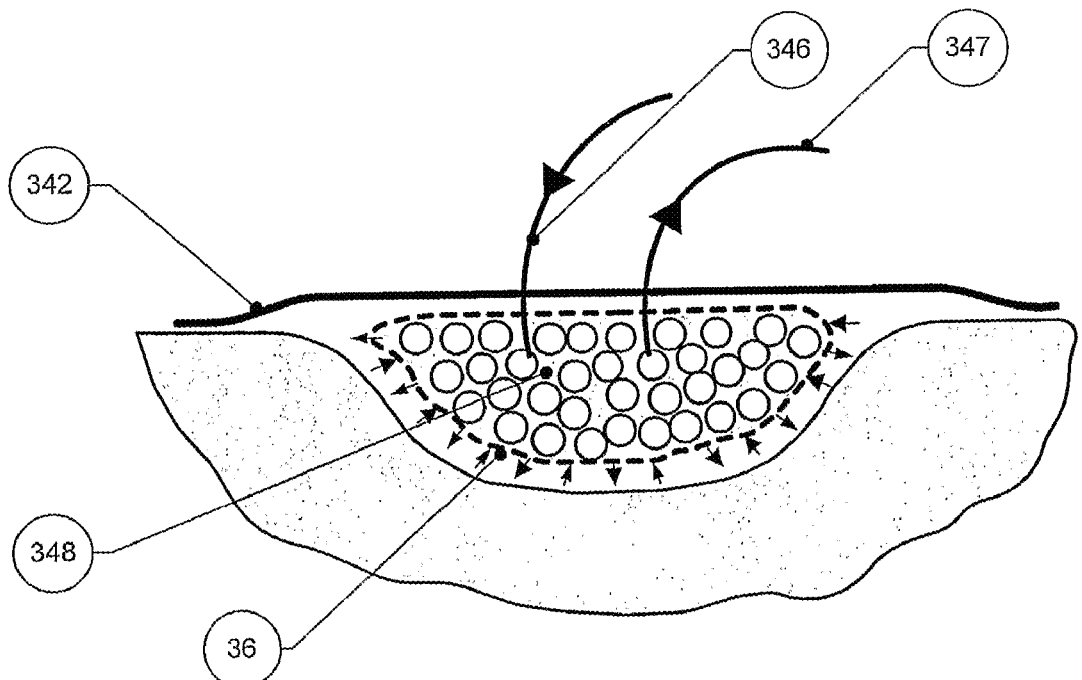

FIG. 25 is a cross-sectional view of a conformable wound dressing, of the second aspect of the present invention for aspirating and/or irrigating wounds.

Figure 26:
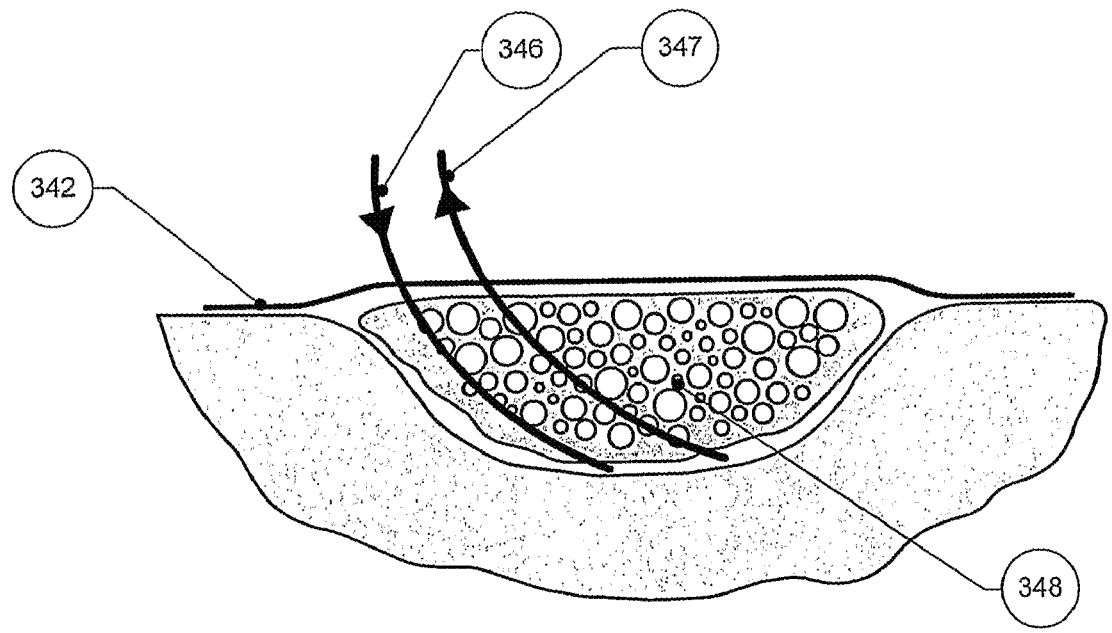

FIG. 26 is a cross-sectional view of a conformable wound dressing, of the second aspect of the present invention for aspirating and/or irrigating wounds.

Figure 27A:
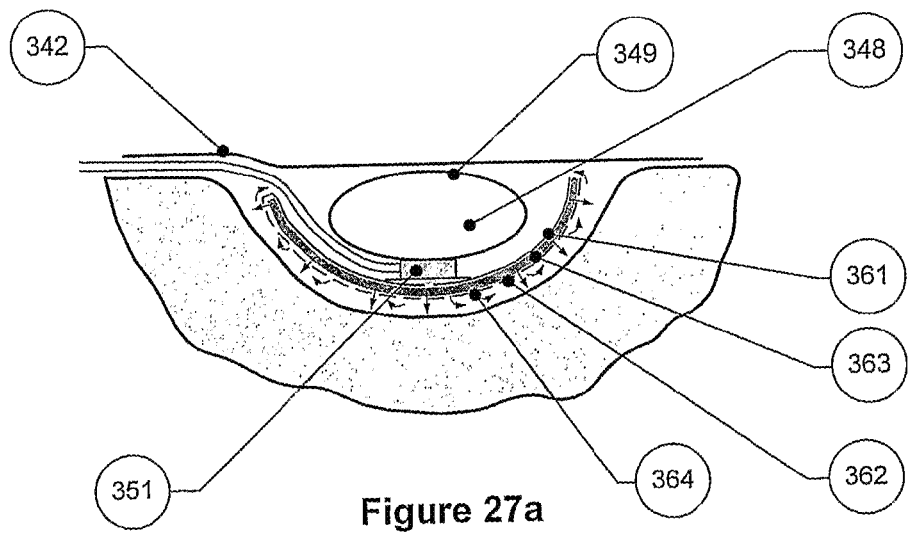
Figure 27B:
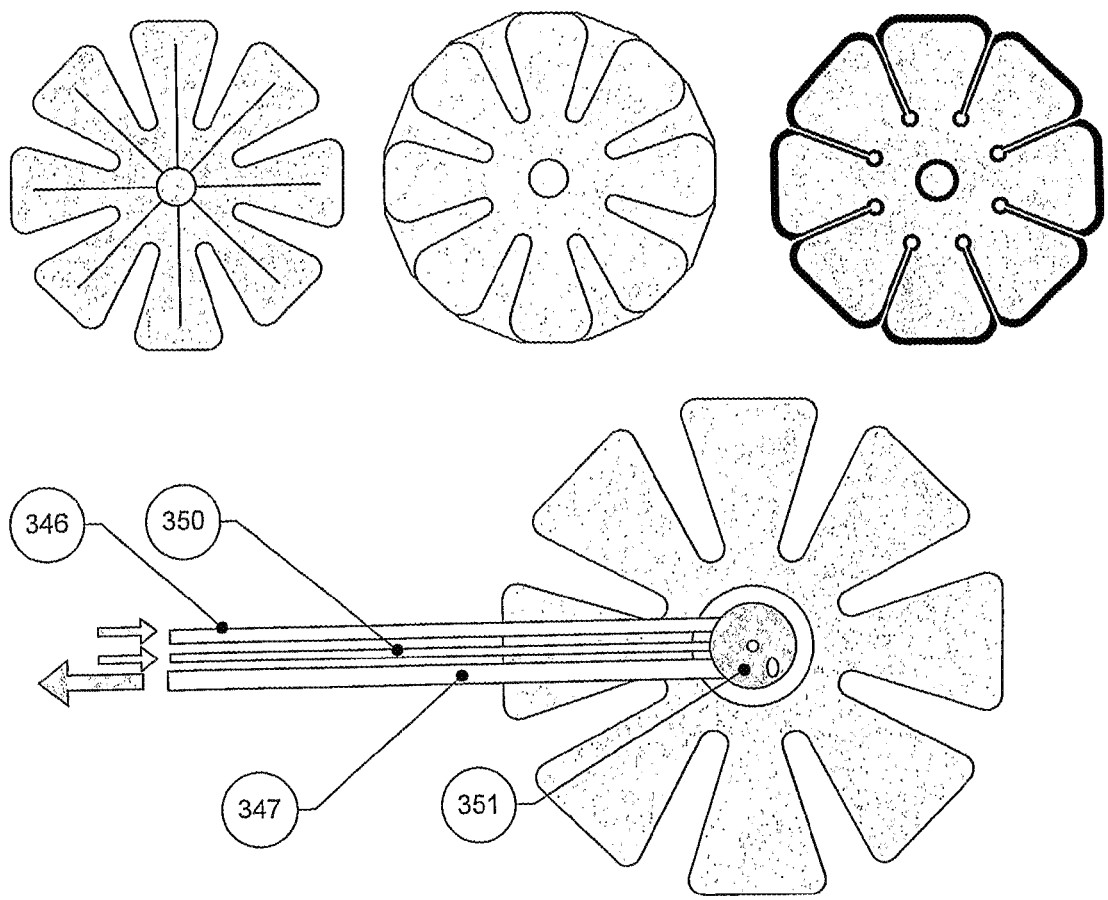

FIG. 27A is a plan view and FIG. 27B a cross-sectional view of a further conformable wound dressings of the second aspect of the present invention for aspirating and/or irrigating wounds.

Figure 28A:
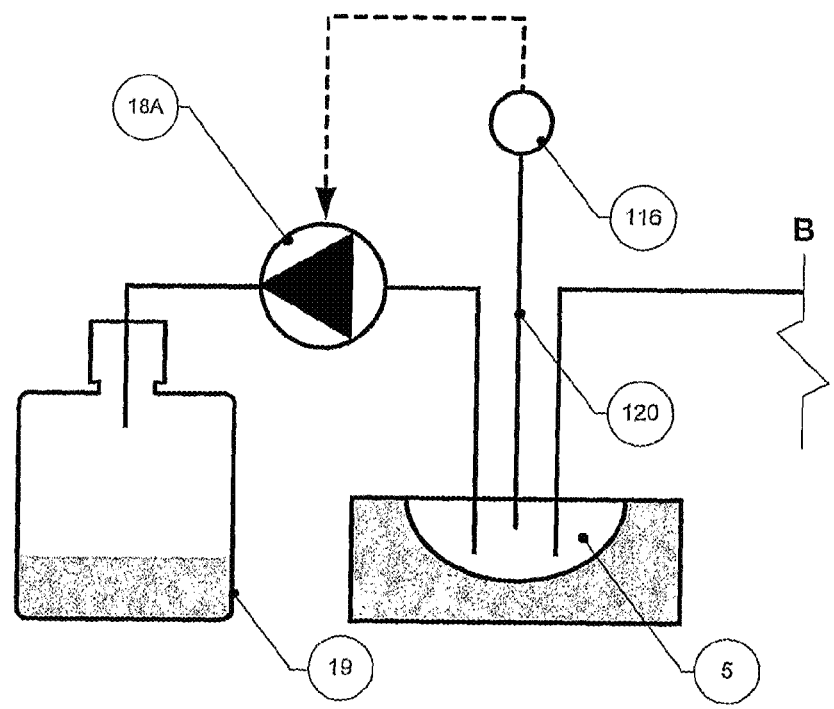

FIGS. 28A and B are variants of a two-pump system with essentially identical, and identically numbered, components as in FIG. 11.

However, they have alternative means for handling the aspirate flow to the aspirate collection vessel under negative or positive pressure to the wound in simultaneous aspiration and irrigation of the wound, including in FIG. 27B a third device for moving fluid into a waste bag.

Figure 29:
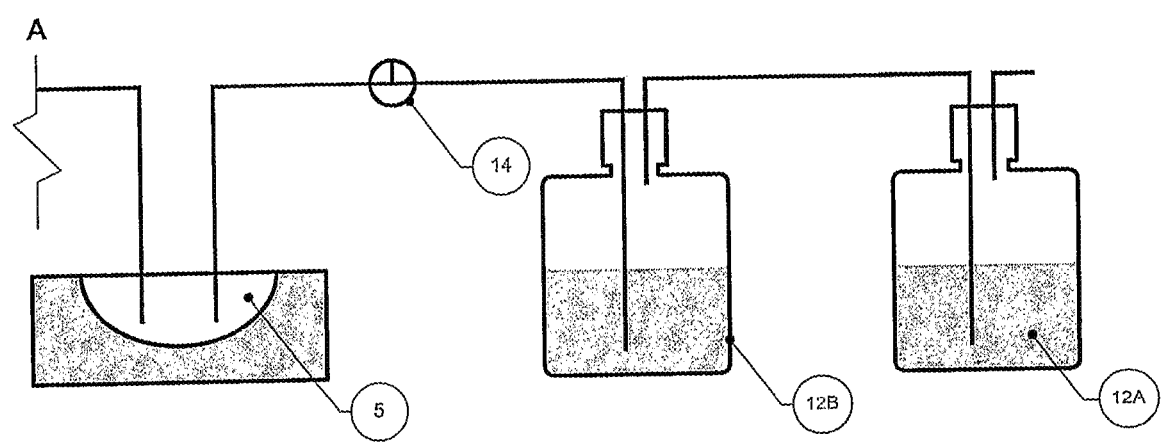

FIG. 29 is a single-pump system essentially with the omission from the apparatus of FIG. 11 of the second device for moving irrigant fluid into the wound dressing.

Figure 30:
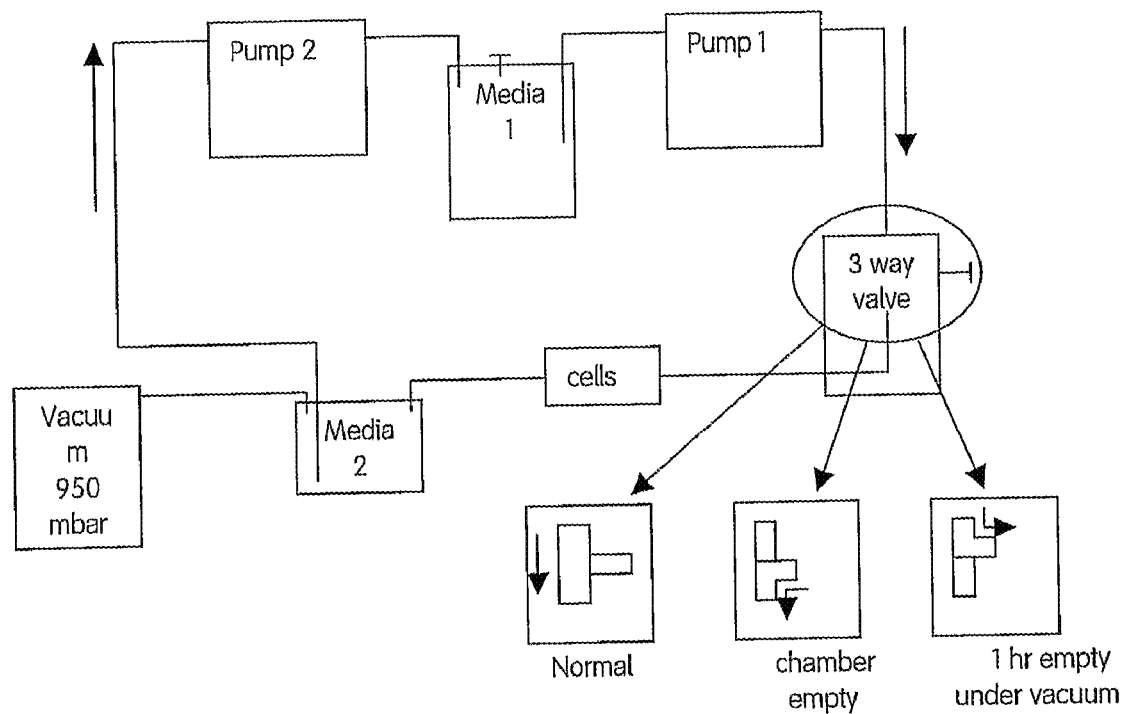

FIG. 30 is an apparatus where an irrigant is delivered continually to the wound bed and the resultant wound exudate/fluid mixture is at the same time continually aspirated from the wound.

DETAILED DESCRIPTION OF THE SPECIFIC EMBODIMENTS

Figure 1:
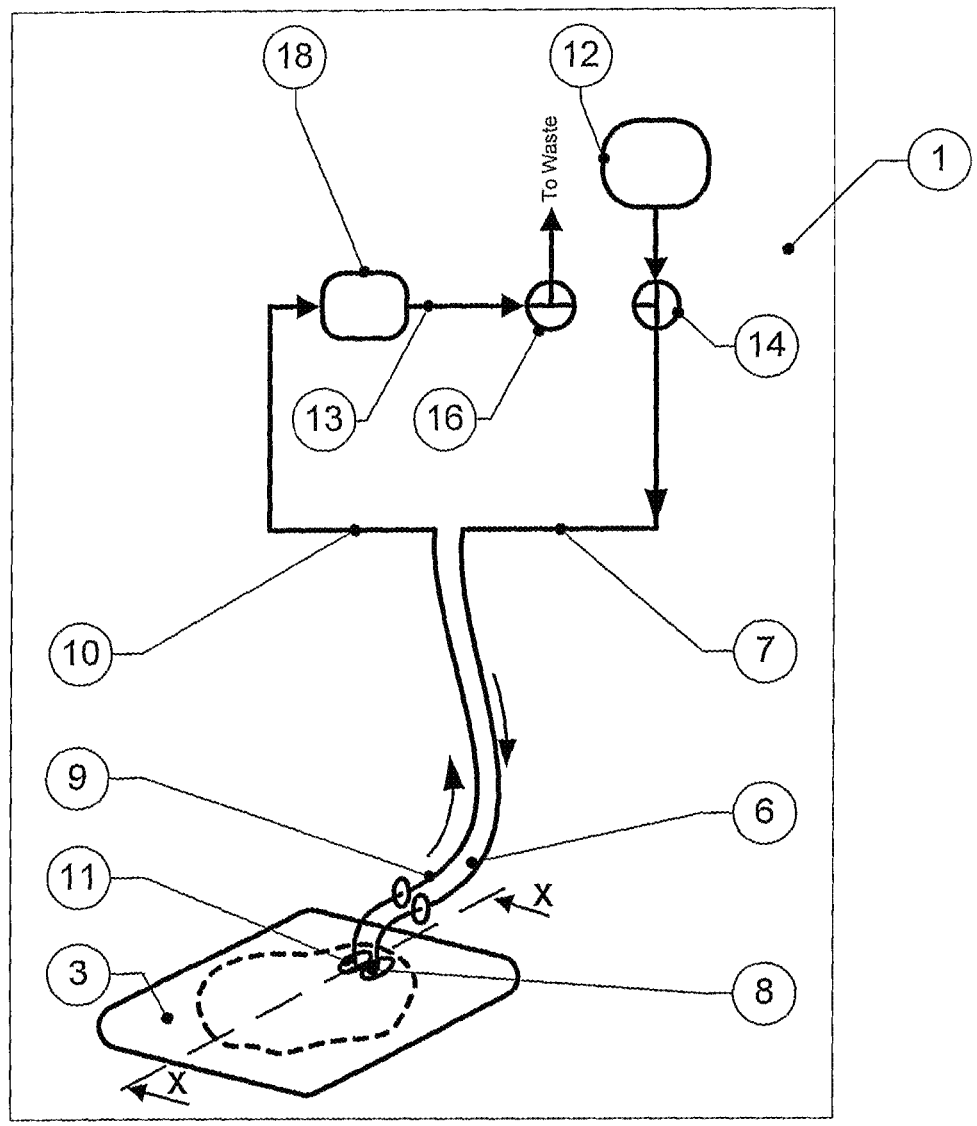
FIG. 1 is a schematic view of an apparatus for aspirating, irrigating and/or cleansing a wound according to the first aspect of the present invention that has a single device for moving fluid through the wound applied to the aspirate in the fluid offtake tube downstream of and away from the wound dressing, in combination with means for supply flow regulation, connected to a fluid supply tube, and means for aspirate flow regulation, connected to a fluid offtake tube.
Figure 1:
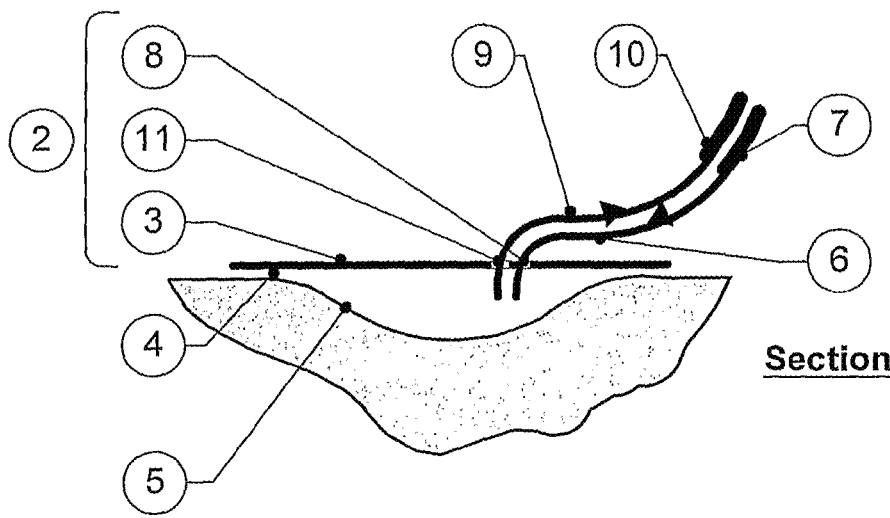

Referring to FIG. 1, the apparatus (1) for aspirating, irrigating and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (5) at (8), and one outlet pipe (9) for connection to a fluid offtake tube (10), which passes through the wound-facing face at (1), the points (8), (11) at which the inlet pipe and the outlet pipe passes through and/or under the wound-facing face forming a relatively fluid-tight seal or closure over the wound;

the inlet pipe being connected via means for supply flow regulation, here a valve (14), by the fluid supply tube (7) to a fluid reservoir (12), and the outlet pipe (9) being connected via means for aspirate flow regulation, here a valve (16) and a fluid offtake tube (10) to waste, e.g. to a collection bag (not shown);

a device for moving fluid through the wound (17), here a diaphragm pump (18), e.g. preferably a small portable diaphragm pump, acting on the fluid aspiration tube (13) to apply a low negative pressure on the wound; and the valve (14) in the fluid supply tube (7), the valve (16) in the fluid offtake tube (10), and the diaphragm pump (18), providing means for providing simultaneous aspiration and irrigation of the wound (5), such that fluid may be supplied to fill the flowpath from the fluid reservoir via the fluid supply tube (via the means for supply flow regulation) and moved by the device through the flow path.

The operation of the apparatus is as described hereinbefore.

Figure 2:
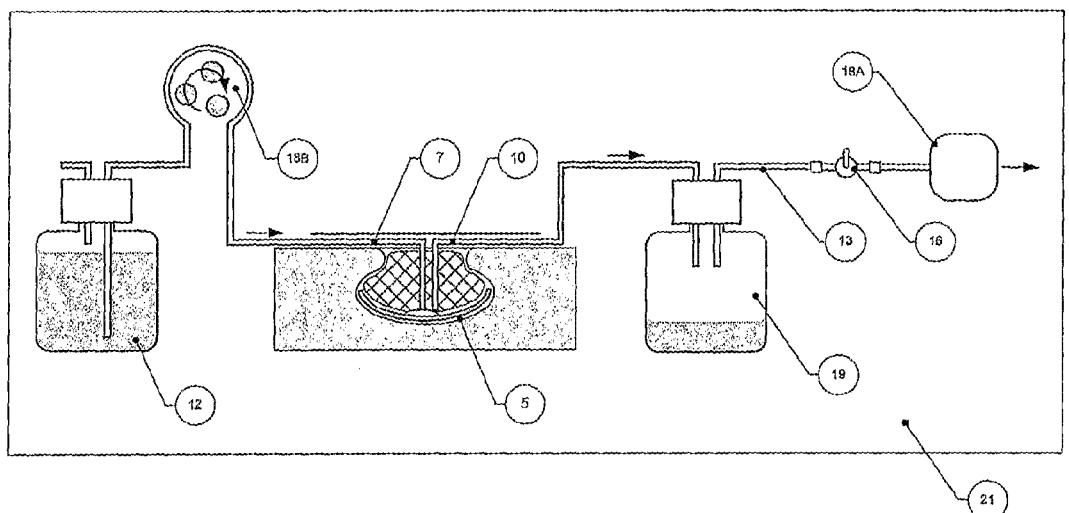
FIG. 2 is a schematic view of another apparatus for aspirating, irrigating and/or cleansing a wound according to the first aspect of the present invention that has a first device for moving fluid through the wound applied to the aspirate in the fluid offtake tube downstream of and away from the wound dressing, with means for aspirate flow regulation, connected to a fluid offtake tube; and a second device for moving fluid through the wound applied to the irrigant in the fluid supply tube upstream of and towards the wound dressing.

Referring to FIG. 2, the apparatus (21) is a variant two-pump system with essentially identical, and identically numbered, components as in FIG. 1, except that there is no means for supply flow regulation in the fluid supply tube (7) from the fluid reservoir (12), and there is a first device for moving fluid through the wound (5), here a diaphragm pump (18A), e.g. preferably a small portable diaphragm pump, acting on the fluid aspiration tube (13) downstream of and away from the wound dressing to apply a low negative pressure on the wound;

with means for negative pressure regulation, here a valve (16) connected to the vacuum tube (13) and a vacuum vessel (aspirate collection jar) (19); and a second device for moving fluid through the wound (5), here a peristaltic pump (18B), e.g. preferably a small portable diaphragm pump, applied to the irrigant in the fluid supply tube (7) upstream of and towards the wound dressing, the first device (18A) and second device (18B), and the valve (16) in the vacuum tube (13), and the diaphragm pump (18), providing means for providing simultaneous aspiration and irrigation of the wound (5), such that fluid may be supplied to fill the flowpath from the fluid reservoir via the fluid supply tube (via the means for supply flow regulation) and moved by the devices through the flow path.

The operation of the apparatus is as described hereinbefore

Referring to FIGS. 3A to 6B, each dressing (41) is in the form of a conformable body defined by a microbe-impermeable film backing layer (72) with a uniform thickness of 25 micron.

It has a wound-facing face (43), which is capable of forming a relatively fluid-tight seal or closure over a wound.

The backing layer (72) extends in use on a wound over the skin around the wound.

On the proximal face of the backing layer (43) on the overlap (44), it bears an adhesive film (45), to attach it to the skin sufficiently to hold the wound dressing in place in a fluid-tight seal around the periphery of the wound-facing face (43) of the wound dressing.

Figure 3A:
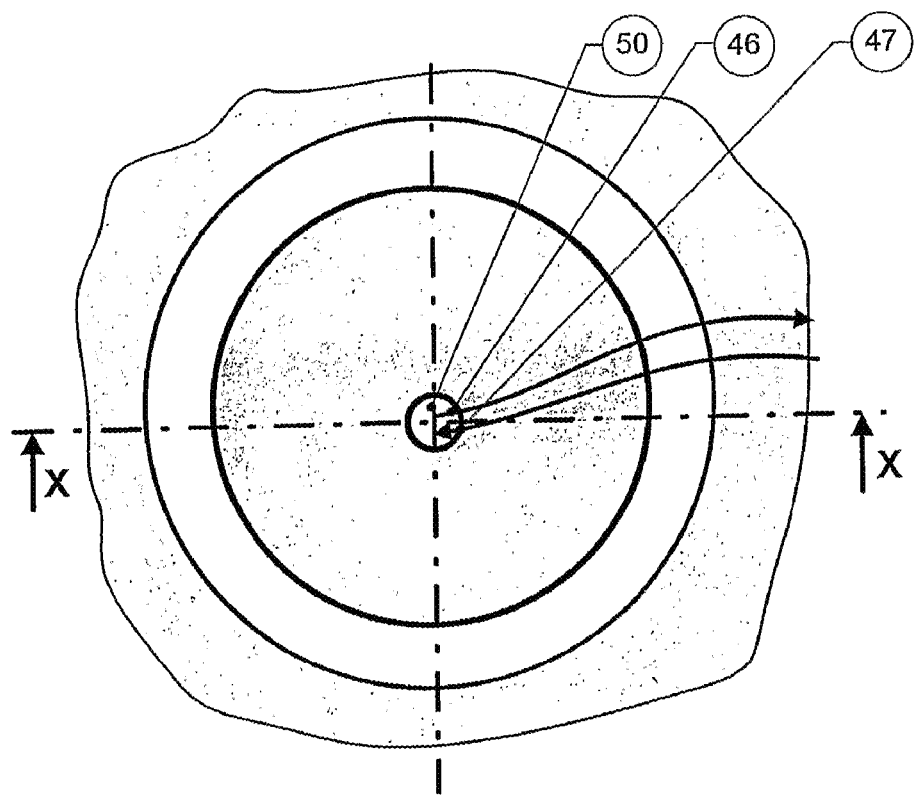
FIGS. 3A-B are cross-sectional views of conformable wound dressings, of the second aspect of the present invention for aspirating and/or irrigating wounds.
Figure 3B:
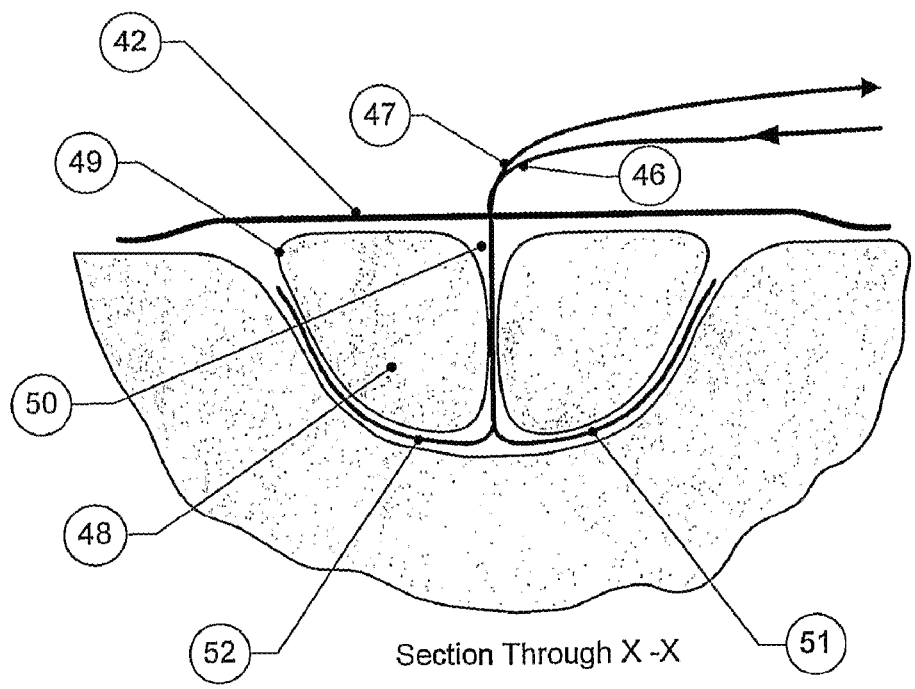

There is one inlet pipe (76) for connection to a fluid supply tube (not shown), which passes through and/or under the wound-facing face (43), and one outlet pipe (77) for connection to a fluid offtake tube (not shown), which passes through and/or under the wound-facing face (43), Referring to FIGS. 3A and 3B, one form of the dressing is provided with a wound filler (48) under a circular backing layer (42).

This comprises a generally frustroconical, toroidal conformable hollow body, defined by a membrane (49) which is filled with a fluid, here air or nitrogen, that urges it to the wound shape.

The filler (48) may be permanently attached to the backing layer with an adhesive film (not shown) or by heat-sealing.

The inlet pipe (46) and outlet pipe (47) are mounted centrally in the backing layer (42) above the central tunnel (50) of the toroidal hollow body (48) and each passes through the backing layer (42).

Each extends in pipes (51) and (52) respectively through the tunnel (50) of the toroidal hollow body (48) and then radially in diametrically opposite directions under the body (48).

This form of the dressing is a more suitable layout for deeper wounds.

Figure 4A:
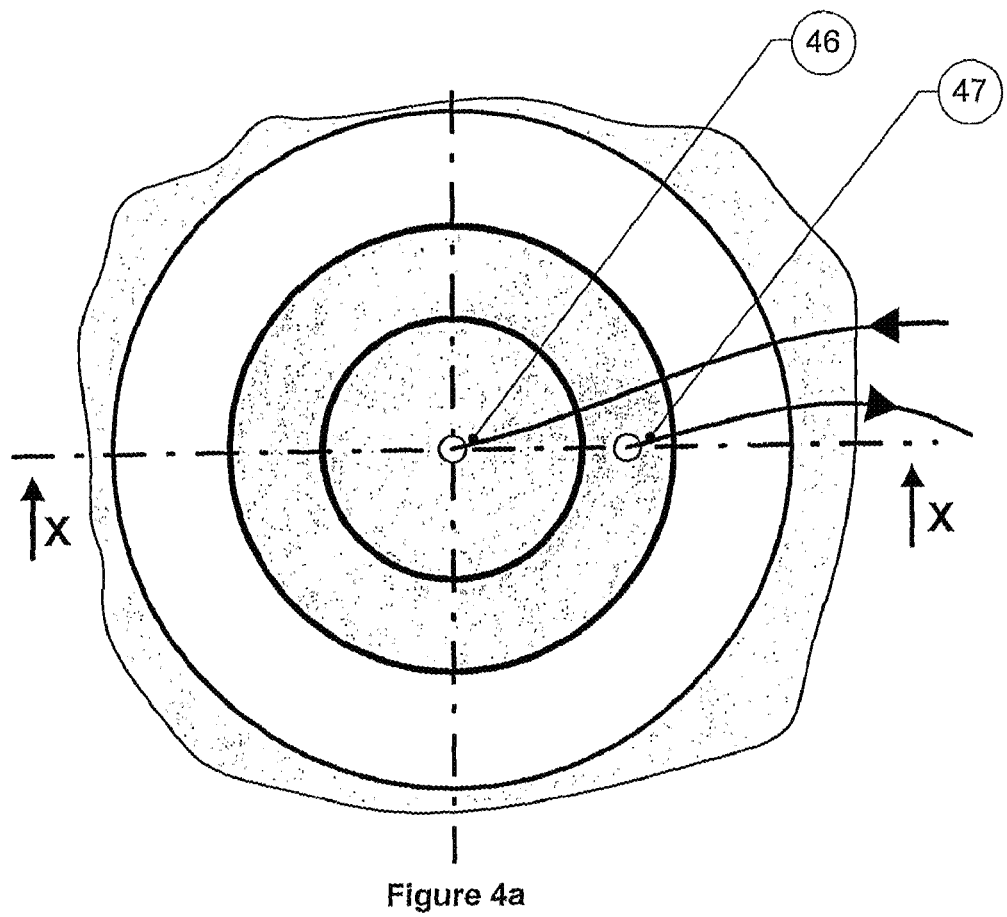
FIGS. 4A-B are cross-sectional plan and side views of the wound dressings.
Figure 4B:
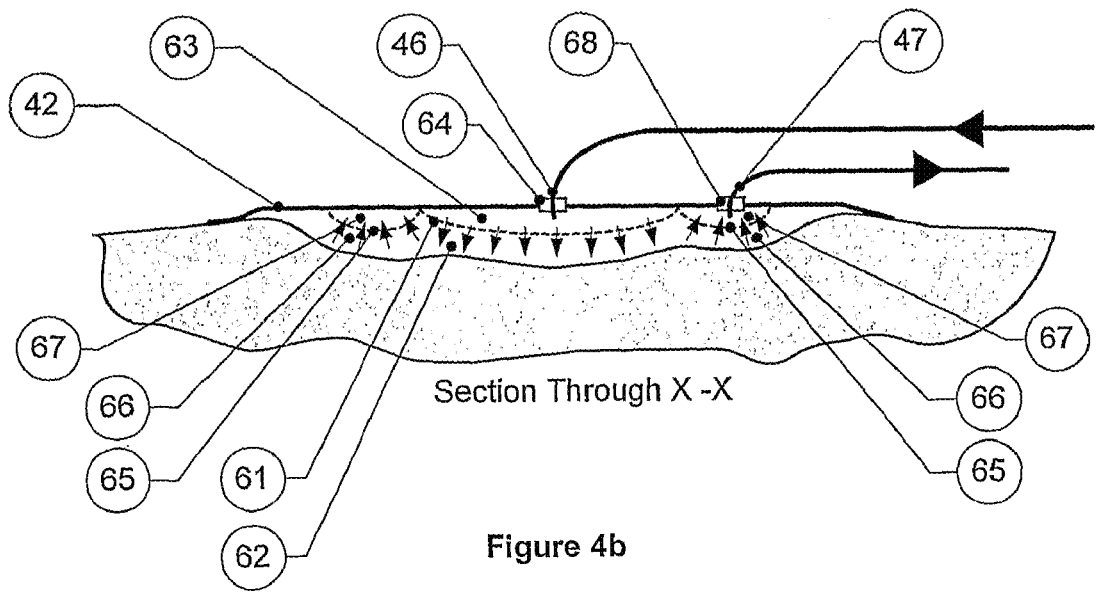

Referring to FIGS. 4A and 4B, a more suitable form for shallower wounds is shown.

This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the aspirating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Figure 5A:
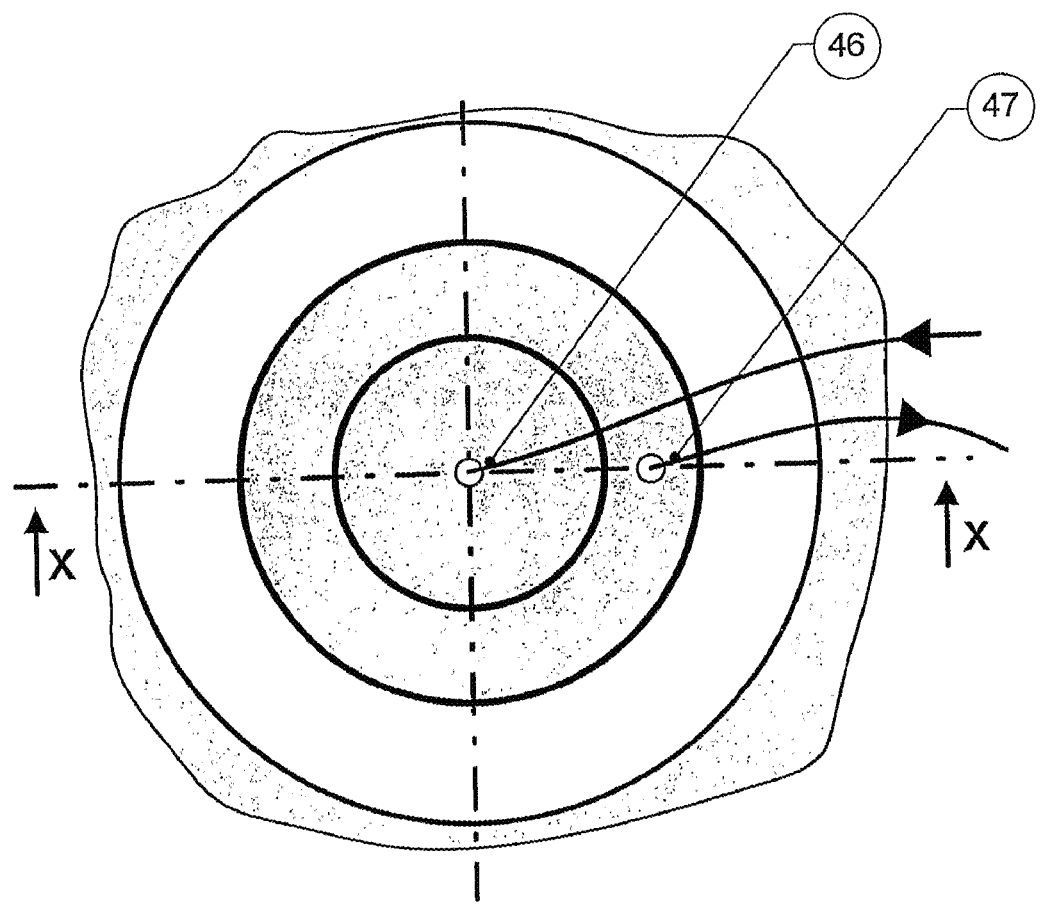
FIGS. 5A-B are cross-sectional plan and side views of the wound dressings.
Figure 5B:
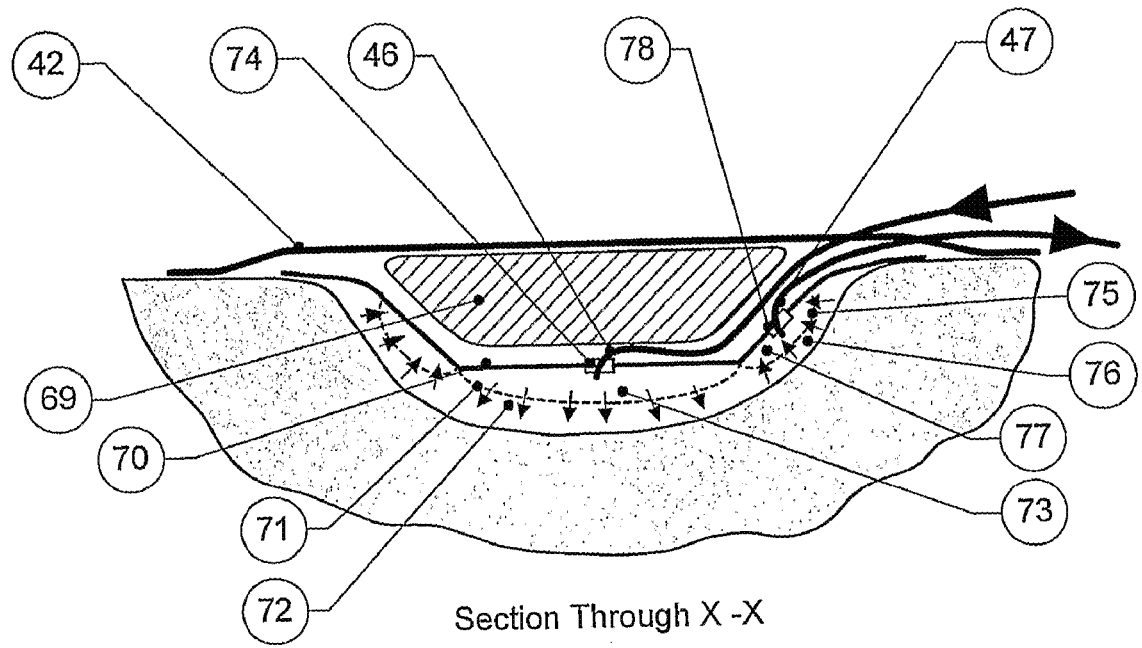

Referring to FIGS. 5A and 5B, a variant of the dressing of FIGS. 4A and 4B that is a more suitable form for deeper wounds is shown.

This comprises a circular backing layer (42) and a filler (69), in the form of an inverted frustroconical, solid integer, here a resilient elastomeric foam, formed of a thermoplastic, or preferably a cross-linked plastics foam.

It may be permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the aspirating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (47) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape, instead of the backing layer (42).

Figure 6A:
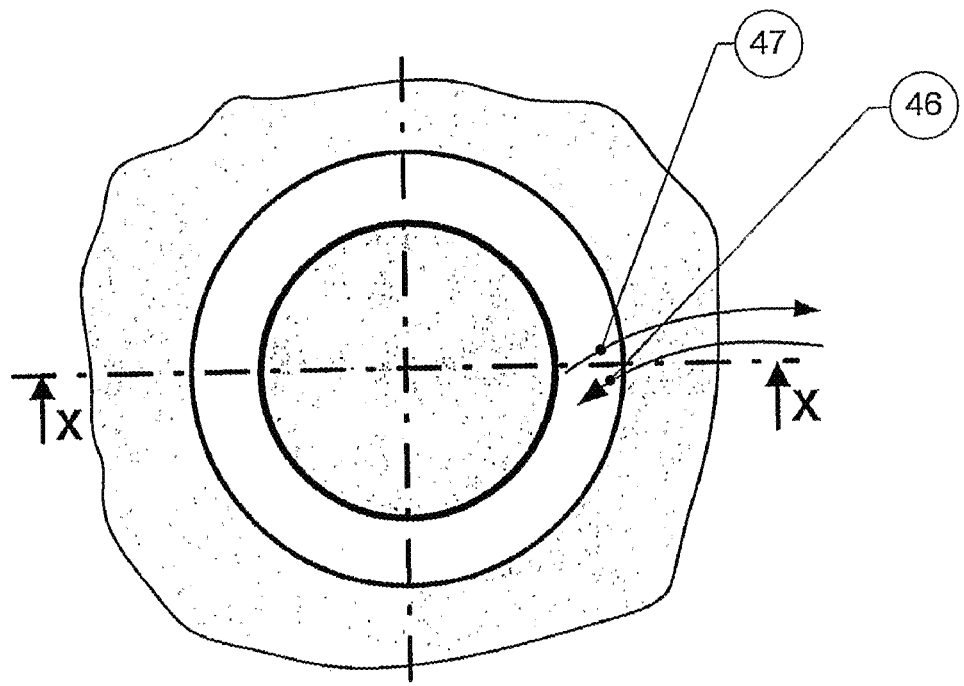
FIGS. 6A-B are cross-sectional plan and side views of the wound dressings.
Figure 6B:
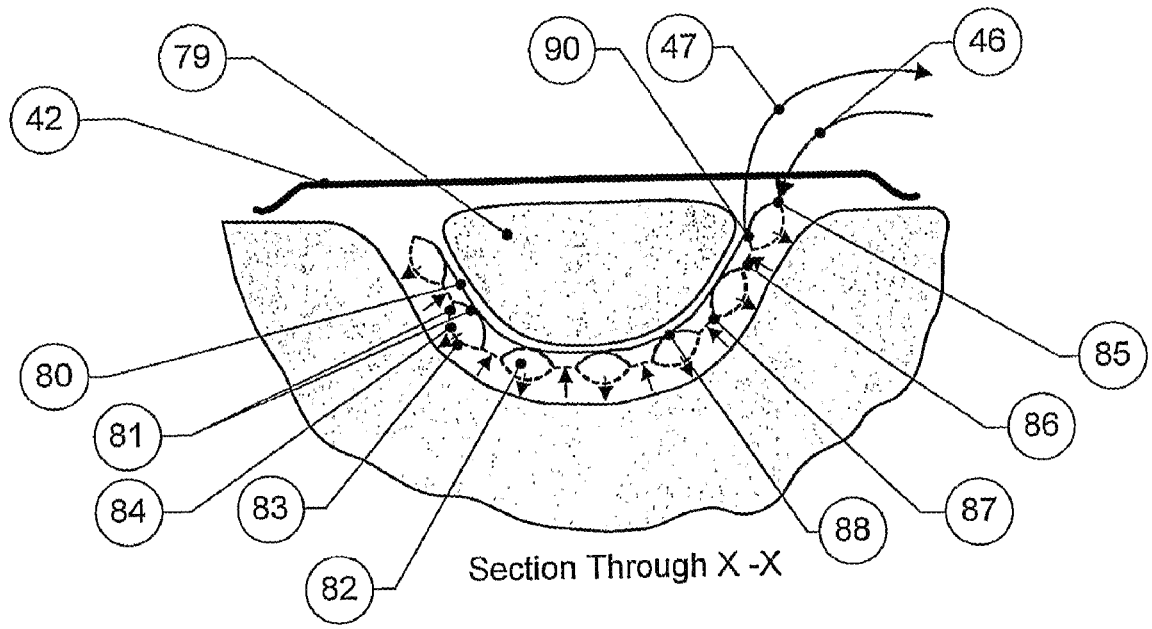

Referring to FIGS. 6A and 6B, a dressing that is a more suitable form for deeper wounds is shown.

This comprises a circular backing layer (42) and a filler (79), in the form of an inverted generally hemispherical integer, permanently attached to the backing layer with an adhesive film (not shown) or by heat-sealing. Here it is a resilient elastomeric foam or a hollow body filled with a fluid, here a gel that urges it to the wound shape.

The inlet pipe (46) and outlet pipe (47) are mounted peripherally in the backing layer (42).

A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with perforations (83) along its length on the outer surface (84) of the dish formed by the membrane (81) and an opening (85) at the outer end of its spiral helix, through which the channel (82) communicates with the inlet pipe (46), and thus effectively forms an inlet pipe manifold that delivers the aspirating fluid directly to the wound when the dressing is in use.

The membrane (81) also has apertures (86) between and along the length of the turns of the channel (82).

The inner surface (87) of the dish formed by the membrane (81) is permanently attached at its innermost points (88) with an adhesive film (not shown) or by heat-sealing to the sheet (80). This defines a mating closed spirohelical conduit (89).

At the outermost end of its spiral helix, the conduit (89) communicates through an opening (90) with the outlet pipe (47) and is thus effectively an outlet manifold to collect the fluid directly from the wound via the apertures (86).

Figure 7A:
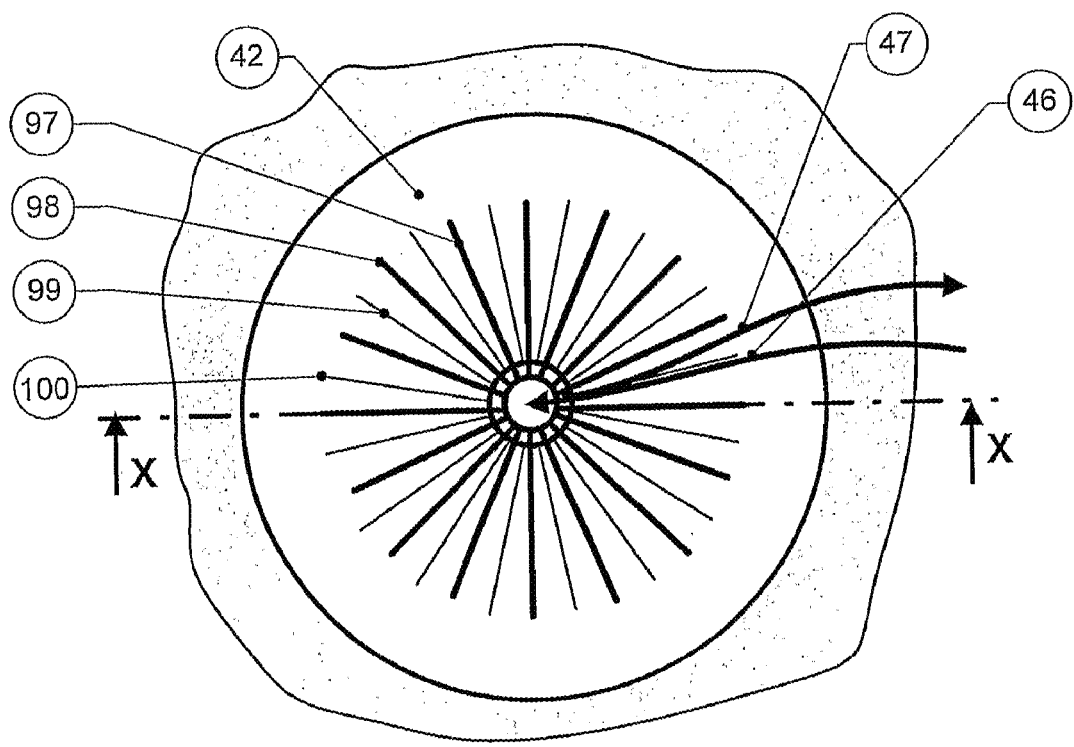
FIGS. 7A-B are cross-sectional plan and side views of the wound dressings.
Figure 7B:
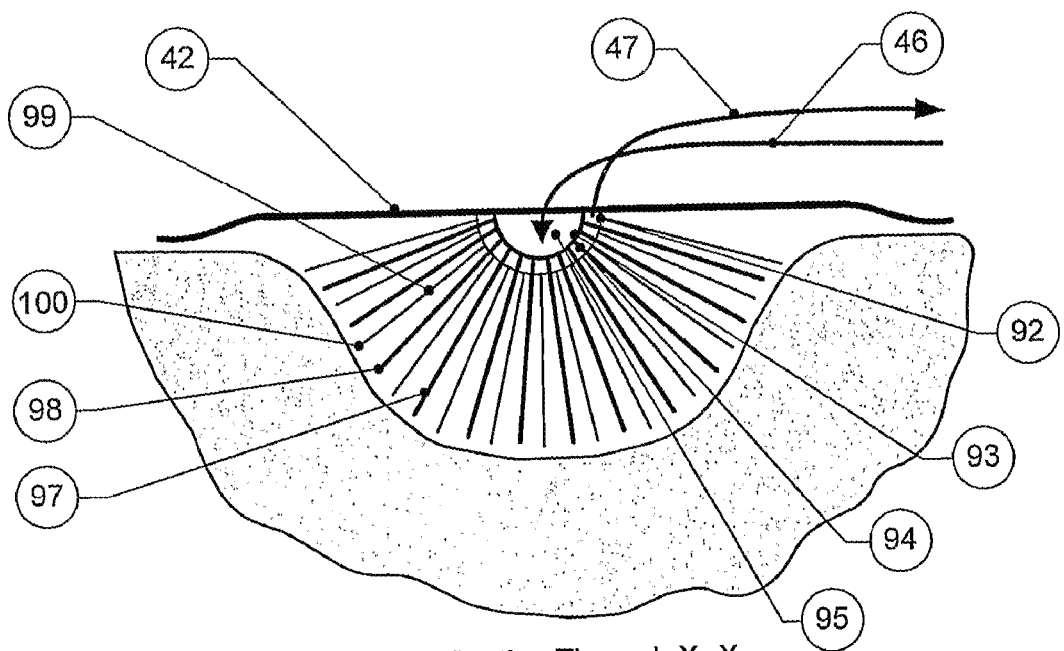

Referring to FIGS. 7A and 7B, one form of the dressing is provided with a circular backing layer (42).

A first (larger) inverted hemispherical membrane (92) is permanently attached centrally to the layer (42) by heat-sealing to form a hemispherical chamber (94) with the layer (42).

A second (smaller) concentric hemispherical membrane (93) within the first is permanently attached to the layer (42) by heat-sealing to form a hemispherical pouch (95).

The pouch (95) communicates with the inlet pipe (46) and is thus effectively an inlet manifold, from which pipes (97) radiate hemispherically and run to the wound bed to end in apertures (98). The pipes (97) deliver the aspirating fluid directly to the wound bed via the apertures (98).

The chamber (94) communicates with the outlet pipe (47) and is thus effectively an outlet manifold from which tubules (99) radiate hemispherically and run to the wound bed to end in openings (100). The tubules (99) collect the fluid directly from the wound via the openings (100).

Referring to FIGS. 8A to 8D, one form of the dressing is provided with a square backing layer (42) and first tube (101) extending from the inlet pipe (46), and second tube (102) extending from the outlet pipe (47) at the points at which they pass through the backing layer, to run over the wound bed.

These pipes (101), (102) have a blind bore with orifices (103), (104) along the pipes (101), (102).

These pipes (101), (102) respectively form an inlet pipe or outlet pipe manifold that delivers the aspirating fluid directly to the wound bed or collects the fluid directly from the wound respectively via the orifices.

Figure 8A:
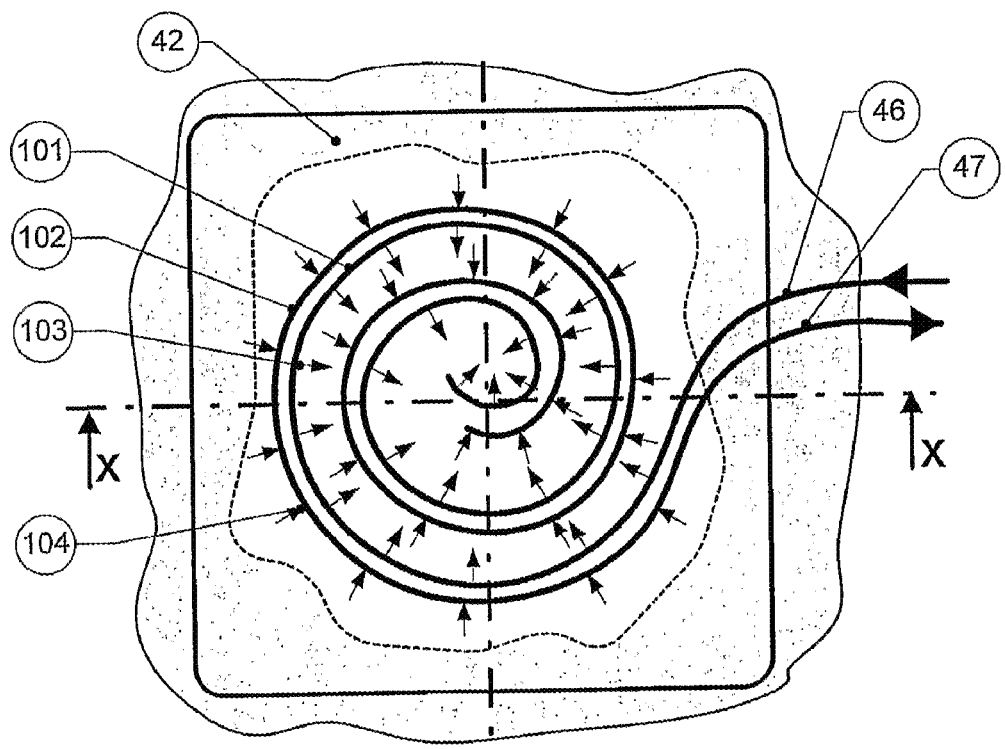
FIGS. 8A-D are various views of inlet and outlet manifold layouts for the wound dressings of the second aspect of the present invention for respectively delivering fluid to, and collecting fluid from, the wound.
Figure 8B:
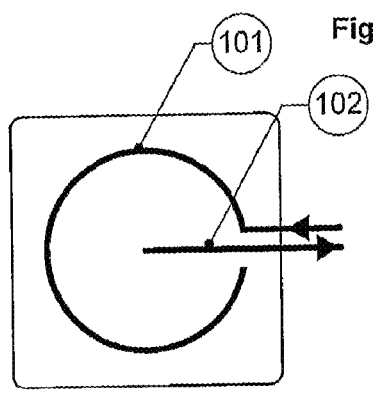
Figure 8C:
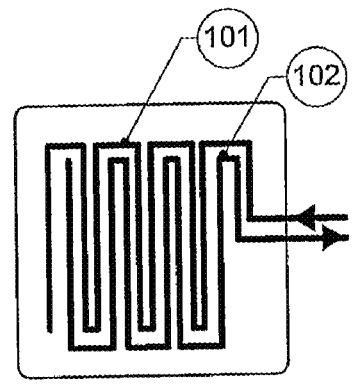
Figure 8D:
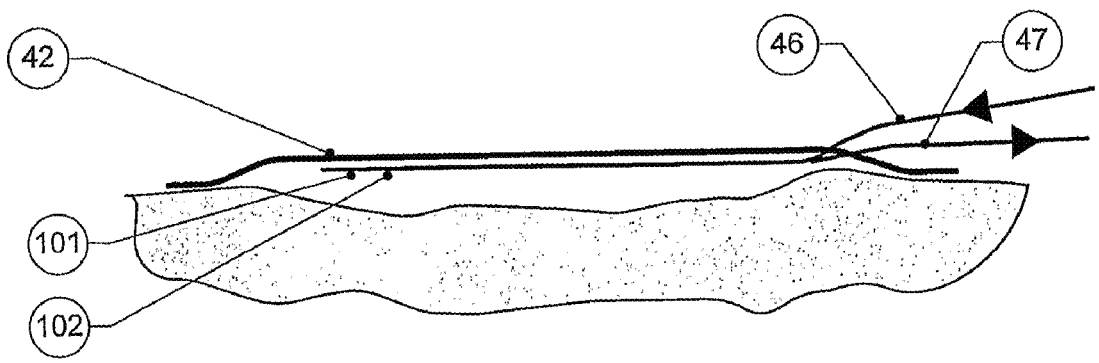
Figure 9A:
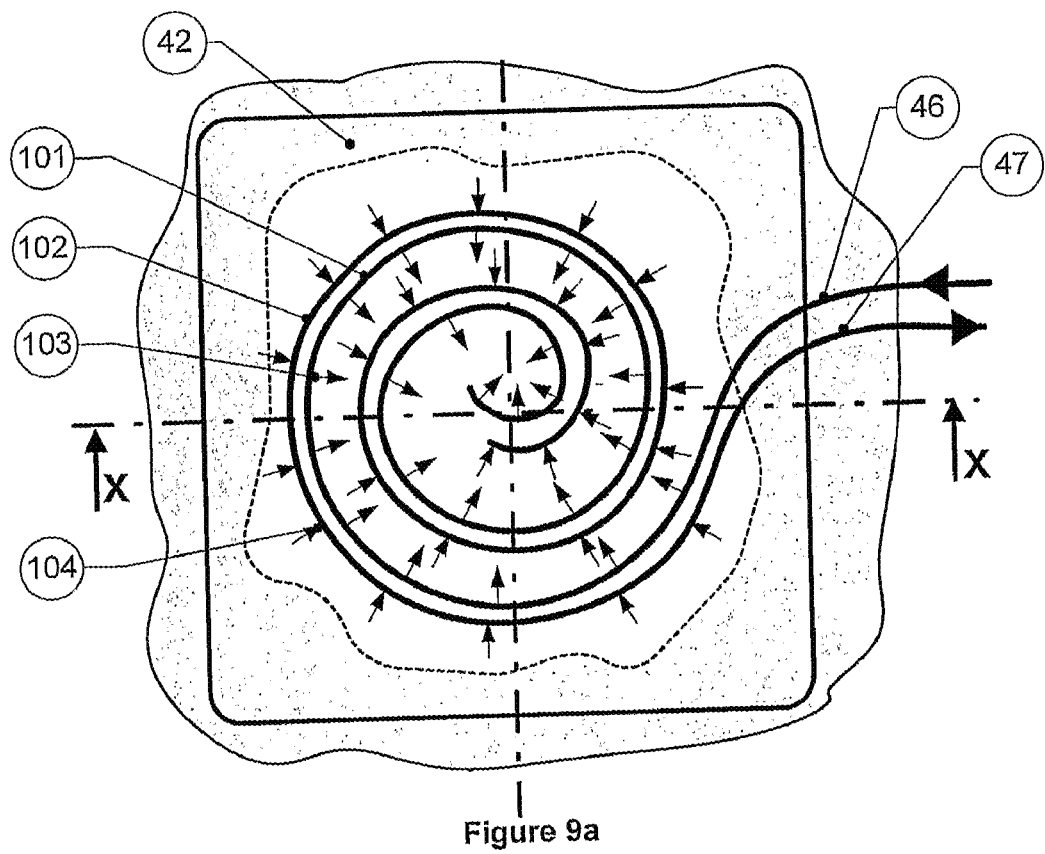
FIGS. 9A-B are various views of inlet and outlet manifold layouts for the wound dressings of the second aspect of the present invention for respectively delivering fluid to, and collecting fluid from, the wound.
Figure 9B:
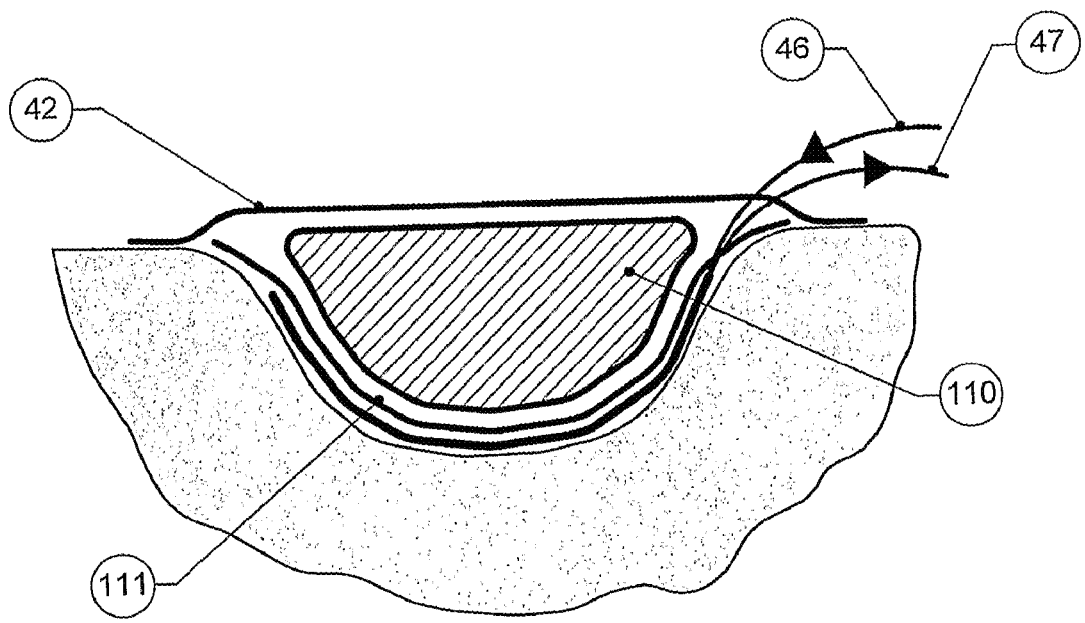

In FIGS. 8A and 8D, one layout of each of the pipes (101), (102) as inlet pipe and outlet pipe manifolds is a spiral.

In FIG. 8B, the layout is a variant of that of FIGS. 8a and 8b, with the layout of the inlet manifold (101) being a full or partial torus, and the outlet manifold (102) being a radial pipe.

Referring to FIG. 8C, there is shown another suitable layout in which the inlet manifold (101) and the outlet manifold (102) run alongside each other over the wound bed in a boustrophedic pattern, i.e. in the manner of ploughed furrows.

Referring to FIGS. 9A to 9D, there are shown other suitable layouts for deeper wounds, which are the same as shown in FIGS. 8A to 8D. The square backing layer (42) however has a wound filler (110) under, and may be permanently attached to, the backing layer (42), with an adhesive film (not shown) or by heat-sealing, which is an inverted hemispherical solid integer, here a resilient elastomeric foam, formed of a thermoplastic, preferably a cross-linked plastics foam.

Under the latter is a circular upwardly dished sheet (111) which conforms to, but is a separate structure, permanently unattached to, the solid filler (110). Through the sheet (111) pass the inlet pipe (46) and the outlet pipe (47), to run over the wound bed. These pipes (101), (102) again have a blind bore with orifices (103), (104) along the pipes (101), (102).

Alternatively (as in FIGS. 5A and 5B), where appropriate the dressing may be provided in a form in which the circular upwardly dished sheet (111) functions as the backing layer and the solid filler (110) sits on the sheet (42) as the backing layer, rather than under it. The filler (110) is held in place with an adhesive film or tape, instead of the backing layer (42).

Figure 10A:
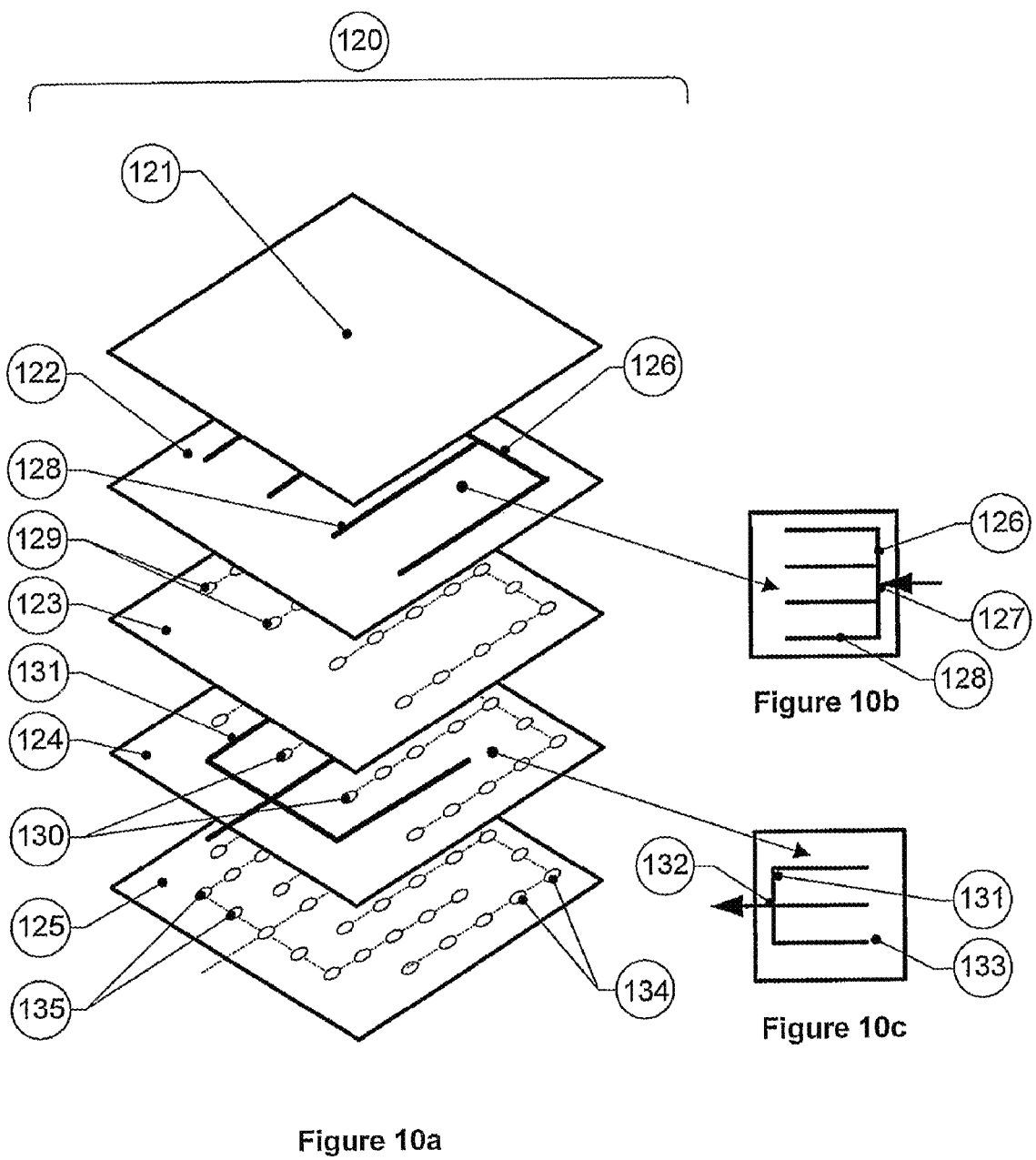

In FIGS. 10A to 10C, inlet and outlet manifolds for the wound dressings for respectively delivering fluid to, and collecting fluid from, the wound, are formed by slots in and apertures through layers permanently attached to each other in a stack.

Thus, in FIG. 10A there is shown an exploded isometric view of an inlet manifold and outlet manifold stack (120) of five square coterminous thermoplastic polymer layers, being first to fifth layers (121) to (125), each attached with an adhesive film (not shown) or by heat-sealing to the adjacent layer in the stack (120).

The topmost (first) layer (121) (which is the most distal in the dressing in use) is a blank square capping layer.

The next (second) layer (122), shown in FIG. 10B out of the manifold stack (120), is a square layer, with an inlet manifold slot (126) through it. The slot (126) runs to one edge (127) of the layer (122) for connection to a mating end of a fluid inlet tube ((not shown), and spreads into four adjacent branches (128) in a parallel array with spaces therebetween.

The next (third) layer (123) is another square layer, with inlet manifold apertures (129) through the layer (123) in an array such that the apertures (129) are in register with the inlet manifold slot (126) through the second layer (122) (shown in FIG. 10B).

The next (fourth) layer (124), shown in FIG. 10C out of the manifold stack (120), is another square layer, with inlet manifold apertures (130) through the layer (124) in an array such that the apertures (130) are in register with the apertures (129) through the third layer (123).

It also has an outlet manifold slot (131) through it.

The slot (131) runs to one edge (132) of the layer (124) on the opposite side of the manifold stack (120) from the edge (127) of the layer (122), for connection to a mating end of a fluid outlet tube (not shown).

It spreads into three adjacent branches (133) in a parallel array in the spaces between the apertures (130) in the layer (124) and in register with the spaces between the apertures (129) in the layer (122).

The final (fifth) layer (125) is another square layer, with inlet manifold apertures (134) through the layer (125) in an array such that the apertures (134) are in register with the inlet manifold apertures (130) through the fourth layer (124) (in turn in register with the apertures (129) through the third layer (123). It also has outlet manifold apertures (135) in the layer (125) in an array such that the apertures (135) are in register with the outlet manifold slot (131) in the fourth layer (124).

It will be seen that, when the layers (121) to (125) are attached together to form the stack (120), the topmost (first) layer (121), the inlet manifold slot (126) through the second layer (122), and the third layer (123) cooperate to form an inlet manifold in the second layer (122), which is in use is connected to a mating end of a fluid inlet tube (not shown).

The inlet manifold slot (126) through the second layer (122), and the inlet manifold apertures (129), (130) and (134) through the layers (123), (124) and (125), all being mutually in register, cooperate to form inlet manifold conduits though the third to fifth layers (123), (124) and (125) between the inlet manifold in the second layer (122) and the proximal face (136) of the stack (120).

The third layer (121), the outlet manifold slot (131) through the fourth layer (124), and the fifth layer (125) cooperate to form an outlet manifold in the fourth layer (124), which is in use is connected to a mating end of a fluid outlet tube (not shown).

The outlet manifold slot (131) through the fourth layer (124), and the outlet manifold apertures (135) through the fifth layer (125), being mutually in register, cooperate to form outlet manifold conduits though the fifth layer (125) between the outlet manifold in the fourth layer (124) and the proximal face (136) of the stack (120).

Referring to FIG. 11A, the apparatus (21) is a variant two-pump system with essentially identical, and identically numbered, components as in FIG. 2.

Thus, there is a means for supply flow regulation, here a valve (14) in the fluid supply tube (7) from the fluid reservoir (12), and a first device for moving fluid through the wound (5), here a fixed-speed diaphragm pump (18A), e.g. preferably a small portable diaphragm pump, acting not on the fluid aspiration tube (13), but on an air aspiration tube (113) downstream of and away from an aspirate collection vessel (19) to apply a low negative pressure on the wound through the aspirate collection vessel (19); with a second device for moving fluid through the wound (5), here a fixed-speed peristaltic pump (18B), e.g. preferably a small portable peristaltic pump, applied to the irrigant in the fluid supply tube (7) upstream of and towards the wound dressing, the first device (18A) and second device (18B), and the valve (14) in the fluid supply tube (7), providing means for providing simultaneous aspiration and irrigation of the wound (5), such that fluid may be supplied to fill the flowpath from the fluid reservoir via the fluid supply tube (via the means for supply flow regulation) and moved by the devices through the flow path.

There is no means for aspirate flow regulation, e.g. a valve connected to the fluid offtake tube (10).

Since first device (18A) and second device (18B) are fixed-speed, the valve (14) in the fluid supply tube (7)

provides the sole means for varying the irrigant flow rate and the low negative pressure on the wound.

The following extra features are present:

The second device, the fixed-speed peristaltic pump (18B), is provided with means for avoiding over-pressure, in the form of a bypass loop with a non-return valve (115). The loop runs from the fluid supply tube (7) downstream of the pump (18B) to a point in the fluid supply tube (7) upstream of the pump (18B).

A pressure monitor (116) connected to the fluid offtake tube (10) has a feedback connection to a bleed regulator, here a motorised rotary valve (117) on a bleed tube (118) running to and centrally penetrating the top of the aspirate collection vessel (19). This provides means for holding the low negative pressure on the wound at a steady level.

A filter (119) downstream of the aspirate collection vessel (19) prevents passage of gas- (often air-) borne particulates, including liquids and micro-organisms, from the irrigant and/or exudate that passes into the aspirate collection vessel (19) into the first device (18A), whilst allowing the carrier gas to pass through the air aspiration tube (113) downstream of it to the first device (18A). The operation of the apparatus is as described hereinbefore Referring to FIG. 11B, this shows an alternative layout of the essentially identical, and identically numbered, components in FIG. 11A downstream of point A in FIG. 11A. The bleed tube (118) runs to the air aspiration tube (113) downstream of the filter (119), rather than into the aspirate collection vessel (19). This provides means for holding the low negative pressure on the wound at a steady level. The operation of the apparatus is as described hereinbefore Referring to FIG. 11C, this shows an alternative layout of the essentially identical, and identically numbered, components in FIG. 11A upstream of point B in FIG. 11A. The second device (18B) is a variable-speed pump, and the valve (14) in the fluid supply tube (7) is omitted. The second device (18B) is the sole means for varying the irrigant flow rate and the low negative pressure on the wound. The operation of the apparatus is as described hereinbefore Referring to FIG. 11D, this shows an alternative layout of the essentially identical, and identically numbered, components in FIG. 11A downstream of point B in FIG. 11A.

The pressure monitor (116) is connected to a monitor offtake tube (120) and has a feedback connection to the bleed regulator, motorised rotary valve (117) on a bleed tube (118) running to the monitor offtake tube (120). This provides means for holding the low negative pressure on the wound at a steady level. The operation of the apparatus is as described hereinbefore Referring to FIG. 12A, this shows another alternative layout of the essentially identical, and identically numbered, components in FIG. 11A downstream of point B in FIG. 11A.

The pressure monitor (116) is connected to a monitor offtake tube (120) and has a feedback connection to a means for aspirate flow regulation, here a motorised valve (16) in the air aspiration tube (113) downstream of the filter (119).

This provides means for aspirate flow regulation and for holding the low negative pressure on the wound at a steady level. The operation of the apparatus is as described hereinbefore Referring to FIG. 12B, this shows another alternative layout of the essentially identical, and identically numbered, components in FIG. 12A downstream of point B in FIG. 11A. The pressure monitor (116) is connected to a monitor offtake tube (120) and has a feedback connection to a means for aspirate flow regulation, here a motorised valve (16), in the fluid offtake tube (10) upstream of the aspirate collection vessel (19).

This provides means for aspirate flow regulation and for holding the low negative pressure on the wound at a steady level. The operation of the apparatus is as described hereinbefore Referring to FIG. 12C, this shows another alternative layout of the essentially identical, and identically numbered, components in FIG. 12A downstream of point B in FIG. 11A.

The pressure monitor (116) is connected to a monitor offtake tube (120) and has a feedback connection to a variable-speed first device (18A), here a variable-speed pump, downstream of the filter (119), and the valve (16) in the fluid offtake tube (10) is omitted.

This provides means for aspirate flow regulation and for holding the low negative pressure on the wound at a steady level. The operation of the apparatus is as described hereinbefore.

Referring to FIGS. 13A to 15, these forms of the dressing are provided with a wound filler (348) under a circular backing layer (342).

This comprises respectively a generally downwardly domed or toroidal, or oblately spheroidal conformable hollow body, defined by a membrane (349) which is filled with a fluid, here air or nitrogen, that urges it to the wound shape.

The filler (348) is permanently attached to the backing layer via a boss (351), which is e.g. heat-sealed to the backing layer (342).

An inflation inlet pipe (350), inlet pipe (346) and outlet pipe (347) are mounted centrally in the boss (351) in the backing layer (342) above the hollow body (348). The inflation inlet pipe (350) communicates with the interior of the hollow body (348), to permit inflation of the body (348). The inlet pipe (346) extends in a pipe (352) effectively through the hollow body (348). The outlet pipe (347) extends radially immediately under the backing layer (342).

In FIGS. 13A-B, the pipe (352) communicates with an inlet manifold (353), formed by a membrane (361) with apertures (362) that is permanently attached to the filler (348) by heat-sealing.

It is filled with foam (363) formed of a suitable material, e.g. a resilient thermoplastic. Preferred materials include reticulated filtration polyurethane foams with small apertures or pores.

In FIG. 14, the outlet pipe (347) communicates with a layer of foam (364) formed of a suitable material, e.g. a resilient thermoplastic. Again, preferred materials include reticulated filtration polyurethane foams with small apertures or pores.

In all of FIGS. 13A-B, 14 and 15, in use, the pipe (346) ends in one or more openings that deliver the irrigant fluid directly from the wound bed over an extended area.

Similarly, the outlet pipe (347) effectively collects the fluid radially from the wound periphery when the dressing is in use.

Referring to FIG. 16A-B, the dressing is also provided with a wound filler (348) under a circular backing layer (342).

This also comprises a generally toroidal conformable hollow body, defined by a membrane (349) which is filled with a fluid, here air or nitrogen, that urges it to the wound shape.

The filler (348) may be permanently attached to the backing layer (342) via a first boss (351) and a layer of foam (364) formed of a suitable material, e.g. a resilient thermoplastic. Again, preferred materials include reticulated filtration polyurethane foams with small apertures or pores.

The first boss (351) and foam layer (364) are respectively heat-sealed to the backing layer (342) and the boss (351).

An inflation inlet pipe (350), inlet pipe (346) and outlet pipe (347) are mounted centrally in the first boss (351) in the backing layer (342) above the toroidal hollow body (348).

The inflation inlet pipe (350), inlet pipe (346) and outlet pipe (347) respectively each extend in a pipe (353), (354) and (355) through a central tunnel (356) in the hollow body (348) to a second boss (357) attached to the toroidal hollow body (348).

The pipe (353) communicates with the interior of the hollow body (348), to permit inflation of the body (348).

The pipe (354) extends radially through the second boss (357) to communicate with an inlet manifold (352), formed by a membrane (361).

This is permanently attached to the filler (348) by heat-sealing in the form of a reticulated honeycomb with openings (362) that deliver the irrigant fluid directly to the wound bed over an extended area.

The pipe (355) collects the fluid flowing radially from the wound centre when the dressing is in use.

This form of the dressing is a more suitable layout for deeper wounds

In FIG. 17, the dressing is similar to that of FIGS. 16A-B, except that the toroidal conformable hollow body, defined by a membrane (349), is filled with a fluid, here a solid particulates, such as plastics crumbs or beads, rather than a gas, such as air or an inert gas, such as nitrogen or argon. The inflation inlet pipe (350) and pipe (353) are omitted from the central tunnel (356).

Examples of contents for the body (348) also include gels, such as silicone gels or preferably cellulosic gels, for example hydrophilic cross-linked cellulosic gels, such as Intrasite™ cross-linked materials. Examples also include aerosol foams, and set aerosol foams, e.g. CaviCare™ foam.

Referring to FIGS. 18A-B and 19, another form for deeper wounds is shown. This comprises a circular backing layer (342) and a lobed chamber (363) in the form of a deeply indented disc much like a multiple Maltese cross or a stylised rose.

This is defined by an upper impervious membrane (361) and a lower porous film (362) with apertures (364) that deliver the irrigant fluid directly from the wound bed over an extended area.

A number of configurations of the chamber (363) are shown, all of which are able to conform well to the wound bed by the arms closing in and possibly overlapping in insertion into the wound.

In a particular design of the chamber (363), shown lowermost, on of the arms extended and provided with an inlet port at the end of the extended arm. This provides the opportunity for coupling and decoupling the irrigant supply remote from the dressing and the wound in use.

An inlet pipe (346) and outlet pipe (347) are mounted centrally in a boss (351) in the backing layer (342) above the chamber (363). The inlet pipe (346) is permanently attached to, and communicate with the interior of, the chamber (363), which thus effectively forms an inlet manifold. The space above the chamber (363) is filled with a loose gauze packing (364).

In FIG. 18A, the outlet pipe (347) collects the fluid from the interior of the dressing from just under the wound-facing face (343) of the backing layer (342).

A variant of the dressing of FIGS. 18A-B is shown in FIG. 19. The outlet pipe (347) is mounted to open at the lowest point of the space above the chamber (363) into a piece of foam (374).

In FIG. 20, the dressing is similar to that of FIG. 13A-B, except that the inlet pipe (352) communicates with an inlet manifold (353).

The latter is formed by a membrane (361) with apertures (362), over the upper surface of the generally downwardly domed wound hollow filler (348), rather than through it.

In FIG. 21, the dressing is similar to that of FIG. 14, with the addition of an inlet manifold (353), formed by a membrane (361) with apertures (362), over the lower surface of the generally downwardly domed annular wound hollow filler.

In FIG. 22, the generally downwardly domed annular wound hollow filler is omitted.

Referring to FIG. 23, another form for deeper wounds is shown. An inlet pipe (346) and outlet pipe (347) are mounted centrally in a boss (351) in the backing layer (342) above a sealed-off foam filler (348).

The inlet pipe (346) is permanently attached to and passes through the filler (348) to the wound bed. The outlet pipe (347) is attached to and communicates with the interior of, a chamber (363) defined by a porous foam attached to the upper periphery of the filler (348). The chamber (363) thus effectively forms an outlet manifold.

In FIG. 24, the foam filler (348) is only partially sealed-off. The inlet pipe (346) is permanently attached to and passes through the filler (348) to the wound bed. The outlet pipe (347) is attached to and communicates with the interior of the foam of the filler (348). Fluid passes into an annular gap (349) near the upper periphery of the filler (348) into the foam, which thus effectively forms an outlet manifold.

FIGS. 25 and 26 show dressings in which the inlet pipe (346) and outlet pipe (347) pass through the backing layer (342).

In FIG. 25, they communicate with the interior of a porous bag filler (348) defined by a porous film (369) and filled with elastically resilient plastics bead or crumb.

In FIG. 26, they communicate with the wound space just below a foam filler (348). The foam (348) may CaviCare™ foam, injected and formed in situ around the pipes (346) and (347).

Referring to FIGS. 27A-B, another form for deeper wounds is shown. This comprises a circular, or more usually square or rectangular backing layer (342) and a chamber (363) in the form of a deeply indented disc much like a multiple Maltese cross or a stylised rose.

This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 27B, all of which are able to conform well to the wound bed by the arms closing in and possibly overlapping in insertion into the wound.

The space above the chamber (363) is filled with a wound filler (348) under the backing layer (342). This comprises an oblately spheroidal conformable hollow body, defined by a membrane (349) that is filled with a fluid, here air or nitrogen, that urges it to the wound shape.

A moulded hat-shaped boss (351) is mounted centrally on the upper impervious membrane (361) of the chamber (363). It has three internal channels, conduits or passages through it (not shown), each with entry and exit apertures. The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing.

It extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

Referring to FIG. 28A, this shows another alternative layout of the essentially identical, and identically numbered, components in FIG. 12C downstream of point B in FIG. 12A, and alternative means for handling the aspirate flow to the aspirate collection vessel under negative or positive pressure to the wound. The pressure monitor (116) is connected to a monitor offtake tube (120) and has a feedback connection to a variable-speed first device (18A), here a variable-speed pump, upstream of the aspirate collection vessel (19), and the filter (119) and the air aspiration tube (113) are omitted. This provides means for aspirate flow regulation and for holding the low negative pressure on the wound at a steady level. The operation of the apparatus is as described hereinbefore.

Figure 28B:
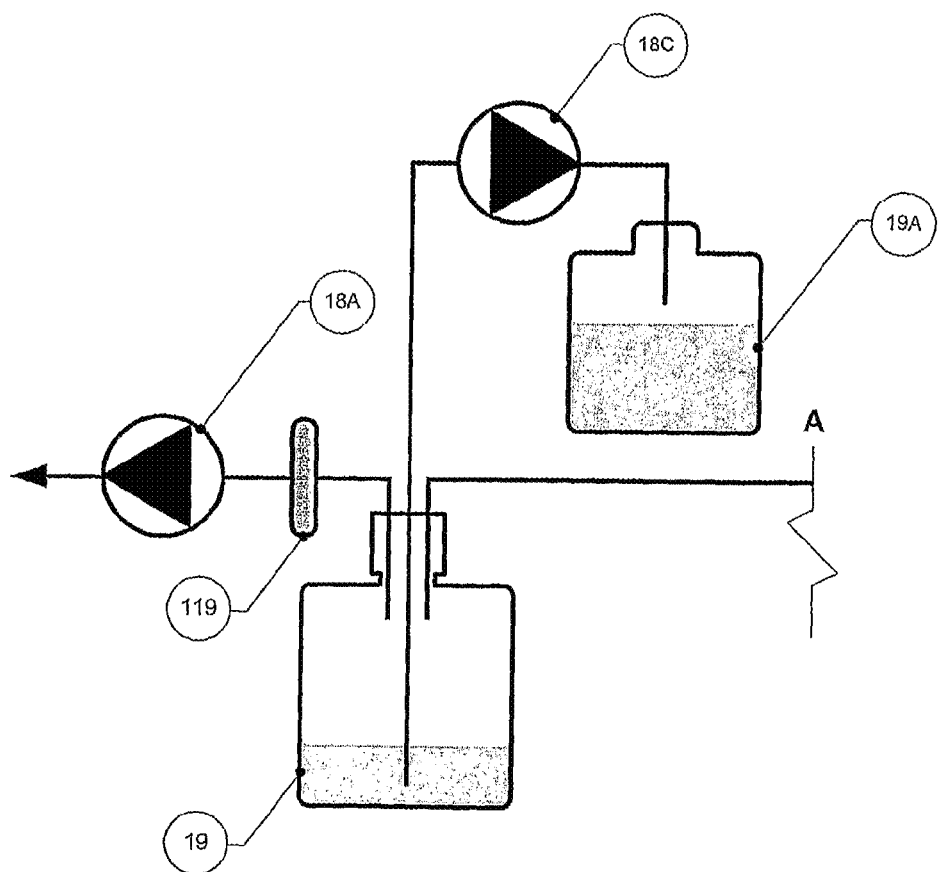

Referring to FIG. 28B, this shows another alternative layout of the essentially identical, and identically numbered, components in FIG. 12C downstream of point B in FIG. 11A, and alternative means for handling the aspirate flow to the aspirate collection vessel under negative or positive pressure to the wound. The pressure monitor (116) is omitted, as is the feedback connection to a variable-speed first device (18A), here a variable-speed pump, downstream of the aspirate collection vessel (19) and the filter (119).

A third device (18C), here a fixed-speed pump, provides means for moving fluid from the aspirate collection vessel (19) into a waste bag (12C). The operation of the apparatus is as described hereinbefore.

Referring to FIG. 29, this shows an alternative layout of the essentially identical, and identically numbered, components in FIG. 11A upstream of point A in FIG. 11A.

It is a single-pump system essentially with the omission from the apparatus of FIG. 11A of the second device for moving irrigant fluid into the wound dressing. The operation of the apparatus is as described hereinbefore.

The use of the apparatus of the present invention will now be described by way of example only in the following Example:

Example 1

Removal of Wound Proteins and Derivatives with a Two-Pump Apparatus

In this example, a gelatine sheet laid in a cavity wound model represents wound proteins and derivatives to be removed by the two-pump apparatus. The dressing is essentially identical with that in FIGS. 18A-B, i.e. it comprises a circular backing layer and a lobed chamber in the form of a deeply indented disc much like a multiple Maltese cross or a stylised rose, defined by an upper impervious membrane and a lower porous film with apertures that deliver the irrigant fluid directly from the wound bed over an extended area.

A two-pump system was set up essentially as in FIG. 2, with an irrigant dispensing bottle—1000 ml Schott Duran, connected to a peristaltic pump (Masterflex) for irrigant delivery, and associated power supply and supply tube, a diaphragm vacuum pump (Schwarz) for aspiration, and associated power supply and offtake tube, connected to a vacuum vessel (aspirate collection jar)—Nalgene 150 ml polystyrene each pump being connected to a dressing consisting of the following elements:

i) a wound contacting element, comprising a lobed bag with low porosity 'leaky' membrane wound contact layer on the lower surface, impervious film on the top, and a foam spacer between the two layers to allow free flow of irrigant solution.

ii) a space filling element, comprising a reticulated, open-cell foam (black reticulated foam, Foam Techniques) 30 mm thick, 60 mm diameter iii) an occlusive adhesive coated polyurethane backing layer top film (Smith & Nephew Medical) with acrylic pressure sensitive adhesive iv) two tubes passing under the occlusive top film, and sealed to prevent leakage of gas or liquid:

a. one tube centrally penetrating the top film of the wound-contacting element to deliver irrigant into the chamber formed by this film and the porous element;

b. the other tube of approximately equal length to remove aspirate with the opening positioned just above the top film of the wound contacting element.

Preparation of Gelatine Sheet:

A 20% aqueous solution of gelatine was prepared by weighing gelatine into a glass jar and making it up to the required weight with deionised water. The jar was placed in an oven (Heraeus), at set temperature 85° C. After 60 minutes the jar was removed from the oven and shaken, to encourage mixing. Petri dishes were partially filled with 10 g quantities of the gelatine solution and placed in a fridge (LEC, set temperature: 4° C.) to set for at least 1 hour. Final thickness of the gelatine slab was 5 mm. Petri dishes containing the gelatine slabs were removed from the fridge at least 2 hours before use.

Preparation of Test Equipment and Materials

Irrigant solution (deionised water) and the Perspex wound model were pre-conditioned in an oven (Gallenkamp) at set temperature 37° C., for at least 4 hours before use.

For each test, a freshly prepared gelatine slab was removed from a Petri dish and weighed.

The Perspex wound model was then removed from the oven and the gelatine slab placed at the bottom of the cavity. Application of the dressing to the wound model was as follows:

the wound contacting element was carefully placed over the gelatine slab the foam filler was placed on top of this with the irrigant and aspirate tubes running centrally to the top of the cavity (the foam filler was slit to the centre to facilitate this).

the side entry port, pre-threaded onto the tubes, was adhesively bonded to the upper surface of the wound model block using an acrylic pressure sensitive adhesive the top adhesive coated film was applied over all of the elements and pressed down to give a seal on all sides, and especially around the tube entry/exit point Application of the dressing to the wound model was the same for all tests performed. All tubing used was the same for each experiment (e.g. material, diameter, length).

Simultaneous Irrigation & Aspiration

A schematic diagram of the system used in the experiment is shown below. For the experiment most of the apparatus (not including the pumps, power supply, and connecting tubing to and from the pumps) was placed in an oven (Gallenkamp, set temperature: 37° C.), on the same shelf.

Before starting the irrigation pump a vacuum was drawn on the system to check that the dressing and tube connections were substantially airtight (the pumping system was controlled to give a pressure at the vacuum vessel of approximately −75 mmHg before opening the system up to include the dressing).

Once system integrity had been confirmed, the irrigation pump was started (nominal flow rate: 50 ml/hr), i.e. both pumps running together. Timing of the experiment was started when the advancing water front within the irrigant tube was observed to have reached the top of the dressing.

After 60 minutes, the irrigation pump was stopped, shortly followed by the vacuum (aspiration) pump.

Aspirate liquid collected in the vacuum jar was decanted into a glass jar. The vacuum jar was rinsed with ~100 ml of deionised water and this added to the same glass jar.

The aspirate solution was placed in an oven (Heraeus, set temperature: 130° C.) and dried to constant weight.

Sequential Irrigation & Aspiration

The experimental set up was as for the simultaneous irrigation/aspiration experiment.

Before starting the experiment a vacuum was pulled on the system to check that the dressing and tube connections were substantially airtight. The pumping system was controlled to give a pressure at the vacuum vessel of approximately −75 mmHg before opening the system up to include the dressing. Once system integrity had been confirmed, the irrigation pump was started (nominal rate: 186 ml/hr) and run until the advancing water front in the irrigant tube was observed to have reached the top of the dressing. The pump was temporarily stopped at this point whilst the vacuum line was sealed (using a tube clamp) and the vacuum pump stopped.

Timing of the experiment was from the point the irrigation pump was restarted. The pump was run until 50 ml of irrigant had entered the wound model (just over 16 minutes at the rate of 186 ml/hr). At this point the irrigant pump was stopped.

It was observed that during the filling phase of sequential filling and flushing, air trapped in the model wound cavity caused the top film of the dressing to inflate substantially, to a point approaching failure.

After a further ~44 minutes (60 minutes from the start of the experiment) the vacuum pump was started and the tube clamp on the aspirate line removed. The wound model was aspirated for 5 minutes. Towards the end of this period a small leak was introduced into the top film of the dressing to maximise the amount of fluid drawn from the wound model (it was observed that as the pressure differential between the wound model cavity and the vacuum jar reduced to zero, the flow of aspirate also tended to slow. Introducing a small leak re-established the pressure differential and the flow of aspirate out of the cavity).

Results

| Simultaneous Irrigation & Aspiration | | | |
|---|---|---|---|
| Reference number | Aspirate recovered (g) | Recovery of gelatine (%) | Concentration of gelatine in aspirated fluid (% w/w) |
| 1 | 48.81 | 79.33 | 3.27 |
| 2 | 45.64 | 72.30 | 3.18 |
| 3 | 48.84 | 68.05 | 2.76 |
| Mean | 47.76 | 73.22 | 3.07 |

| Sequential Irrigation & Aspiration | | | |
|---|---|---|---|
| Reference number | Aspirate recovered (g) | Recovery of gelatine (%) | Concentration of gelatine in aspirated fluid (% w/w) |
| 1 | 32.08 | 19.59 | 1.23 |
| 2 | 34.09 | 18.35 | 1.07 |
| 3 | 33.90 | 10.77 | 0.64 |
| Mean | 33.36 | 16.24 | 0.98 |

Conclusions

Simultaneously irrigating and aspirating the wound model removed more of the gelatine placed at the base of the wound model cavity than sequentially filling and emptying the cavity, even though the amount of liquid entering the wound and the duration of the experiment were the same in both cases. Simultaneously irrigating and aspirating also removed more fluid from the model wound.

Example 2

The Combination of Simultaneous Fluid Flow (Irrigation) and Aspiration (Under Reduced Pressure) on Wound Bed Fibroblasts Compared with the Exposure of Wound Bed Fibroblasts to Repeated Fill-Empty Cycles of Fluid Flow and Aspiration An apparatus of the present invention was constructed essentially as in FIG. 30, which is an apparatus where an irrigant is delivered continually to the wound bed and the resultant wound exudate/fluid mixture is at the same time continually aspirated from the wound. Alternative systems are known where the wound is subjected to repeated iteration of a cycle of fluid delivery followed by a period of aspiration under reduced pressure.

The apparatus comprised a surrogate wound chamber (Minucells perfusion chamber) in which normal diploid human fibroblasts were cultured on 13 mm diameter (Thermanox polymer) cover slips retained in a two part support (Minucells Minusheets). Tissues present in the healing wound that must survive and proliferate were represented by the cells within the chamber. Nutrient medium (DMEM with 10% FCS with 1% Buffer All) to simulate an irrigant fluid/wound exudate mixture, was pumped from a reservoir into the lower aspect of the chamber where it bathed the fibroblasts and was removed from the upper aspect of the chamber and returned to a second reservoir. The wound chamber was maintained at less than atmospheric pressure by means of a vacuum pump in line with the circuit.

The pumps for the circuit were peristaltic pumps acting on silicone (or equivalent) elastic tubing. The circuit was exposed to a vacuum of no more than 10% atmospheric pressure, 950 mbar and atmospheric pressure varied up to a maximum value of 1044 mbar. The internal diameter of the tubing was 1.0 mm. A total volume for the circuit including the chamber and the reservoir of between 50 and 220 ml was used. The flow rates used were at a number of values between 0.1 ml min$^{-1}$ and 2.0 ml$^{-1}$ min$^{-1}$.

An experiment was conducted that simulated conditions that are not uncommon for healing wounds whereby a fluid was delivered to the wound bed and the application of a vacuum was used to remove the mixture of fluid and exudate to a waste reservoir.

An air bleed fluid control valve was additionally positioned in the circuit so that on opening the air bleed occurred for a time and closed the fluid flow, the simulated irrigant fluid/wound exudate mixture was evacuated from the chamber and the fibroblasts were maintained under a negative pressure relative to the atmosphere. This represents an empty/fill system.

Results And Conclusions

The following results were obtained for a circuit comprising a wound chamber as above containing a total volume of nutrient media (154 ml) pumped at a flow rate of 0.2 ml min$^{-1}$ and where vacuum was set at 950 mbar and where atmospheric pressure varied up to a maximum value of 1044 mbar. The wound chamber and media were held at 37° C. for 25 hours. In one set of wound chambers continuous flow was maintained. In a second set of chambers 6 cycles of empty/fill were performed with each fill or empty phase lasting 1 hour.

In controls where empty/fill system with 6× cycles of 1 hour empty/1 hour fill over a total of 25 hours, the survival and growth of the fibroblasts is inhibited.

However, when the nutrient medium flow in the first circuit is delivered continually to the Minucells chamber and the resultant nutrient medium is at the same time continually aspirated from the Minucells chamber under vacuum was set at 950 mbar and where atmospheric pressure varied up to a maximum value of 1044 mbar, the fibroblasts survive and proliferate to a greater extent during a 25 hour period than the control empty/fill circuits

| Conditions | Mean relative level of cell activity* after 25 hours. |
|---|---|
| Baseline cell activity prior to introduction to wound chamber | 100% |
| Fill empty 6 cycles | 93% |
| Continuous flow | 143% |

*Cell activity measured with a WST (Tetrazolium based mitochondrial dehdrogenase activity assay). Data normalised to fibroblasts seeded onto coverslips with normal nutrient media baseline activity The combination of continuous fluid flow at 0.2 ml min$^{-1}$ and waste fluid removal under vacuum of no more than 10% atmospheric pressure, 950 mbar and atmospheric pressure varied up to a maximum value of 1044 mbar, enhances the cell response necessary for wound healing more than the fill empty fill pattern under vacuum.

What is claimed is:

1. An apparatus for aspirating and irrigating wounds, comprising:
   a backing layer capable of forming a fluid-tight seal over a wound;
   a fluid supply tube configured to supply fluid from a fluid reservoir to the wound;
   an outlet tube configured to supply negative pressure to the wound;
   a control device configured to control the fluid supply such that fluid from the fluid reservoir is supplied to the wound in a plurality of fluid supply cycles, each fluid supply cycle supplying a volume of fluid with a time period between fluid supply cycles, the control device configured to cycle negative pressure between a first level and a second level;
   a bleed regulator connected to the outlet tube or configured to connect to a wound space for the regulation of positive or negative pressure applied to the wound.

2. The apparatus of claim 1, further comprising a pressure monitor configured to measure negative pressure.

3. The apparatus of claim 2, wherein the bleed regulator is configured to be controlled by the pressure monitor.

4. The apparatus of claim 2, wherein a measurement of the pressure at the wound enables control of operation of at least one of a negative pressure source or an irrigant pump.

5. The apparatus of claim 1, wherein the pressure monitor is connected to a monitor offtake tube.

6. The apparatus of claim 5, wherein the monitor offtake tube is configured to be in fluid communication with the wound through the backing layer.

7. The apparatus of claim 1, wherein the bleed regulator comprise a bleed tube configured to be connected to the backing layer.

8. The apparatus of claim 1, wherein the bleed regulator comprises a valve configured to vent the wound from the atmosphere.

9. The apparatus of claim 1, further comprising a negative pressure pump, the negative pressure pump configured to connect to the outlet tube.

10. The apparatus of claim 1, further comprising an irrigant pump, the irrigant pump configured to be connected to the fluid supply tube.

11. The apparatus of claim 1, further comprising one or more bosses.

12. The apparatus of claim 11, wherein each of the one or more bosses received both the fluid supply tube and the outlet tube.

13. The apparatus of claim 11, wherein at least one of the one or more bosses is circular.

14. The apparatus of claim 1, further comprising a wound filler.

15. The apparatus of claim 14, wherein the wound filler comprises foam.

* * * * *

UNITED STATES PATENT AND TRADEMARK OFFICE
CERTIFICATE OF CORRECTION

Page 1 of 4

PATENT NO. : 10,758,424 B2
APPLICATION NO. : 15/894706
DATED : September 1, 2020
INVENTOR(S) : Patrick Lewis Blott It is certified that error appears in the above-identified patent and that said Letters Patent is hereby corrected as shown below:

On the Title Page

Column 2, Item (57), Line 3, under Abstract, delete "would" and insert --wound--.

Column 2, Item (57), Line 4, under Abstract, delete "would" and insert --wound--.

Column 2, Item (57), Line 6, under Abstract, delete "Path" and insert --path--.

Column 2, Item (57), Line 11, under Abstract, delete "would" and insert --wound--.

On Page 4, Column 2, Item (56), Line 39, under U.S. Patent Documents, delete "Blatt" and insert --Blott--.

On Page 6, Column 2, Item (56), Line 15, under Other Publications, delete "Www" and insert --www--.

On Page 6, Column 2, Item (56), Line 22, under Other Publications, delete "GB/2005/004177" and insert --GB2005/004177--.

On Page 6, Column 2, Item (56), Line 26, under Other Publications, delete "GB/2005/004177" and insert --GB2005/004177--.

On Page 6, Column 2, Item (56), Line 51, under Other Publications, delete "4892)," and insert --4892,--.

On Page 6, Column 2, Item (56), Line 59, under Other Publications, delete "71 B" and insert --71B--.

On Page 7, Column 1, Item (56), Line 21, under Other Publications, delete "Absorable" and insert --Absorbable--.

Signed and Sealed this
Ninth Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,758,424 B2

On Page 7, Column 1, Item (56), Line 22, under Other Publications, delete "Obsterics" and insert --Obstetrics--.

On Page 7, Column 1, Item (56), Line 29, under Other Publications, delete "Stei-Greffe" and insert --Steri-Greffe--.

On Page 7, Column 1, Item (56), Line 69, under Other Publications, delete "PRIMATRIXTM" and insert --PRIMATRIX™--.

In the Specification

In Column 1, Line 50, delete "(which" and insert --which--.

In Column 4, Line 25, delete "irrigate dwell" and insert --irrigate—dwell--.

In Column 4, Line 43, delete "exudate)," and insert --exudate.),--.

In Column 4, Line 43, delete "and or" and insert --and/or--.

In Column 4, Line 64, delete "equilibrium" and insert --equilibrium.--.

In Column 5, Line 15, delete "tube;" and insert --tube.--.

In Column 5, Line 55, delete "valves." and insert --valves;--.

In Column 6, Line 47, delete "housing." and insert --housing--.

In Column 6, Line 50, delete "rotor." and insert --rotor--.

In Column 10, Line 45, delete "present)." and insert --present.--.

In Column 13, Line 38, delete "ulcers." and insert --ulcers).--.

In Column 15, Line 18, delete "wound," and insert --wound.--.

In Column 16, Line 1, delete "(optionally" and insert --optionally--.

In Column 17, Line 18, delete "etc" and insert --etc.--.

In Column 17, Line 22, delete "etc" and insert --etc.--.

In Column 18, Line 44, delete "a" and insert --as--.

In Column 19, Line 11, delete "flange" and insert --flange.--.

In Column 20, Line 10, delete "manifold," and insert --manifold.--.

CERTIFICATE OF CORRECTION (continued)
U.S. Pat. No. 10,758,424 B2

In Column 20, Line 43, delete "boustrophedic" and insert --boustrophedonic--.

In Column 21, Lines 43-44, delete "lidocaine lignocaine/lignocaine" and insert --lidocaine/lignocaine--.

In Column 21, Line 44, delete "xylocalne" and insert --xylocaine--.

In Column 22, Line 57, delete "e.g., e.g." and insert --e.g.--.

In Column 23, Line 2, delete "equilibrium" and insert --equilibrium.--.

In Column 24, Line 49, delete "11C." and insert --11C,--.

In Column 25, Line 7, delete "FIG." and insert --FIGS.--.

In Column 26, Lines 48-49, delete "hereinbefore" and insert --hereinbefore.--.

In Column 26, Line 67, delete "(43)," and insert --(43).--.

In Column 27, Line 4, delete "frustroconical," and insert --frustoconical,--.

In Column 27, Line 42, delete "frustroconical," and insert --frustoconical,--.

In Column 29, Lines 3-4, delete "8a and 8b," and insert --8A and 8B,--.

In Column 29, Line 10, delete "boustrophedic" and insert --boustrophedonic--.

In Column 29, Line 52, delete "((not" and insert --(not--.

In Column 30, Line 26, delete "though" and insert --through--.

In Column 30, Line 37, delete "though" and insert --through--.

In Column 31, Line 24, delete "hereinbefore" and insert --hereinbefore.--.

In Column 31, Line 32, delete "hereinbefore" and insert --hereinbefore.--.

In Column 31, Line 40, delete "hereinbefore" and insert --hereinbefore.--.

In Column 31, Line 50, delete "hereinbefore" and insert --hereinbefore.--.

In Column 31, Lines 61-62, delete "hereinbefore" and insert --hereinbefore.--.

In Column 32, Lines 6-7, delete "hereinbefore" and insert --hereinbefore.--.

In Column 32, Line 58, delete "FIG." and insert --FIGS.--.

CERTIFICATE OF CORRECTION (continued)
U.S. Pat. No. 10,758,424 B2

In Column 33, Line 26, delete "wounds" and insert --wounds.--.

In Column 33, Line 54, delete "on" and insert --one--.

In Column 36, Line 23, delete "solution." and insert --solution--.

In Column 36, Line 47, delete "5 mm." and insert --~5 mm.--.

In Column 36, Line 64, delete "this)." and insert --this)--.

In Column 37, Line 3, delete "point" and insert --point.--.

In Column 39, Line 5, delete "ml$^{-1}$" and insert --ml--.

In Column 39, Line 41 (Approx.), delete "circuits" and insert --circuits.--.

In Column 39, Line 51 (Approx.), delete "dehdrogenase" and insert --dehydrogenase--.

In Column 39, Line 53 (Approx.), delete "activity" and insert --activity.--.